(12) United States Patent
Deliwala

(10) Patent No.: US 7,339,170 B2
(45) Date of Patent: Mar. 4, 2008

(54) OPTICAL ENCODING AND RECONSTRUCTION

(76) Inventor: Shrenik Deliwala, 16 Kathleen Dr., Andover, MA (US) 01810

( * ) Notice: Subject to any disclaimer, the term of this patent is extended or adjusted under 35 U.S.C. 154(b) by 154 days.

(21) Appl. No.: 10/892,740

(22) Filed: Jul. 16, 2004

(65) Prior Publication Data

US 2005/0058352 A1   Mar. 17, 2005

Related U.S. Application Data

(60) Provisional application No. 60/487,640, filed on Jul. 16, 2003.

(51) Int. Cl.
G01J 5/00 (2006.01)
(52) U.S. Cl. .................................................... 250/351
(58) Field of Classification Search ................. 250/351
See application file for complete search history.

(56) References Cited

U.S. PATENT DOCUMENTS

| | | | | |
|---|---|---|---|---|
| 3,083,299 A | | 3/1963 | Cruse | 250/203 |
| 3,151,247 A | | 9/1964 | Auvermann | 250/226 |
| 3,160,751 A | | 12/1964 | Dunning | 250/83.3 |
| 3,825,348 A | | 7/1974 | Nomarski et al. | 356/107 |
| 3,846,630 A | | 11/1974 | Suhami et al. | 250/207 |
| 4,086,652 A | * | 4/1978 | Mantz | 708/813 |
| 4,287,412 A | | 9/1981 | Couderc et al. | 250/203 |
| 5,017,783 A | * | 5/1991 | Mousavi | 250/353 |
| 5,433,197 A | * | 7/1995 | Stark | 600/319 |
| 5,526,121 A | | 6/1996 | Sandifer et al. | 356/418 |
| 5,737,075 A | * | 4/1998 | Koch et al. | 356/310 |
| 6,177,674 B1 | | 1/2001 | Rutt et al. | 250/351 |
| 2004/0095626 A1 | * | 5/2004 | Brady | 359/237 |

OTHER PUBLICATIONS

Golay, Marcel J.E., "Complementary Series" *IRE Transactions on Information Theory*, Apr. 1961, pp. 82-87.
Riesenberg, Rainer et al., "HADAMARD-Minispectrometer made by a Micro Device", *Proceedings "3rd Round Table on Micro/Nano Technologies for Space"*, (May 15-17, 2000).
Sun, P.C. et al., "Real-time one-dimensional coherent imaging through single-mode fibers by space-time conversion processors", *Optics Letters*, vol. 22, No. 24, pp. 1861-1863 (Dec. 15, 1997).
Wuttig, A. et al., "Sensitive Hadamard Transform Imaging Spectrometer with a simple MEMS", in Fujuisada: Sensors, Systems, and Next Generation Satellites VIII, *Proc. SPIE*, vol. 4881 (2002).
Wuttig, Andreas et al., "Single Element Detector and Optical Modulator contra Focal Plane Array for Thermal Imaging", $IRS^2$ 2002 Proceedings, pp. 103-108 (2002).
Rao, Ramon et al., "Parallel Implementation of the Filtered Back Projection Algorithm for Tomographic Imaging", http://www.sv.vt.edu/xray_ct/parallel/Parallel_CT.html (Apr. 5, 1995).

* cited by examiner

*Primary Examiner*—David Porta
*Assistant Examiner*—Shun Lee
(74) *Attorney, Agent, or Firm*—Fish & Richardson P.C.

(57) ABSTRACT

The invention features methods including: (i) modulating multiple components (e.g., different spatial regions, different wavelengths, or both) of electromagnetic (EM) radiation emerging from an object with different time-varying functions; (ii) measuring at least one time-varying signal derived from the modulated EM radiation emerging from the object; and (iii) reconstructing information about the object based on the measured signal and the time-varying functions.

50 Claims, 23 Drawing Sheets

Figure 5
Figure 5a
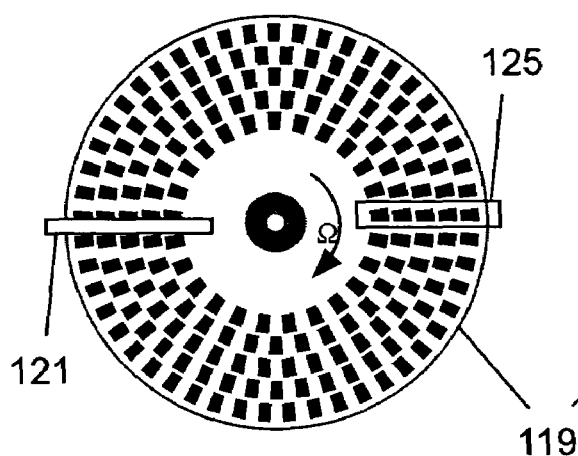
Figure 5b
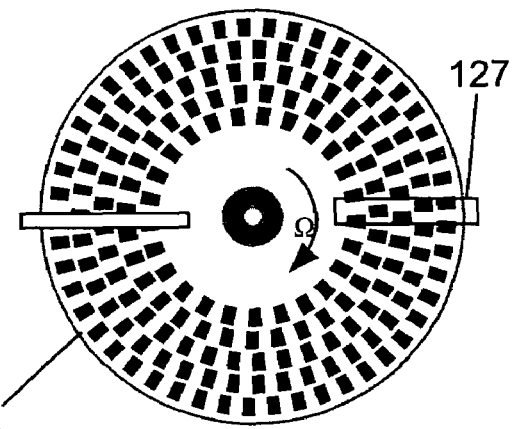
Figure 5c
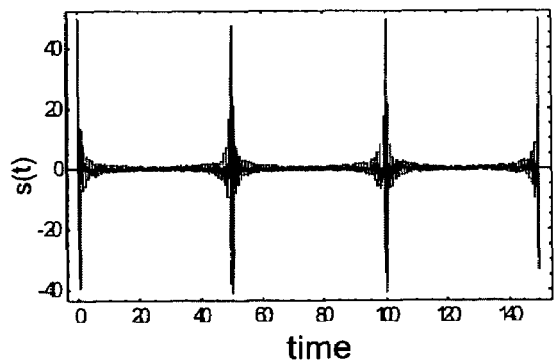
Figure 5d
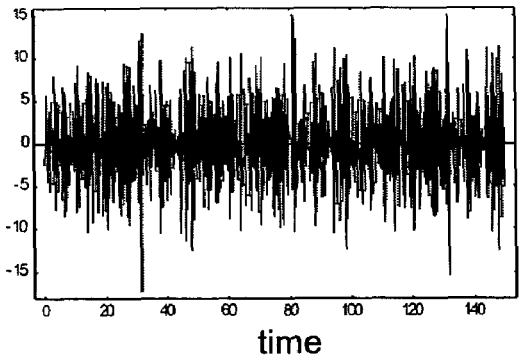

Figure 6
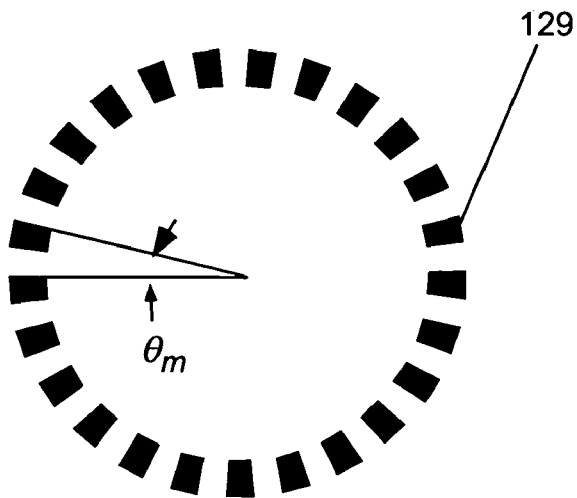
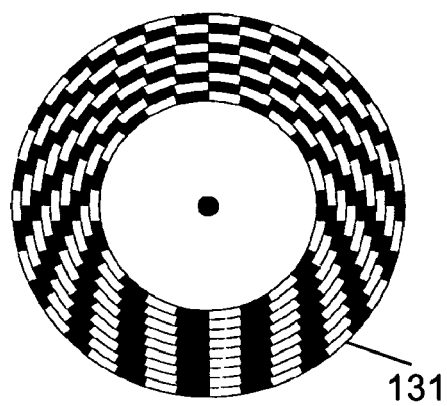
Figure 7a
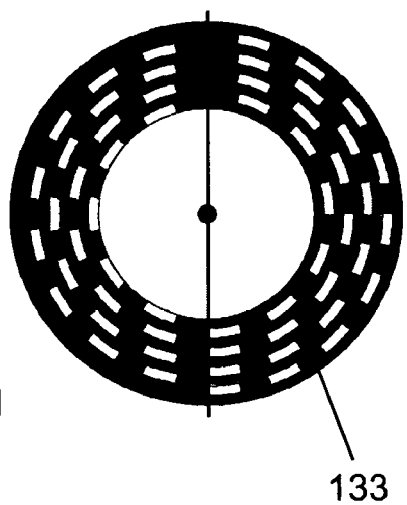
Figure 7b
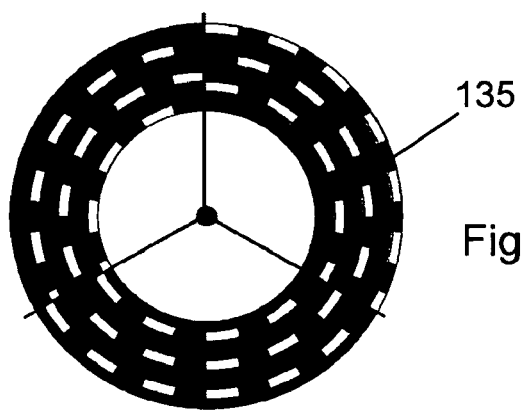
Figure 7c Figure 13
Figure 13a
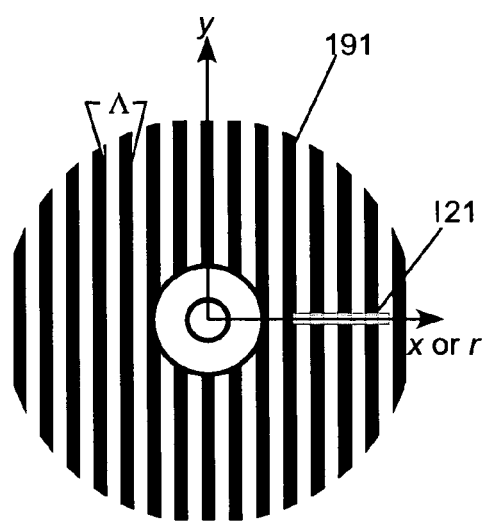
Figure 13b
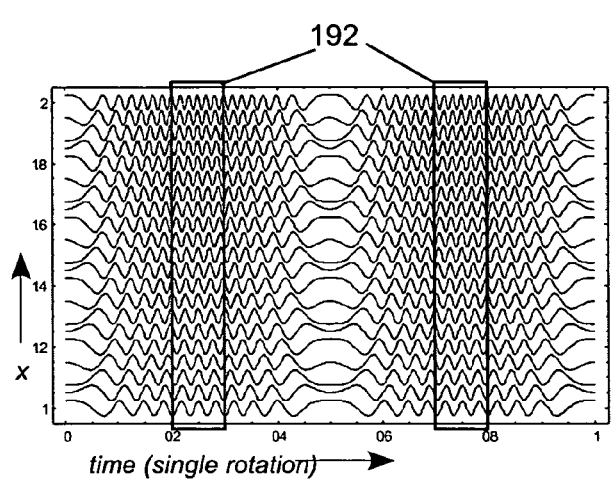
time (single rotation)
Figure 13c
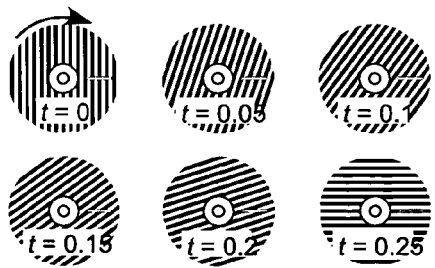
Figure 13d
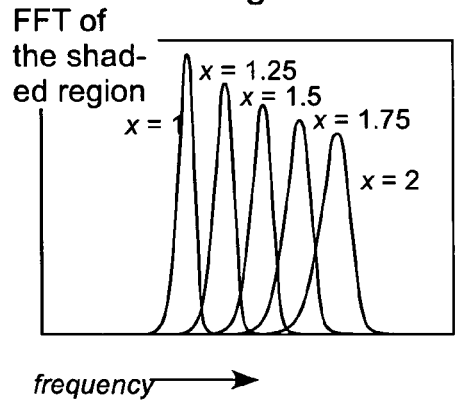
FFT of the shaded region
frequency Figure 14
Figure 14a
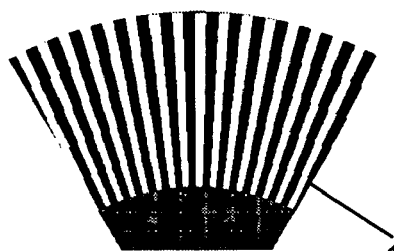
Figure 14c
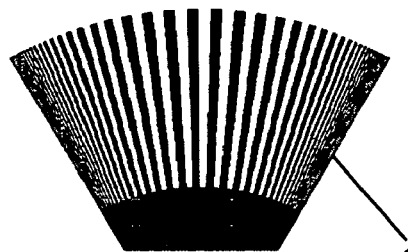
Figure 14b
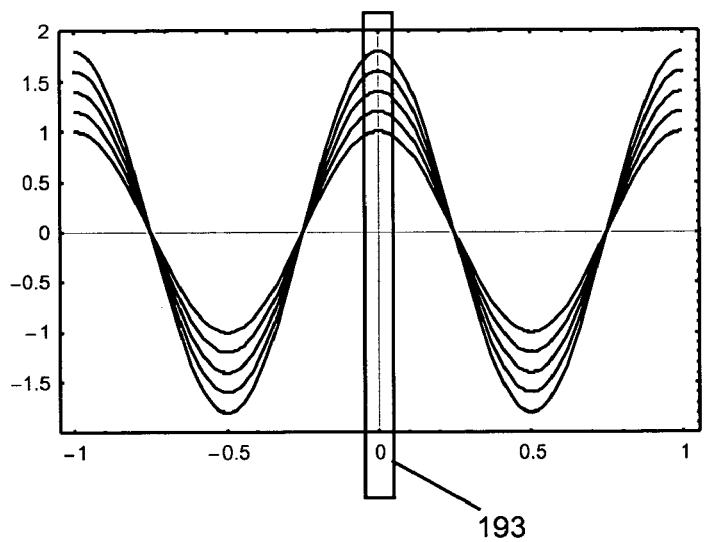
Figure 15
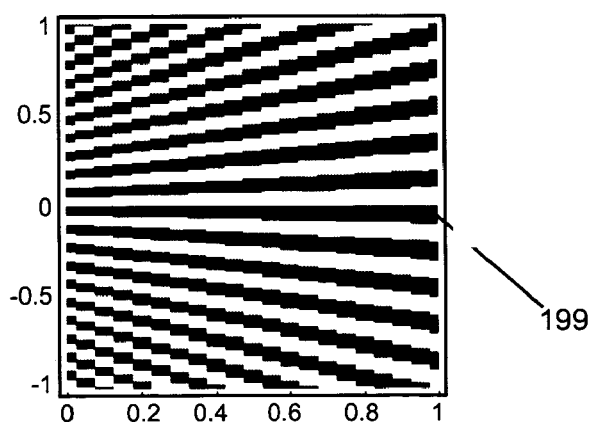

Figure 23
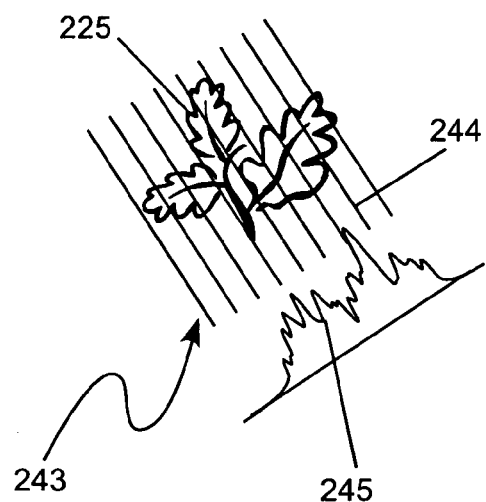
Figure 24
Figure 24a
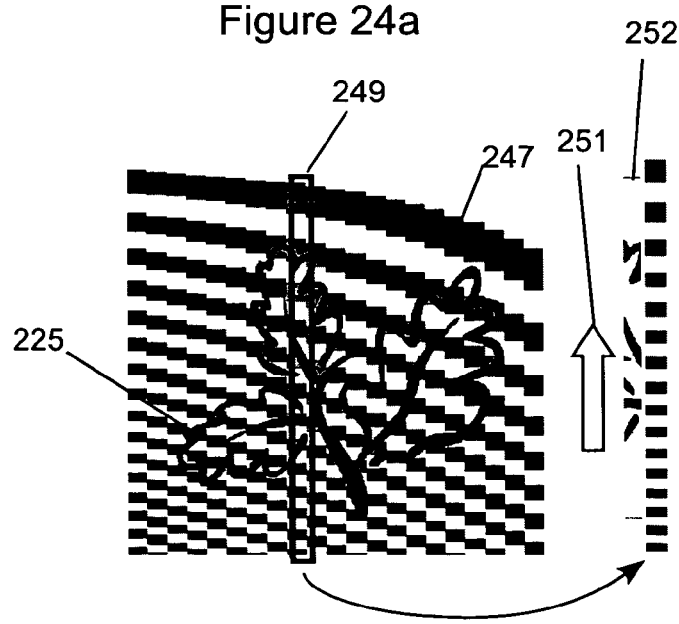
Figure 24b
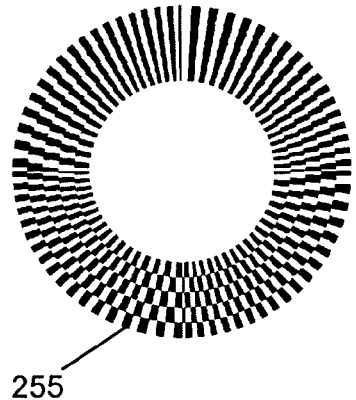

PRIOR ART

Figure 26
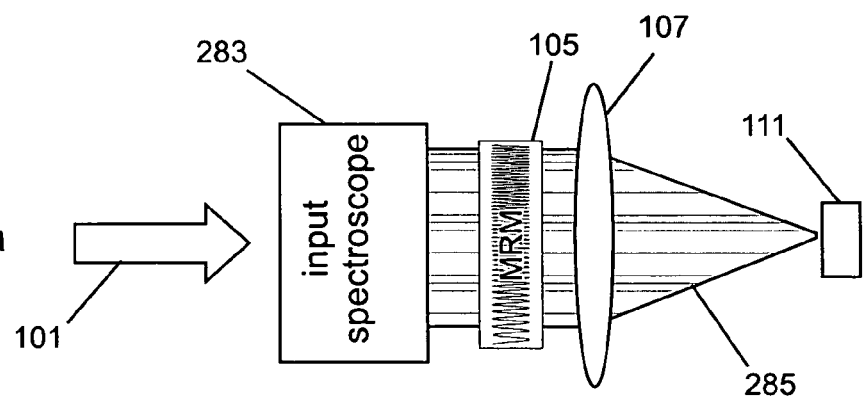
Figure 26a
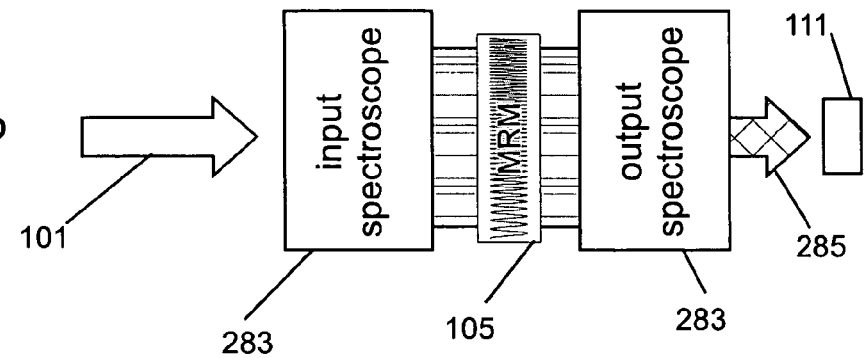
Figure 26b
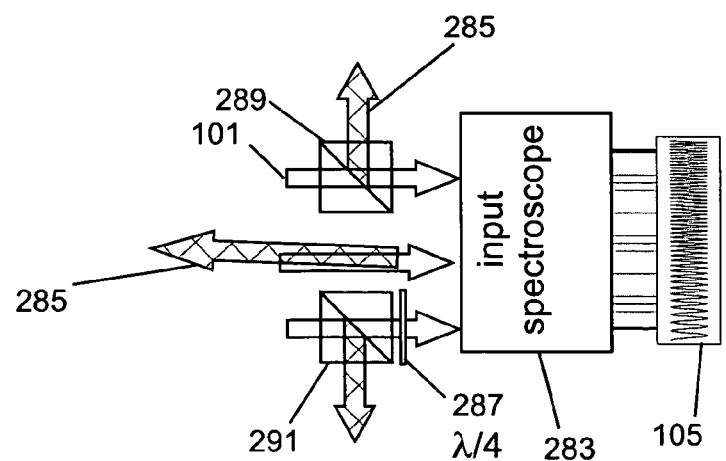
Figure 26c
Figure 26d
Figure 26e

OPTICAL ENCODING AND RECONSTRUCTION

CROSS-REFERENCE TO RELATED APPLICATIONS

This application claims priority to U.S. Provisional Patent Application Ser. No. 60/487,640 filed Jul. 16, 2003 and entitled "Optical encoding and reconstruction", the contents of which are incorporated herein by reference.

FIELD OF INVENTION

This invention relates to a technique of encoding a one or two dimensional spatial information, its collection, and its computational reconstruction. The disclosed methods may be applied to the problem of imaging electromagnetic radiation, spectroscopy, and many other methods that usually require a one or two dimensional pixelated array of detectors.

BACKGROUND

Electronic one-dimensional (1D) and two-dimensional (2D) imaging systems are in wide use. Examples of these include a 1D array of detectors for scanning images and a digital camera consisting of a 2D array of detectors. These detectors come in wide variety and employ many different read techniques. Typical features of these popular imaging systems are:

(a) A number of discrete detectors are used to sample 1D or 2D information.
(b) Higher resolution (as defined by pixels per unit length) is obtained by physically increasing the number of detector elements. For example, a 2D image formed by the optical imaging system may be collected using a CMOS-based imaging array. Higher the number of detector elements in each dimension, better the quality of the image.
(c) Higher resolution requires manufacturing each detector in close proximity to the other. A typical high-resolution CCD or a CMOS camera in the visible part of the electromagnetic spectrum may have a pixel size of 6-10 µm or a resolution of approximately 100 lines/mm. In contrast, a good photographic film provides a resolution of 1000-3000 lines/mm.
(d) In the visible region, silicon-based detectors work adequately and with good quantum efficiency. The cost of the focal plane arrays have fallen dramatically in recent times. But outside the visible region of the electromagnetic spectrum, novel and often exotic materials are required to form detectors and focal plane arrays. Factors such as yield, manufacturability, uniformity, or compatibility of these detector arrays with read-out electronics limits either the size of arrays or makes them very expensive compared to the Silicon-based detectors. For example, a 1000 by 1000 array of silicon detectors (as in a typical Mega-pixel digital camera) costs less than $10 to manufacture—the entire camera can be purchased for less than $100. But an array of 256 by 256 pixels sensitive to 1.3-1.5 µm region of the electromagnetic spectrum can cost upwards of $1000, with the camera itself costing tens of thousands of dollars. Other exotic/special materials for detectors include Mercury-Cadmium-Telluride system (3-10 µm), PbS (2-5 µm), PtSi (8-12 µm), $LiTaO_2$ (as pyroelectric element), scintillators for UV and X-ray etc.
(e) In many cases, the imaging array needs to be cooled to reduce noise. This is particularly true in the infrared portion of the spectrum since the photon energy becomes comparable the energy of the thermal fluctuations at room temperature. Bigger detector arrays require more expensive cooling equipment as well as uniform cooling across the array.
(f) In many regions of the electromagnetic spectrum, imaging detectors are plagued by complex manufacturing steps, exotic materials, difficult or tedious calibration of individual pixels, long testing times, and number of dead pixels. These are some of the difficulties that keep the cost of imaging high.
(g) Most of the detector arrays are made on a plane substrate forcing optical designers to design imaging systems that have a planar imaging surface.

SUMMARY

The invention features a multirate modulator (also refered to herein as multirate image encoder) that modulates a spatially varying information I(x) in case of a one dimensional (1D) image or I(x, y) in case of a two dimensional image (2D) such that intensity at each location x or (x, y) is encoded with unique, time-varying function $G_m(t)$. The system establishes a one to one correspondence between the index m and the coordinate $\vec{x}$ (where $\vec{x}$ denotes both 1D and the 2D). For an N-pixel image, N unique functions may be assigned indexed by the subscript m. After modulation by a set of functions $G_m(t)$, the dynamically encoded light or the electromagnetic radiation from all the locations $\vec{x}$ is collected on a single detector. The detector receives a time varying signal s(t) given by $$s(t) = \sum_{m=1}^{N} I(\vec{x}) G_{m(\vec{x})}(t) \quad (1)$$

This detector signal may be digitized using an analog-to-digital converter (ADC) after suitable amplification and filtering. If the functions $G_m(t)$ form an orthogonal set, then the original image can be reconstructed by using the orthogonality condition. More generally, the map $\vec{x} \Leftrightarrow m()$ may be used to provide novel functionality to the imaging system. I disclose detailed, practical methods and apparatus for multirate spatial modulation of both 1D and 2D images, algorithms for reconstruction, and other signal processing considerations. I will refer to the object that provides spatially varying multiple modulation functions as multirate modulator and the electromagnetic radiation as being dynamically encoded after passage through multirate modulator.

In the first part of the disclosure, I use a patterned rotating disk as an example of a multirate modulator to ease the description of various properties of imaging based on dynamically encoded electromagnetic radiation. Other methods that provide multirate modulation and appropriate image reconstruction are then disclosed. In each case, embodiments of multirate modulator provide a map between functions indexed by m and the coordinate $\vec{x}$.

Embodiments of the multirate modulator that dynamically encodes electromagnetic radiation when combined with the reconstruction algorithms may include any of the following features and advantages:

(a) A single or a dual (other one acting as a reference in some cases) detector(s) may be used to collect full 1D or 2D image information simultaneously. In such cases, it is not like a simple scanned system where the image field is scanned across a detector (by moving the detector with respect to the image field or vice versa) and image reproduced sequentially. Signal collected over the entire acquisition time (or frame time) may be used for image reconstruction and the signal-to-noise ratio (S/N) is comparable to a 1D or 2D pixelated imaging detector. In a scanned system, S/N is substantially reduced due to decrease in the integration time for each pixel (by square root of N for N-pixel system, light intensities at detector plane being equal).

(b) The resolution is not determined by the density of detectors (since there may be only one detector) but by the design of the multirate modulator that encodes the information contained in the image.

(c) The image (1D or 2D) is reconstructed by numerically processing the time-varying data (even for a static image) generated by the dynamically encoded radiation.

(d) The resolution of the reconstructed image may be determined in the software.

(e) There is no need to calibrate and test an array of detectors since only one detector may be used for entire image. The choice of the detector will depend on the region of the electromagnetic spectrum. The substantial reduction in number of individual detectors can ease manufacturing and reduce cost. It also opens up the possibility of using very special detector materials that may be extremely difficult to use in an arrayed fashion.

(f) The basic principle of operation and image reconstruction is independent of the wavelength region. Of course the materials for imaging optics and detectors have to be compatible with the electromagnetic region of interest. Section 18 covers applications in many regions of the electromagnetic spectrum—from mm waves to X-rays.

(g) Additional information such as the range of objects from the light source may be measured directly and simultaneously by using the disclosed embodiments. Other information that may be reconstructed may include spectra, polarization states, florescence decay times, etc. This is one of the unique feature of the dynamically encoded image.

(h) The dynamic encoding may be performed either near the illumination source (in some applications) or near the detector (as in imaging of a scene analogous to using a typical camera).

(i) Nonlinear channel encoding of the signals, automatic gain control on different slices of the image, and many other techniques (both algorithms and semiconductor hardware) applicable to a 1D time-domain data may now be applied to spatial data once the dynamical encoding is performed by the multirate modulator.

(j) A pair of multirate modulators may be used to perform "lensless" imaging (Section 19). Although lens based imaging system is generally used to illustrate the principles of various embodiments in this disclosure, a more complex combination of multiple multirate modulators may be used depending on the application, in which even the imaging function may be provided by reconstruction of the dynamically encoded electromagnetic radiation.

Many features and advantages will follow from the detailed description. I now summarize various aspects and features of the invention.

In one aspect, the invention features a method including: (i) modulating multiple components (e.g., different spatial regions, different wavelengths, or both) of electromagnetic (EM) radiation emerging from an object with different time-varying functions; (ii) measuring at least one time-varying signal derived from the modulated EM radiation emerging from the object; and (iii) reconstructing information about the object based on the measured signal and the time-varying functions.

Embodiments of the method may include any of the following features.

The EM radiation emerging from the object may be derived from EM radiation incident on the object, and the multiple components of the EM radiation emerging from the object may be modulated by directly modulating the EM radiation incident on the object. Alternatively, the multiple components of the EM radiation emerging from the object may be modulated by directly modulating the EM radiation emerging from the object.

Each time-varying function may encode information about a corresponding component of the EM radiation emerging from the object in the measured time-varying signal.

The modulating may include modulating any of the amplitude, the phase, and the state of polarization (SOP) of the components of the EM radiation emerging from the object.

Where the components of the EM radiation correspond to different spatial regions, the modulating may include directly modulating EM radiation incident on the object or the EM radiation emerging from the object with a programmable spatial light modulator. Alternatively, the modulating may include directly modulating EM radiation incident on the object or the EM radiation emerging from the object by moving a permanently patterned mask relative to the object. For example, the mask may be rotated relative to the object. Furthermore, the modulating may further include moving a second, permanently patterned mask relative to the object and the first-mentioned mask. Also, the modulating may further includes moving each of the object and the mask relative to each other and a fixed reference frame.

The measuring of the time-varying signal derived from the temporally modulated EM radiation may include directing at least some of the different spatial regions of the EM radiations to a common detector and measuring a time-varying intensity of aggregate EM radiation incident on the common detector.

The at least one time-varying signal may include multiple time-varying signals, and the measuring of the time-varying signals derived from the temporally modulated EM radiation may include directing each of different sets of a plural number of the multiple spatial regions of the EM radiation to a corresponding detector and measuring a time-varying intensity of aggregate EM radiation incident on each detector.

The measuring of the time-vary signal derived from the temporally modulated EM radiation may include directing at least some of the multiple spatial regions of the EM radiation to interfere with reference EM radiation on a common detector and measuring a time-varying interference signal of aggregate EM radiation incident on the common detector, wherein the EM radiation emerging from the object and the reference EM radiation are derived from a common source.

The EM radiation emerging from the object may include wavelengths that span multiple wavelength regions that are separated from one another. Furthermore, the at least one time-varying signal may include multiple time-varying signals, and the measuring of the time-varying signals derived from the temporally modulated EM radiation may include directing at least some of the multiple spatial regions of the EM radiation at wavelengths in each of the multiple wavelength regions to a corresponding detector and measuring a time-varying intensity of aggregate EM radiation incident on each detector. For example, the directing may include using a dispersive optic to direct the EM radiation at wavelengths in each of the multiple wavelength regions to the corresponding detector. Moreover, the reconstructed information may resolve wavelength-dependent features of the object. For example, the reconstructed information may be an RGB image of the object. The method may also include reconstructing the object at wavelengths that span each of the multiple wavelength regions (such as visible, near infrared, and thermal infrared) to produce the EM radiation emerging from the object.

Where the components of the EM radiation correspond to different wavelengths, the modulating may include dispersing source radiation to produce spatially separated wavelengths, directly modulating the spatially separated wavelengths, and directing the modulated wavelengths to contact the object to produce the EM radiation emerging from the object. The modulating may further include recombining the modulated wavelengths before they contact the object. Alternatively, or in addition, the modulated wavelengths may be directed to contact the object at different locations. Furthermore, the directing of the modulated wavelengths to contact the object may include using an optical fiber to couple the modulated wavelengths to the object.

In yet further embodiments in which the EM radiation correspond to different wavelengths, the modulating may include dispersing the EM radiation emerging from the object to produce spatially separated wavelengths and directly modulating the spatially separated wavelengths. The modulating may further include spatially recombining the modulated wavelengths.

The at least one time-varying signal may include M signals, where M is greater than or equal to 1, and the reconstructed information may include N independent data points, where 30N>M.

A direct mapping may exist between each time-varying function and each data point in the reconstructed information.

The method may further include measuring a time-varying reference signal derived from reference EM radiation different from the EM radiation emerging from the object, where the reference EM radiation and the EM radiation emerging from the object are derived from a common source. Furthermore, the reconstructed information may include information about one or more of amplitudes, phases, state of polarization (SOP) information, and wavelengths of the EM radiation emerging from the object relative to the reference EM radiation.

The reconstructed information may include any of a one-dimensional representation of the object, a two-dimensional representation of the object, ellipsometry data about the object, spectroscopic data about the object, information about relative phase differences between various parts of the object, information about relative distances to various parts of the object, any information about decay times of optical excitations of the object.

The EM radiation emerging from object may be derived from a field of view greater than 180 degrees and the reconstructed information includes information about the full field of view.

The EM radiation emerging from the object may be coherent EM radiation or incoherent EM radiation.

The method may further include illuminating the object with incident EM radiation to produce the EM radiation emerging from the object.

The measuring of the time-varying signal may include directing at least some of the EM radiation emerging from the object to a scintillator. For example, the EM radiation emerging from the object may include EM radiation in the X-ray region (e.g., from about 10 nm to about 0.1 pm).

Also, the EM radiation emerging from the object includes EM radiation in the infrared region (e.g., from about 7 microns to about 15 microns). Of course, the EM radiation emerging from the object may also include EM radiation in any of the ultraviolet, visible, near-infrared region, far-infrared, or mm-wave regions.

Detecting the time-varying signal derived from the temporally modulated EM radiation may include coupling the EM radiation emerging from the object to a detector through a flexible light conduits such as an optical fiber, fiber bundle, imaging guides, hollow fibers etc.

The method may further include imaging the radiation from the object onto a modulator used for the modulating of the multiple components. For example, one may use at least one lens or an imaging system with optical power (including diffractive optics, curved mirrors, etc) for the imaging of the EM radiation from the object to the modulator.

The method may further include positioning two modulators in a path of the EM radiation. For example, the radiation from the object may reach the two modulators without passing through an imaging optic with optical power. Furthermore, the reconstructing of the information about the object may use information about a distance between the two modulators.

In general, in another aspect, the invention features an apparatus including: (i) a modulator configured to modulate multiple components of electromagnetic (EM) radiation emerging from an object with different time-varying functions; (ii) a detector optically coupled to the modulator and configured to measure at least one time-varying signal derived from the modulated EM radiation emerging from the object; and (iii) an electronic processor electrically coupled to the detector and the modulator, wherein the electronic processor is configured to reconstruct information about the object based on the measured signal and the time-varying functions.

The apparatus may further include any of the following features.

The apparatus may further include an EM source configured to illuminate the object and produce the EM radiation. Furthermore, the modulator may be positioned along an optical path from the source to the object. Alternatively, the modulator may be positioned along an optical path from the object to the detector.

The apparatus may further include an imaging system positioned to image the EM radiation emerging from the object onto the modulator. For example, the imaging system may further include at least one lens.

The apparatus may further include a second modulator in a path of the EM radiation and spaced from the first-mentioned modulator. For example, the modulators may be configured to receive the EM radiation from the object without the EM radiation passing through an imaging optic. Furthermore, the electronic processor may be configured to use information about a distance between the two modulators for the reconstructing of the information about the object.

Furthermore, the apparatus may include one or more additional features corresponding to any of the features described above in connection to the method.

Unless otherwise defined, all technical and scientific terms used herein have the same meaning as commonly understood by one or ordinary skill in the art to which this invention belongs. All publications, patent applications, patents, and other references mentioned herein are incorporated herein by reference. In case of conflict, the present specification, including definitions, will control.

Other features, objects, and advantages of the invention will be apparent from the following detailed description.

DESCRIPTION OF FIGURES

FIG. 5a and FIG. 5b show examples of a constant and random starting phases in the pattern of the rotating disk respectively and the corresponding FIG. 5c and FIG. 5d show the effect on the time-domain encoded signal.

FIG. 6 illustartes the geometry of the pattern within a ring of a rotating disk modulator for producing narrow modulation frequency.

FIG. 7 show three patterns for rotating disk multirate modulator with each of FIGS. 7a, 7b, and 7c corresponding to acquiring the image in a single frame, two sub-frames and three subframes respectively.

In FIG. 12b, the cylindrical mask is curved to match the curvature of the image field.

FIG. 13a illustrates grating based multirate modulator. In FIG. 13b signal patterns at different radial distances are plotted for a rotating grating shown in FIG. 13c. FIG. 13d is a Fourier Transform showing the frequencies of modulation at different locations during time window marked in FIG. 13b FIG. 14a shows part of the rotating disk used for encoding with oscillatory motion. FIG. 14b shows the variation in the modulation frequency as a function of time at four separate locations. FIG. 14c shows a pattern that increases the window of time during an oscillatory motion when the map of modulation frequency vs space is almost constant.

FIG. 15 shows a mask for multirate modulator based on linear oscillations of the image relative to the pattern.

FIG. 16a shows a beam splitter that creates two line images so that two signal channels are in quadrature while in FIG. 16b a modified mask for the rotating disk multirate modulator is used to acquire the channels in quadrature by multiplexing in time.

FIG. 23 shows lines of constant modulation frequency 243 on image 225 for a two disk multirate modulator and the projection 245 of the image.

FIG. 24a shows the chirped pattern mask for direct reconstruction of a 2D image. FIG. 24b illustrates a chirped pattern for a rotating disk with 4 chirped regions.

FIG. 25a is a schematic of X-ray imager while

FIG. 26a through 26e show various techniques for producing dynamically encoded wavelength spectrum using multirate modulator.

Like reference numerals in different drawings refer to common elements.

DETAILED DESCRIPTION

This invention relates to a technique of encoding a one or two dimensional spatial information, collection, and its computational reconstruction. The disclosed methods may be applied to the problem of imaging electromagnetic radiation, spectroscopy, and other methods that usually require a one or two dimensional pixelated array of detectors. The disclosed method enables new imaging modes such as ranging to be combined with a standard one or two-dimensional image. These novel capabilities are accomplished by a special set of methods for dynamic encoding of the image information. This encoding converts spatial information to a time-varying signal. The image is reconstructed by numerically processing the time-varying signal obtained after encoding. Multiple methods for encoding, collection, and reconstruction as well as examples of the use of this novel imaging technique are disclosed. Furthermore, extensions of multirate modulator technique may provide some or all of the functionality of "image formation" directly supplanting or altogether eliminating the use of traditional image forming components such as lenses, mirrors, etc.

The novel imaging mode described in this invention works by modulating a spatially varying information I(x) in case of 1 D or I(x, y) in case of 2D with a multirate optical modulator such that intensity at each location x or (x, y) is multiplied by a unique, time-varying function $G_m(t)$. One may arrange for a one to one correspondence between m and coordinate $\hat{x}$ (where I use $\hat{x}$ to stand for both the 1D and the 2D case). The encoded image is reconstructed by simply applying the orthogonality conditions on the time-varying functions $G_m(t)$ using digital signal processing. In the preferred embodiment, all the functions $G_m(t)$ are simultaneously generated by a single monolithic optical modulator. I will provide considerable detail on practical methods for the operation of the encoder. I will also outline the theory of the operation of the preferred embodiment(s).

Let us directly investigate the simplest case of 1D imaging with a single detector that leads to an N-pixel reconstructed image. This will ease understanding extensions of the disclosed technique to the case of higher dimensions, different detector geometries, and reconstruction techniques.

Figure 1A:
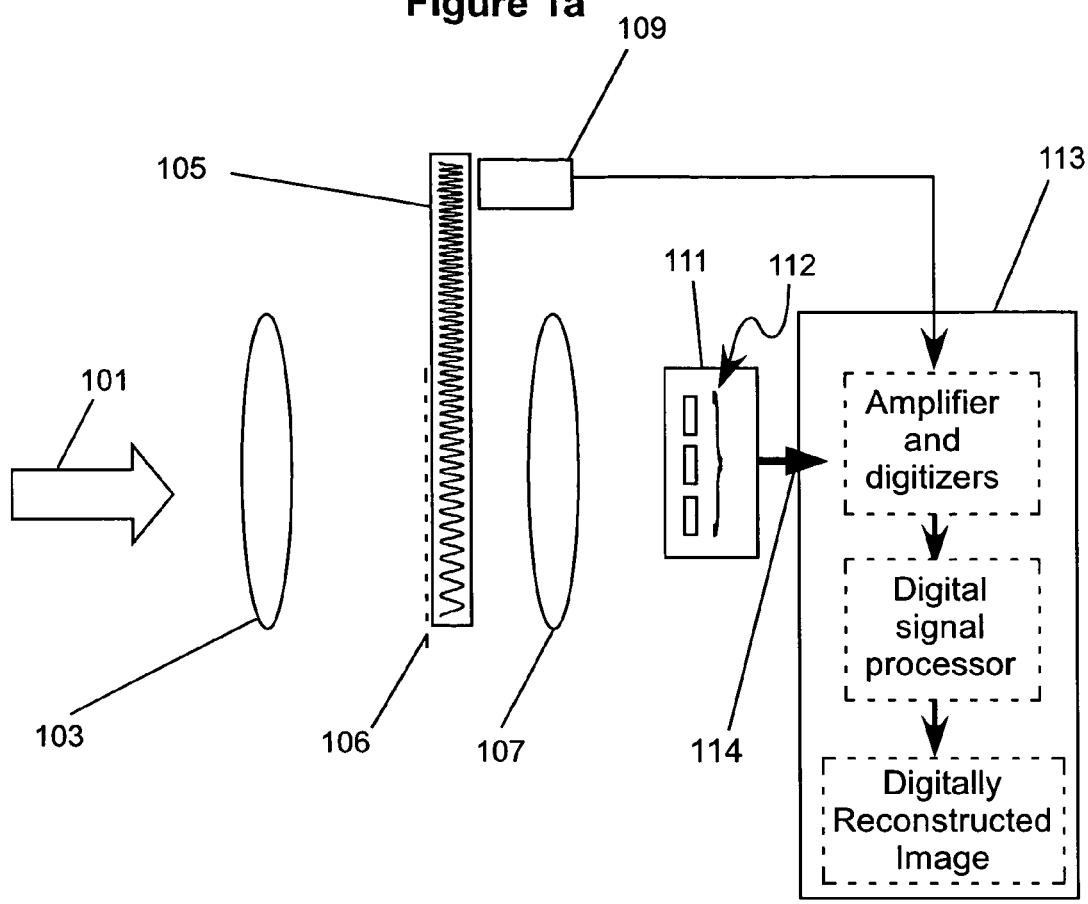
FIG. 1a is a schematic of the optically encoded imaging system.

FIG. 1a shows the schematic of the proposed imager. The input light beam or electromagnetic radiation incident on the apparatus is represented by 101. The incident EM radiation 101 is imaged by an imaging system 103 which may include simple lens, compound lens/miror system, diffractive optics, etc. This image is encoded by a multirate modulator 105 placed in the image plane 106. The image of the incident EM radiation is encoded using a set of functions as described by Equation 1. This dynamical encodings on may be applied to the amplitude, phase, wavelengths, polarizations, etc of the EM radiation. The radiation from the encoded image is collected by collection optics or the collection system 107 and detector system 111 which may consist of one or more individual detector elements 112. Optionally, the timing information from the multirate modulator 105 is generated by a timing generator unit 109. The timing generator unit may include photointerruptors, clock-recovery circuits, etc. Both the timing information and the dynamically encoded signal 114 from the detector system 111 are then signal conditioned, digitized, and processed by the electronic system 113 for reconstruction of the image or spatially varying data I($\hat{x}$).

Figure 1B:
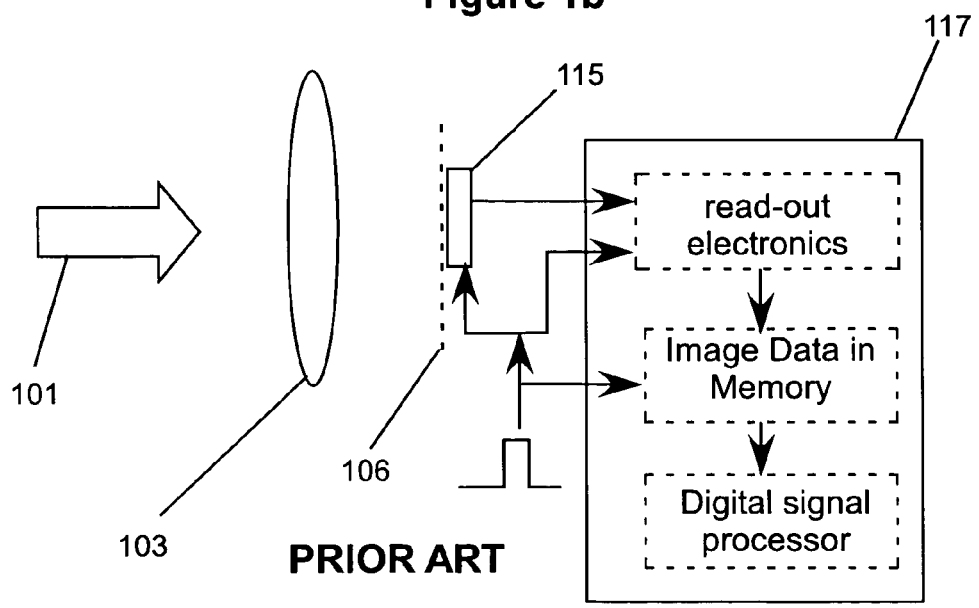
FIG. 1b is a schematic of prior art. It uses one- or two-dimensional shows pixelated array of detectors placed in the imaging plane.

Contrast this with a typical prior art shown in FIG. 1b. This type of imaging system is found in many scanners, digital imagers, etc. In both the FIGS. 1a and 1b, a conventional imaging system 103 forms an image in image plane 106. But in a traditional system, this image is converted to electronic information by directly placing a one or two dimensional focal plane array 115. The electronic signal from each pixel is transferred to memory for further processing by electronic system 117.

In FIG. 1a, the focal plane array 115 is replaced by multirate modulator 105, collection system 107, and the detector system 111. The physical equivalent of the summing operation in Equation 1 is carried out by the combination of collection optics 107 and the detector system 111. The individual detector elements 112 within the detector system 111 may be optimized for different spectral regions, different polarizations, etc. The dynamically encoded electronic signal 114 is read by the processing electronics. The image is then reconstructed from the dynamically encoded signal by using a reconstruction algorithm appropriate for the encoding generated by the multirate modulator. I will illustrate the operation of Optical encoding by a multirate modulator and reconstruction with a specifc case of a patterned rotating disk. Other methods of implementing multirate modulators described in this disclosure may be considered equivalent to the rotating disk in that they provide an ability to map the set of coding functions with indices m to the coordinates $\hat{x}$.

Figure 2:
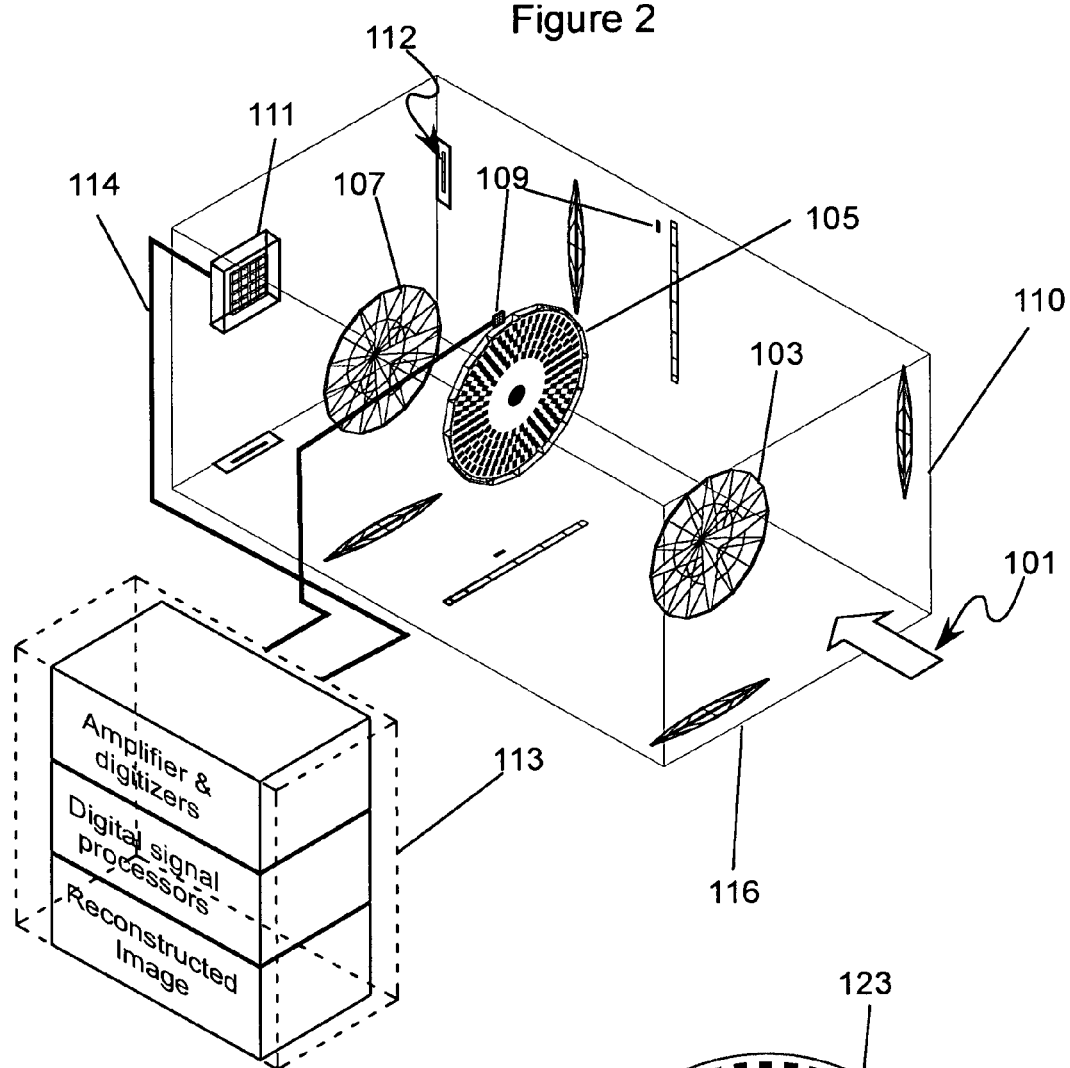
FIG. 2 is a perspective view of the optically encoded imaging system using rotating disk as a multirate modulator. The projections along different planes illustrate similarity between this figure and FIG. 1a FIG. 3 illustrates rotating disk multirate modulator with a pattern for 5 pixel 1D imager.

1 The patterned rotating disk: FIG. 2 shows the perspective drawing of the proposed imager schematically drawn in FIG. 1a. The projection planes 110 and 116 show the projection of the imaging system on each of the planes. A patterned rotating disk 119 is shown as an example of the multirate modulator 105. The discussion is initially based on one-dimensional imaging in order to develop all of the important concepts, so that one may generalize it to 2D imaging as well as "imaging" and reconstructing other information spaces such as spectra, polarization, etc. Other examples of multirate modulator 105 discussed for 1D imaging may also be generalized to 2D and other information spaces.

The rotating disk 119 is placed in the image plane and the line image 121 is placed at a certain distance from the center of the rotating disk. The line image 121 is shown in a particular orientation with respect to the disk but obviously many other orientations are possible that may be similarly analyzed. The light transmitted through the rotating disk (as shown in the figure but light reflected from a reflective pattern will do just as well) is collected by the light collection system 107 (shown as a single lens for illustration) and focused on a detector system 111. The collection system 107 may be designed to image or simply collect the modulated light on a detector system 111. A combination of the detector and the collection system should adequately collect the light from the dynamically encoded line image.

Figure 3:
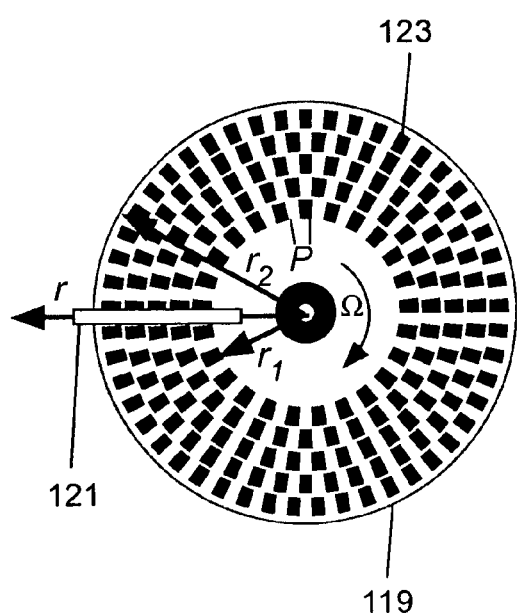

A typical disk pattern and position of the line image 121 is shown in FIG. 3. For clarity, FIG. 3 shows only 5 concentric rings, but in general the disk may consist of N-rings for reconstruction of an equivalent of N-pixel image. The mask pattern on the rotating disk 119 shown in FIG. 3 consists of a binary pattern for transmission. The binary transmission pattern may be created by metallizing the dark region 123 of the disk shown in FIG. 3. Manufacturing techniques for producing these and other patterns are discussed in Section 16.

Let us analyze the operation of the rotating disk and the encoding generated by the pattern shown in FIG. 3. The concentric rings on the disk are arranged to start at radius $r_1$ and are of width $\Delta r$. The actual period of the pattern P is kept constant, independent of the radius r. A simple mathematical condition exists for integer number of the periods to perfectly fit around the circumference:

$$2\pi r_m = mP, \qquad (2)$$

where m is an integer. As the disk rotates once, the line image 121 at any location $r_m$ is modulated m times. Different locations of the line image are modulated at different rates (corresponding to different m-values). Thus, each location $r_m$ on the image is modulated at a fundamental frequency given by $mf_{disk}$ where $f_{disk}$ is the rotational frequency of the disk.

Figure 4:
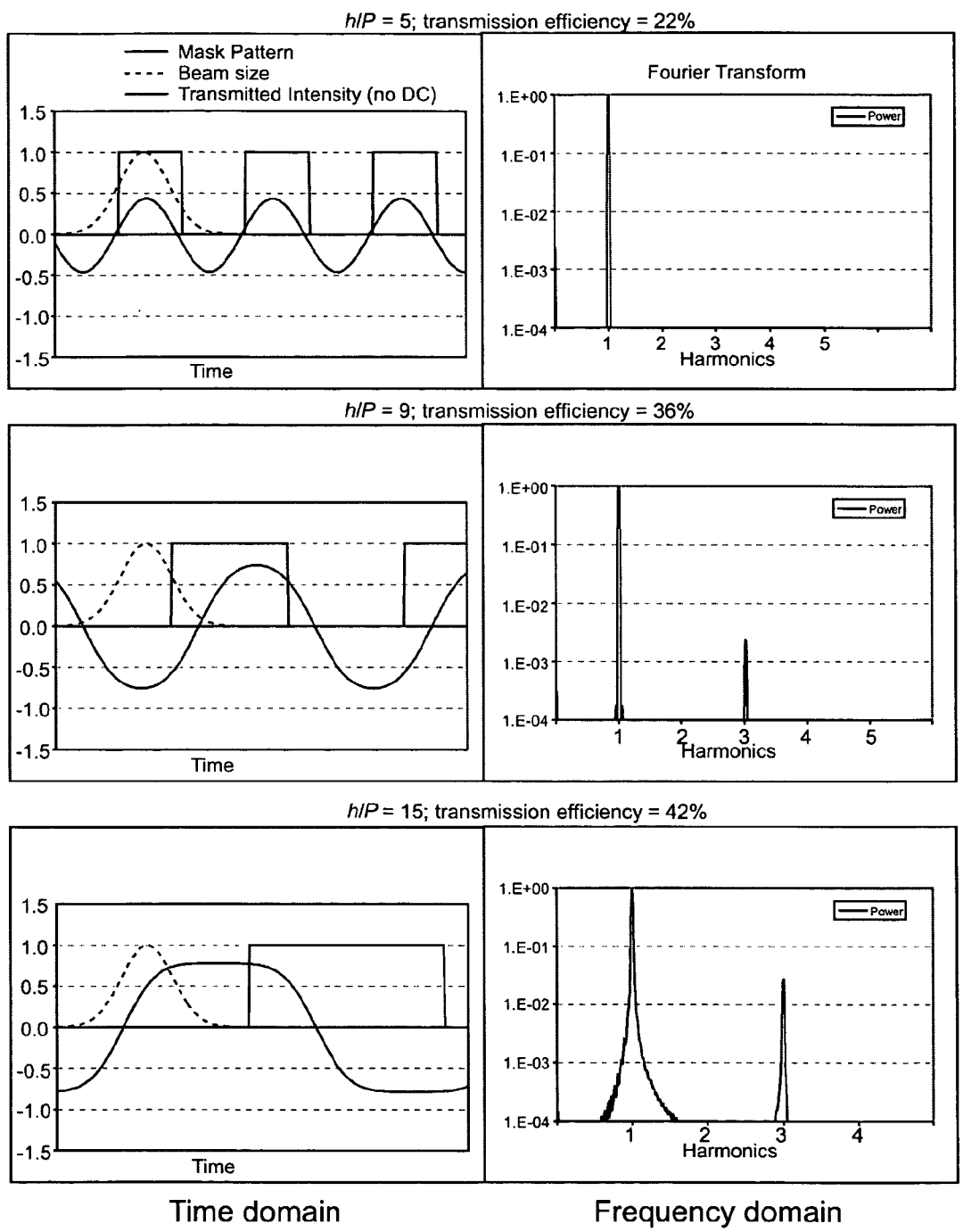
FIG. 4 shows the effect of the ratio of the pattern size to the image height on the transmitted intensity.

The actual shape of the transmitted light signal depends on the width h of the line-image compared to the period P. FIG. 4 shows the shape of the transmitted light as the ratio h/P is varied. For simplicity of analysis, I have assumed a Gaussian intensity distribution along the "h-direction" or tangential to the radial direction. FIG. 4 also shows the Fourier Transform of the time-domain signal. In each case, note the absence of the second harmonic. Also note the change in the third harmonic as a function of h/P. For a symmetric pattern, the second harmonic of the fundamental modulation frequency is automatically zero. If nonsymmetric patterns or encoding functions are used then there will be second harmonic components. Any deviation from the perfect sinusoidal shape (even if symmetric) gives rise to the third harmonic. The amplitude of the third harmonic relative to the fundamental approaches that for a square wave as the transmitted intensity pattern resembles a square shape. For clarity, the average or the DC light level has been subtracted from the graphs of the transmitted intensities in FIG. 4. In practice, it is likely that the detector may be AC coupled to the digitizer for the reconstruction and the DC level may either be unimportant or used for automatic gain control (see Section 3) etc. Each of the graph in the figure also shows the calculated transmission efficiency. For a perfect square wave transmission the efficiency approaches 50%.

In the example above, for a disk rotating at frequency $f_{disk}$, each location on the line image will be modulated at a different frequency. The fundamental modulation frequency $f_m \equiv f(r_m)$ at any radius $r_m$ is simply $$f(r_m) = m f_{disk}. \tag{3}$$

For practical reasons, the image may be restricted to the highest radius $r_2$ to be less than $3r_1$ in order to avoid the overlap of the fundamental frequency at one location with the third harmonic of the modulation from another location. An even more conservative criterion is to restrict $r_2 \leq 2r_1$ in order to avoid overlap with any second harmonics of the fundamental modulation frequencies. Furthermore, an electronic filter may be used to reject or suppress harmonics of the fundamental modulation frequencies. On the other hand, higher harmonics may be used in image reconstruction to improve effective light gathering efficiency.

An AC coupled detector receives a time-varying signal s(t) given by (ignoring higher harmonics and the DC light from transmitted optical intensity from the disk as well as an overall scaling factor for transmission efficiency), $$s(t) = \sum_{m=m_1}^{m_2} I(r_m) \cos(2\pi f_m t + \phi(m)). \tag{4}$$

Each location of the line image has been multiplied by a unique orthogonal special function (in this case by cosines). The image intensity may be recovered from the detector signal by Fourier analyzing the signal s(t). Any number of algorithms—from Fast Fourier Transforms (FFT), Discrete Cosine Transforms (DCT), to power spectrum estimations methods—may be used to extract $I(r_m) \equiv I(x)$ from the signal s(t).

2 Phase of the rings or the relative phase of the pattern: Each concentric ring may be given a different start phase $\phi(m)$ by simply starting the pattern with different starting angles on the disk. FIG. 5a and FIG. 5b show two disks with two different start phase maps. In FIG. 5a the start phases 125 are same while in FIG. 5b the start phases 127 are random. The corresponding FIGS. 5c and 5d show that the "spikyness" of the signal s(t) (calculated from addition of 50 rings) is determined by the phase map. A random starting phase map avoids spikes in s(t). Since the peak-to-peak amplitude plays a role in determining the limit on the number of pixels N that may be reconstructed using a detector with an n-bit ADC (see Section 9). Other phase maps such as a linear ramp may also accomplish the task of reducing the amplitude swings in s(t). The phasing of the pattern or in general the phasing in any multirate modulator may be used to reduce large amplitude variations in s(t).

In the discussion above, I have assumed that each ring corresponds to a single modulation frequency. This is accomplished by making the pattern period P, vary within the ring so as to be part of a "radial spoke" or subtending a constant angle $\theta_m$ at the center. This is illustrated in FIG. 6 in which single ring of rotating disk 119 is shown. If there were only one ring, then this radial pattern 129 would produce a single frequency independent of radius r. The condition in Equation 2 may be written in terms of angle as $$m\theta_m = 2\pi, \tag{5}$$

with index m taking integer values at predetermined various radii. This shows that if two radii were given the same m-value, the image at those locations will be modulated at the same frequency. This may be used to directly carry out image processing functions disclosed in Section 18.g.

3 Role of the DC light level: Equation 4 is a special case of a more general form of light modulation produced by the multirate modulator. This includes DC term as well as all of the higher harmonics. Retaining only the DC term and the fundamental modulation frequencies, $$s(t) = \sum_m I(r_m)[1 + \gamma \cos(2\pi f_m t + \phi(m))]. \tag{6}$$

The value of γ is fixed for a given pattern on the disk and the optical system. From Equation 6 it follows that one may use the DC light level measured by the same detector as a measure of overall light level which may control Automatic gain Control or AGC unit which in turn may be important in maintaining optimal signal to noise ratio (see Section 9).

4 How many unique frequencies may be assigned? This is the same question as—what is the maximum resolution? Since the condition in Equation 2 needs to be satisfied, one may have a new concentric ring whenever m changes by unity.

$$(\Delta m = s) \Rightarrow \Delta r = (sP)/(2\pi), \tag{7}$$

or the maximum number of resolvable elements per unit length are $(2\pi)/P$ for s=1. As an example, in the visible wavelength region, assume P of approximately 5 μm. This gives us a resolution of over 1200 pixels/mm. This applies only to integration time limited to one disk rotation. This is consistent with Equation 2 with "periodic boundary condition" or "seamless pattern".

In a general case, more complex patterns may be made on the disk where P is not constant throughout the disk but is varied in a systematic fashion depending on the choice of encoding functions. Choice of encoding functions determines the limit on the number of pixels that may be dynamically encoded.

A mask may be made such that in subsequent rings m changes by s (greater than equal to 1) and reduce the number of unique rings and lowers the resolution. Now, each pixel is encoded with a frequency separated by $sf_{disk}$. In this case, s(t) collected for time T given by $T \geq (sf_{disk})^{-1}$ is sufficient to separate the pixel data encoded in Equation 4. This follows from the well known properties of Fourier transforms. For s=1, s(t) is collected for the entire rotation of the disk in order to separate the modulation from each of the rings. For s=2, one may acquire two "frames" per rotation of the disk. The frame-rate for the line-scan camera based on the rotating disk depends on the rotation frequency of the disk and the skip factor s.

For a disk printed with the maximum resolution, i.e., a unique ring for s=1, the resolution may be "reduced" in software and frame rate increased, by appropriately reducing the data collection time T This comment is generally applicable to any multirate modulator in which orthogonal functions are used for image encoding.

5 Interleaved scanning: Depending on the skip factor s, the number of frames per rotation of the disk may be increased by s. This opens up the possibility of scanning sub-arrays. The disk may be divided into s-sectors, with each sector scanning only a portion of the linear image. As a result light from only N/s pixel subset is incident at a time on the detector. This is particularly useful for trading off dynamic range per pixel for a given bit-depth ADC converter (see next section for discussion). Note that the sub-arrays will be interdigitated with the skip factor s, so that frequency spacing of the pixels in any sub-array is $sf_{disk}$. This increased spacing is consistent with the requirement that these frequencies may still be resolved in the Fourier Transform taken over time $(sf_{disk})^{-1}$. The three rotating disks 131, 133, and 135 with s=1, 2, and 3 are illustrated in FIGS. 7*a*, 7*b*, and 7*c* respectively. These patterns correspond to the division of the original pattern on rotating disk 131 shown in FIG. 7*a* in two and three sectors respectively as shown in rotating disks 133 and 135, resulting in two and three interleaved subframes respectively. In the case of rotating disks shown in FIGS. 7*b* and 7*c* each sector (or sub-frames) produces a slightly different set of frequencies—the N-pixel, N-frequency disk pattern of disk 131 is masked sector by sector. It is also possible to have the same frequency assignment for each sector since they occupy different time slots. This can be accomplished by changing the period P in each sector in order to generate the same frequencies. An extreme case of subsector scanning is to scan a pixel at a time. This extreme case is very much like a traditional scanning with a single detector and the advantage of simultaneous acquisition of the N-pixel data is lost.

6 Phase-only gratings for modulation: For a given $f_{disk}$, larger modulation frequencies may be achieved by reducing P. Phase grating provides a convenient method to reduce P without reducing the "line width". A phase grating with period Λ and moving at velocity v induces a frequency shift Ω=v/Λ. This frequency shift may be converted to a modulated intensity by placing another matched stationary grating close to the moving grating or by interfering the frequency shifted beam with the original beam. The light is modulated at frequency Ω. In the case of a matched grating pair, one moving and one stationary, the period of one modulation is equal to the time it takes to pass one half of the grating pitch and thus the modulation frequency is doubled compared to the frequency of the travelling wave. The system of matched grating pair is achromatic and the modulation frequency is not a function of the wavelength. The advantage of this method over a direct intensity mask is its potential to reach higher modulation frequencies. For example, one may use a phase grating with a grating pitch of 1 micron in the visible while keeping P=100 microns for the amplitude mask. The amplitude modulation will produce "side-bands" on the "carrier" modulation frequency produced by the phase grating. This may allows us to pick the frequency of modulation, independent of the physical pixel size. The phase gratings may provide close to 100% light throughput and allow us to collect the two complementary (in-phase and out-of-phase) signals similar to the case of the outputs of a scanned Mach-Zhander interferometer) signals. A complex encoding of the image is now possible by encoding data in both phase and amplitude. This is useful in many cases. Some of the examples include coherent radiation based reconstruction (Section 18.h) and range detection (Section 11).

7 Grayscale coding and built-in window functions: In many cases, the signal s(t) is multiplied by an appropriately chosen window function. This is often used to reduce the "leakage" between the spectral components when taking the FFT or other appropriate transforms depending on the pattern. This windowing may be "coded" on the disk itself by varying the transmission through the disk as it rotates. This may avoid extra computation needed for applying window function. It may be accomplished by using either a grayscale lithography techniques, or by bonding another disk with a fixed grayscale profile to the binary mask. These sorts of grayscale disks may be used to make smooth transition from one sub-array to another as commented in Section 5.

8 Algorithms: Many algorithms have been developed over the years to extract the Fourier components of the signal. I have found that many of these algorithms work adequately. One efficient method may be to use complex Fast Fourier Transform (FFT) for real-valued data. I used the algorithm outlined in Numerical Recipes. Another possibility is to simply find the power spectrum of the signal if the interest is only in the amplitude factors $I(r_m)$. The phases $\phi(m)$ become important for applications such as depth imaging or range detection, ellipsometry, and time-domain fluorescence. Direct lock-in techniques or FFT may be used to recover the phase of individual modulated signals.

Figure 8:
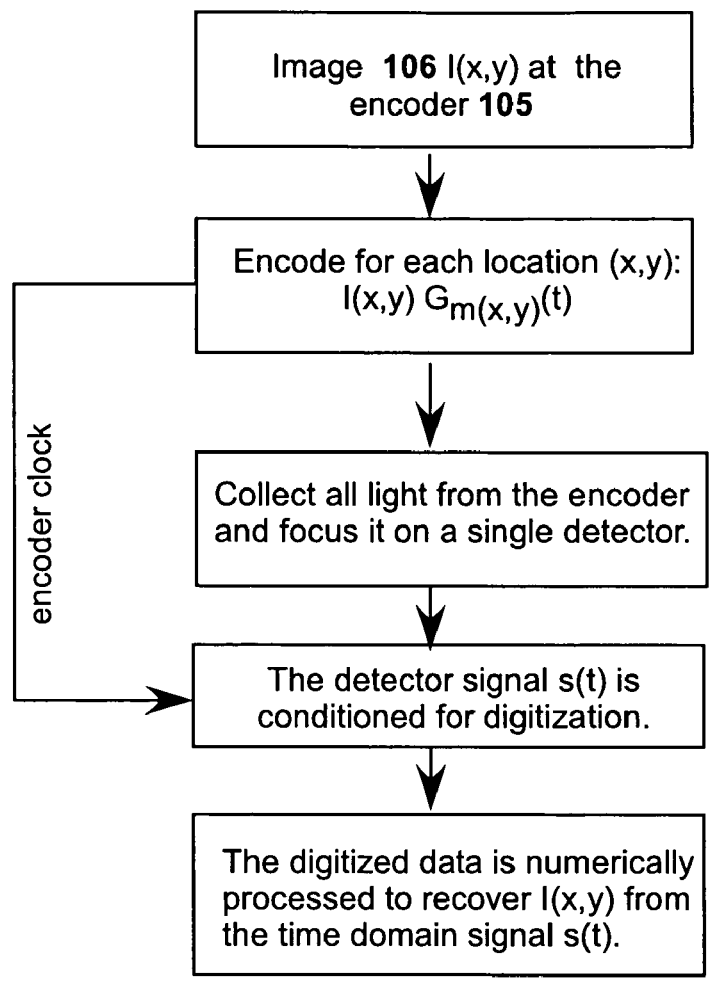
FIG. 8 is a flow diagram of the optically encoded imaging system.
Figure 8:
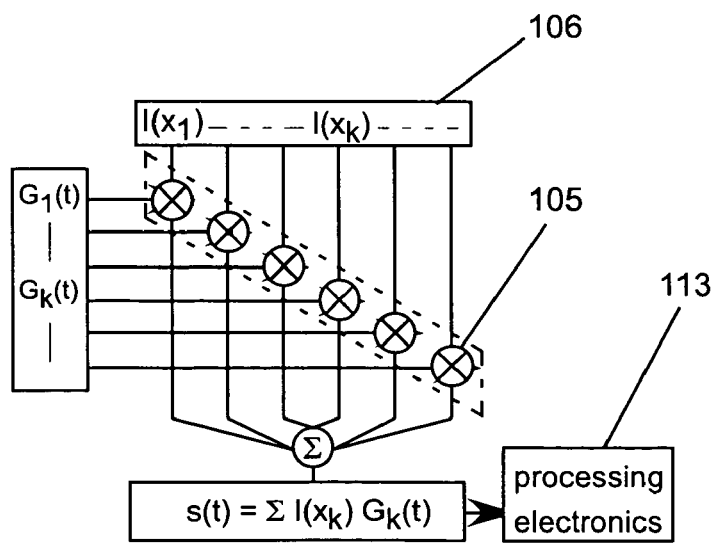

The flow chart for imaging using a multirate modulator based optical encoding and reconstruction is shown in FIG. 8.

9 Limitations on N from the Bit-Depth of a Single Analog-to-Digital Converter (ADC).

In previous embodiments, the image is encoded by a rotating disk. In principle, the resolution may rival a photographic film. In this section, I show that a relationship exists between the number of pixels, dynamic range of each pixel and the bit-depth of ADC. Let us see how the bit-depth of ADC (I am assuming that this is the controlling factor in determining the dynamic range in the digitization process and is not limited by the detector) affects the practical pixel number N. If all pixels were carrying full light intensity, then there will be N-units of light on the detector at some point in time for a disk in which all phases start together as captured by the spikes in the signal in FIG. 4*c*. One may arrange signal conditioning electronics such that the N-units of light on the detector correspond to the maximum voltage for the n-bit ADC. This may be achieved in practice by using AGC on the signal before applying it to the ADC. If each reconstructed pixel has a dynamic range of $2^{n_0}$, then one needs an ADC with bit depth n such that $2^n \geq N2^{n_0}$. For random start phases as shown in FIG. 4*b*, the peak in the signal is approximately $\sqrt{N}$. In this case, the ADC requirement is approximately $2^n \geq \sqrt{N}2^{n_0}$. Therefore, for a given ADC converter, a greater dynamic range may be achieved by using appropriate phase patterns to reduce "spikyness" in the time-domain signal.

Let us take some practical examples. Assume an 8-bit dynamic range per reconstructed pixel while using a 14-bit ADC. For $n_0=8$ and $n=14$, the two cases corresponding to the phase maps of FIGS. 4a and 4b give us maximum N of approximately 64 and 4096 respectively. For $n_0=7$, which may be adequate for many applications, one has a maximum N of approximately 128 and 16,000 respectively.

Figure 9A:
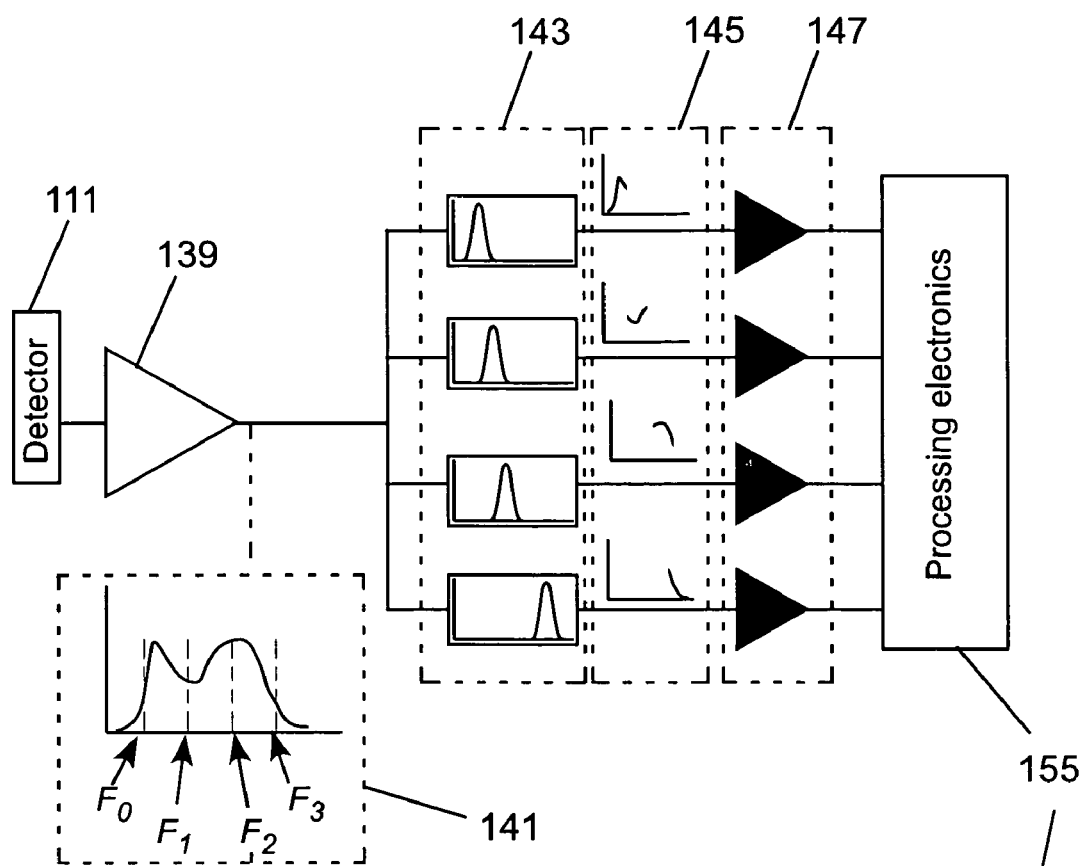
FIG. 9a shows multiple Analog to digital converter to increase dynamic range with each digitizing separate spectral regions.
Figure 9B:
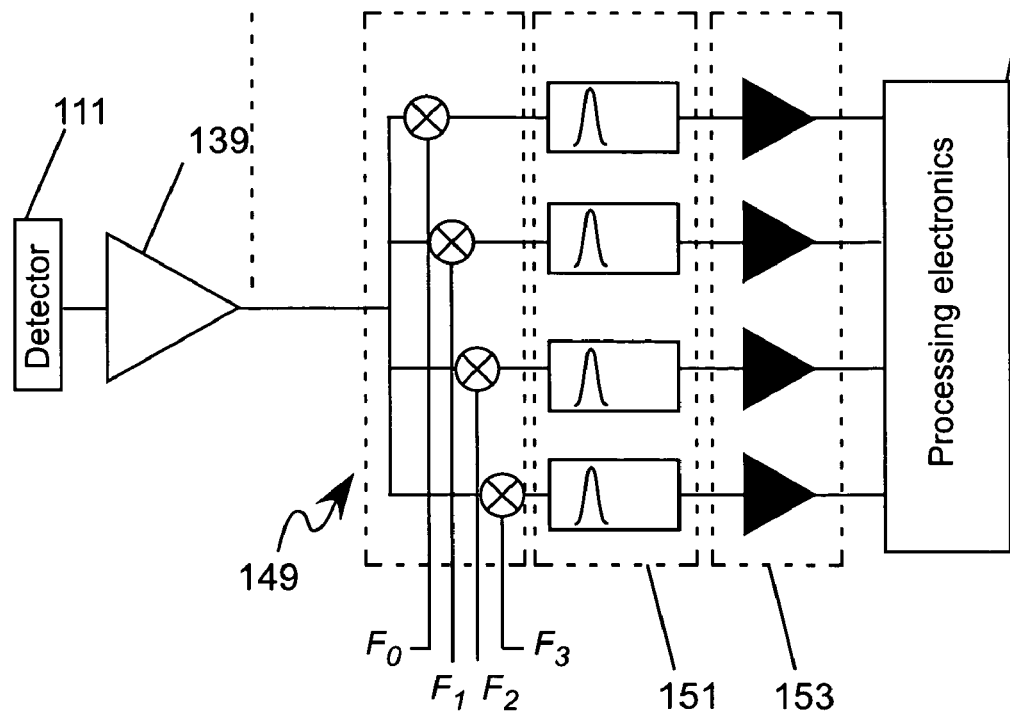
FIG. 9b also show multiple Analog to digital converter to increase dynamic range. In contrast to FIG. 9a, each converter is operating with the same band pass filter because each region of the signal spectrum has been translated by mixing.

Improvement in the dynamic range may be accomplished by many techniques used by the designers of modern ADCs such as oversampling. One may also employ other electronic methods to improve total available dynamic range. Assuming that signal to noise ratio or the dynamic range is not limited by the detector, multiple ADC's may be employed to digitize different parts of the signal spectrum s(t). Two examples that use multiple ADC's are illustrated in FIGS. 9a and 9b. In FIG. 9a, the signal from the detector system 111 is amplified and conditioned by electronics 139. The spectrum of the dynamically encoded electronic signal is shown as 141. The idea is to divide the signal spectrum into multiple spectral regions, with each spectral region (with corresponding image region) assigned to a particular ADC, which may improve the total available dynamic range. The signal from the electronics 139 is bandpassed by a bank of filters 143 with each having a different center frequency. The different frequency regions are then digitized by a bank of ADC converters 147. In FIG. 9b, the spectrum of the signal 141 is passed through a bank of mixers 149 so that the output from the mixers may be selected by a bank of band pass filters 151 which are all identical. In this case, each ADC in the ADC bank 153 may be operated at a lower frequency compared to the total spectral bandwidth of the original signal. In each case, the output from the ADC banks 147 or 153 is sent to a digital signal processing unit 155 for reconstruction of the entire data. Use of multiple ADC channels may also provide another advantage for optimizing dynamic range. The rms or the average output from each of the filter banks may be used set the AGC values for each of the filtered outputs. These outputs may be either combined and processed by a single ADC or multiple ADCs. The values of the AGCs may be read by a digital signal processor and the final image may be reconstructed with a much higher dynamic range than is possible with a single gain setting for the entire image. This feature may find use in avoiding "blooming" and darkening of the entire frame from the saturation of a few pixels—a common issue with traditional serial readout devices such as CCD or CMOS imaging arrays.

Clearly, the improvement in dynamic range may also be achieved by using extra detector systems 111 such that each detector system receives different parts of the dynamically encoded image. The multiple regions are combined and the image reconstructed by the digital signal processing system such as 155.

Dynamic range may also be improved by use of nonlinear signal amplification in which intensity dependent bit-depth is provided. (Many audio digitizers use such nonlinear gain elements to improve the perceived bit-depth). This type of method becomes possible due to mapping of the spatial data into the time/frequency domain by the multirate modulator. A nonlinear transformation of the signal from the detector may amplify small signals much more than a strong signal before digitizing. Inverse transformation may be performed in the digital domain to improve the signal to noise ratio and improve the dynamic range. Some of these techniques are extensively used in acoustics and common nonlinear transformations such as "mu-law" or an "A-law" are used in audio digitization. More generally, the dynamic range per reconstructed pixel will always be lower than the dynamic range of the ADC converter digitizing a single pixel.

10 Very rapid changes in the intensity of pixels: In a conventional camera, very rapid changes in the intensity of the image (faster than the frame rate) are either aliased or averaged out. The imager based on the dynamic encoding by a multirate modulator can allow those rapid changes to be tracked if needed. This may be accomplished by increasing the bandwidth of the detector and the digitizer or using two sets of detectors—a high speed detector for measuring rapid changes and a lower speed detector for image reconstruction for the normal operation of the imager. Since the signal from the detector is bandpass filtered in the normal operation of the imager, aliasing is avoided.

11 Depth imaging or range detection: The start phases of Equation 4 have served a purpose of scrambling the intensities from each pixel in order to maximize the use of the available ADC dynamic range as discussed above. There is another very important role for the phases. When combined with a reference detector, it provides the measure of "delay" or light travel time. Depending on the application, this delay may be interpreted as a birefringent phase shift, depth, decay time of a fluorescent signal, response time etc. Below I disclose a technique for measuring the phase of the dynamically encoded light and apply it to the specific case of measuring the distance of the object at location x in the reconstructed image.

Figure 10:
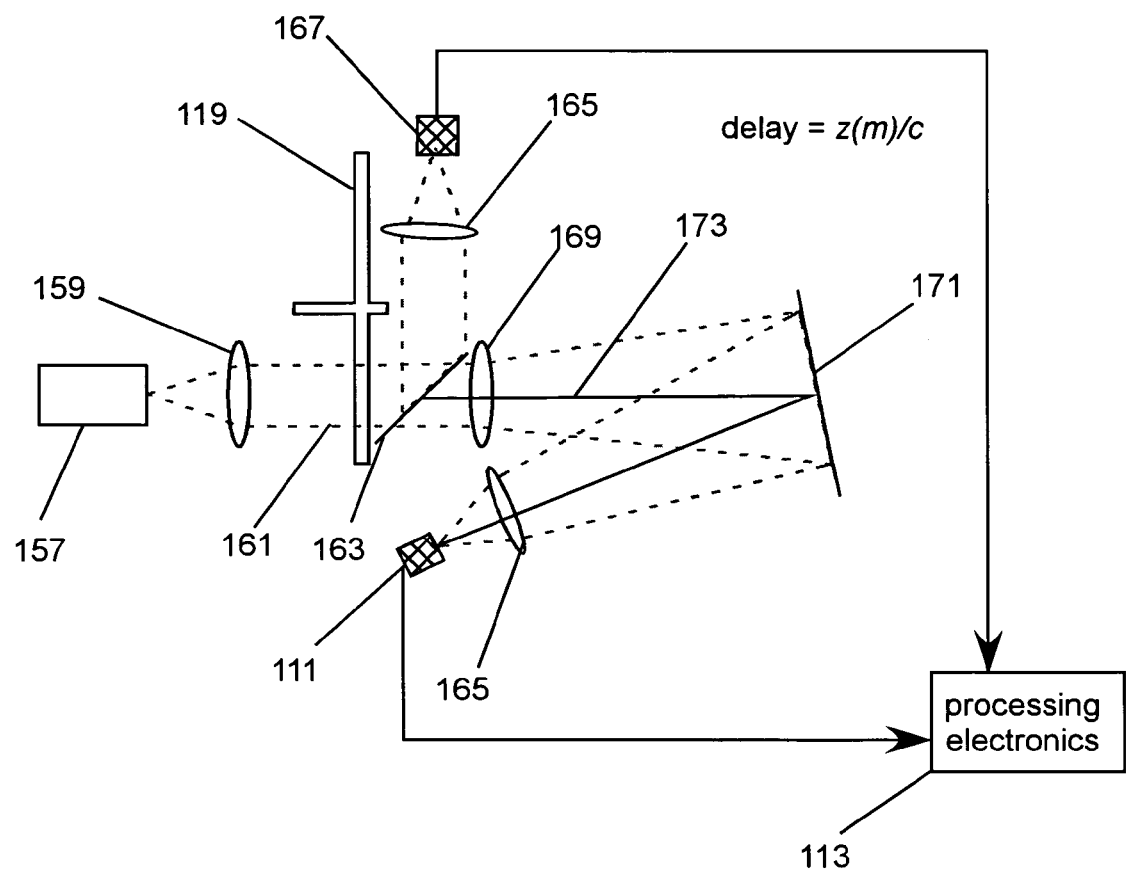
FIG. 10 is a schematic of a system for measuring the range of the object from the source.

First let us note that the system shown in FIG. 1a may also be used with an encoded light beam. In this case, the illumination light beam is encoded by rotating disk 119 or some other multirate modulator 105 and use it to illuminate the object as shown in FIG. 10. The illumination light beam 161 from the light source 157 is imaged by the imaging system 159 on the rotating disk 119. A small fraction of the dynamically encoded light beam is used to generate the reference signal by splitting it with a beam splitter 163. The reference signal is collected by lens system 165 on to the reference detector 167. The dynamically encoded light beam is then projected on the object by the projection system 169. The light scattered from the object 171 is collected by the lens system 165 on the main detector 111. The difference between this and case in FIG. 1a is that the light is encoded before illuminating the object as opposed to encoding it after imaging. Note that in this case, scattered light from the object at location x has a modulation frequency map determined by the multirate modulator. Reference signal $s_{ref}(t)$ is given by $$s_{ref}(t) = \sum_m l(r_m)\cos(2\pi f_m t + \phi(m)), \quad (8)$$

where $l(r_m)$ is the intensity envelope of the illuminating light source. After scattering from the object, the intensity at the detector is $$s(t) = \sum_m l(r_m)I(x_m)\cos(2\pi f_m t + \phi(m) + \delta\phi(m)), \quad (9)$$

where $I(x_m)$ represents the object 171's light scattering function or its reflectivity. The projection optics determines the mapping between a location on the rotating disk and a location on the object that correspond to the same function index m. The term $\delta\phi(m) \equiv \delta\phi(x_m)$ corresponds to the time of flight of light from the reference detector 167 near the rotating disk 119 to the main detector by scattering off the object. For range measurement, $$\delta\phi(x_m) = f_m(z(x_m)/c), \quad (10)$$

where c is the velocity of light, and $z(x_m)$ is the total distance from the rotating disk (near the illumination source) to the object, and from the object to the main detector. From the above equation, it directly follows that the measurement of the relative phase shift between the reference detector and the main detector corresponds to the "depth" or distance to the object. In this sense, the line image camera may be deployed to measure the 1D/2D image along with the distance to the object to become a depth-resolved imager.

Many numerical methods are available to measure the relative phase. Examples include complex FFT and digital lock-in algorithms, as well as phase-lock loops. Different algorithms produce different amounts of phase noise $\delta\phi$. $\delta\phi$ also depends on the bit-depth of the ADC and the integration time T. The minimum detectable change in the z(x) is given by $$\delta z = (\delta\phi/f_m)c. \quad (11)$$

Table below summarizes values of $\delta z$ for various possible value of $f_m$ and $\delta\phi$.

|             | $\delta\phi$ in degrees |       |       |
| ----------- | ----- | ----- | ----- |
| $f_m$ in MHz | 1     | 0.1   | 0.01  |
| 1           | 5236  | 523.6 | 52.4  |
| 10          | 523.6 | 52.4  | 5.2   |
| 1000        | 5.2   | 0.5   | 0.05  |

In Section 18.i, I disclose methods that lead to higher modulation frequencies than rotating disks. It may be possible to reach 1 GHz or greater modulation frequencies and improve range resolution.

Figures 11A, 11B, 11C:
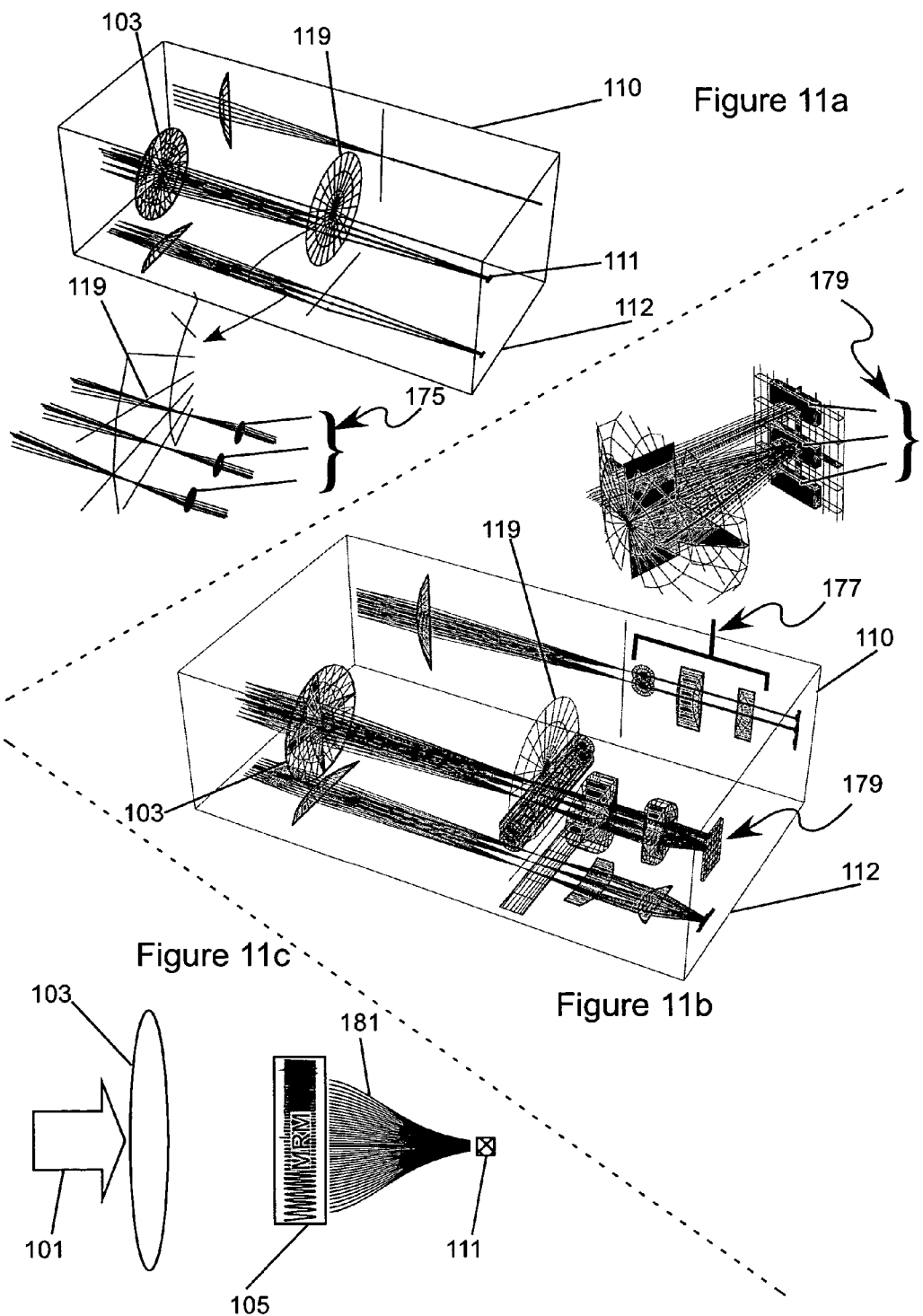
FIGS. 11a, b, and c show three designs for collecting encoded light on a detector system.

12 Light collection system and size of the detector: The technique described above requires that the modulated light leaving the imaging plane be collected by a detector system 111. For efficient collection of the encoded light, one needs an optical system that may include lenses, waveguides, and a few small detector elements 112 that are electronically connected to act like a single larger detector system 111 that provides signal s(t) to processing system 113. The main challenge is to "re-image" the encoded image by the multirate modulator on a relatively small detector. The reason for using a relatively small detector is generally for low-noise and high-speed. This is because, quite generally, the detector capacitance scales as detector area and the intrinsic detector noise scales as the square root of the detector area. This is one of the reason why it is important to be able to design collection optics that are efficient in collecting the encoded light on a small detector. This may be accomplished in many ways. Some of the methods are shown in FIGS. 11*a*, 11*b*, and 11*c*. FIG. 11*a* shows a 1D or 2D lenslet array 175 positioned behind a rotating disk 119 to collect light. It is also possible to use a combination of diffractive and refractive lenses that optimally direct light to a detector system 111. FIG. 11*b* shows a collection system 177. It comprises of a cylindrical or pipe lens (or an array in case of 2D) to first reduce divergence along one direction followed by a simpler optical system comprising of a single lens or a multiple lenses to collect light on the detector system. As an example, I have shown the detector system made from rectangular detector elements 179. The rectangular elements may make it easier to design collection system 177 for efficient collection of dynamically encoded light. In case of 2D imaging, each of the detector elements 179 is configured to act as a detector system 111 producing dynamically encoded electronic signal (such as 114) for one dimension of the image (say radial as shown in the FIG. 11*b*). By combining signals from the array, a 2D image is reconstructed. FIG. 11*c* shows a set of waveguides or waveguide bundle(s) 181. A waveguide bundle may be tapered to improve light collection efficiency on a smaller detector element.

13 Other methods of multirate, dynamic encoding of the image: Below are other embodiments of the multirate modulator which are different from the rotating disk 119 described above. I will simply illustrate how the encoding works and the care that needs to be taken for a specific case. The basic theory of operation and set of principles discussed above remain unchanged.

Figure 12A:
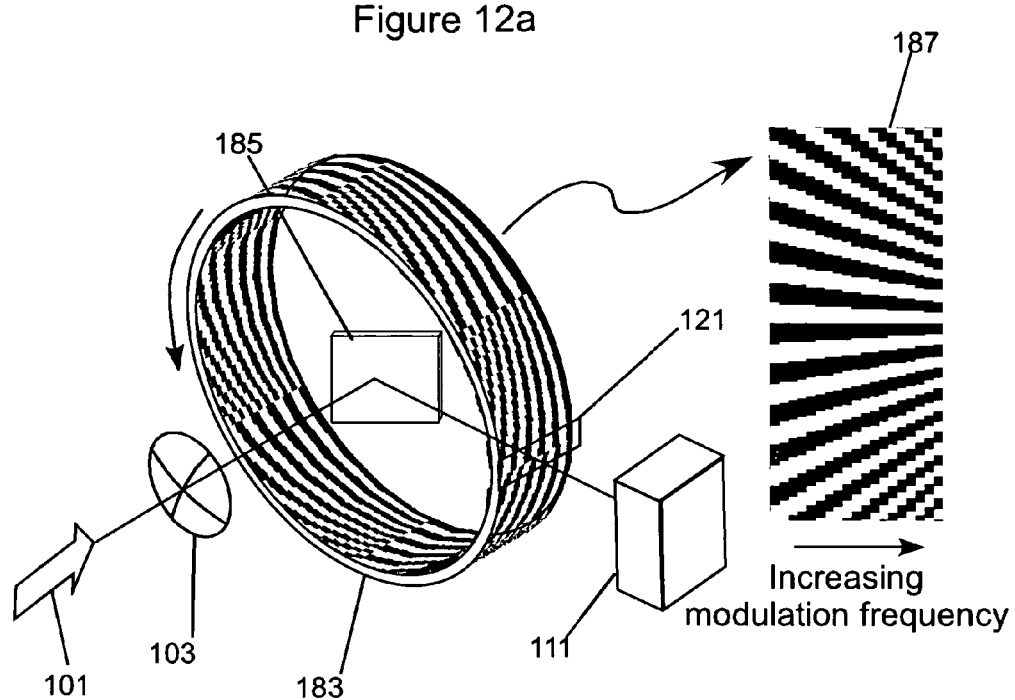
FIGS. 12a and 12b show two multirate modulators based on cylindrical geometry.

13.a Patterned Cylinder: The basic principle is shown in FIG. 12*a*. Collection optics 107 and the detector system 111 are not shown in this figure for clarity. A patterned cylindrical modulator 183 is used as an example of multirate modulator. Since the velocity is constant along the image line or x-direction in FIGS. 12*a* and 12*b*, one needs to choose the pattern such that different locations along the line image correspond to different modulation frequencies. If R is the radius of the cylinder then one must pick period P to vary along the x-direction such that $P(x_m) = (2\pi R)/m$. Such a pattern leads to modulation that varies along x-direction with frequencies given by $f(x_m) \equiv f_m = mf_{cyl}$.

Figure 12B:
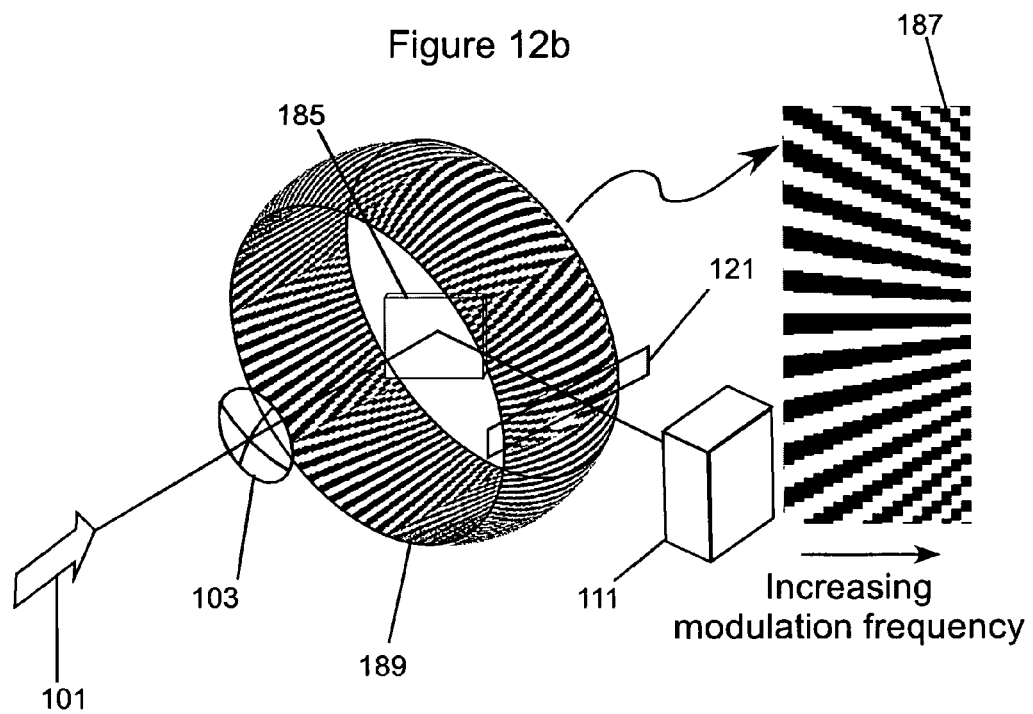

The case outlined here can be generalized to a curved cylindrical multirate modulator 189 shown in FIG. 12*b*. The cylindrical multirate modulator 189 is curved to "fit" the shape of the image-plane or the curvature of the image. This may reduce the requirement on the image forming optics for a distortion-free, achromatic image. This is an example of ability of the disclosed imager to conform to the "curved" image plane while still using a planar detector element 112 in a detector system 111. Application examples are discussed in Section 18.m.

13.b Rotating pattern of light and dark lines: FIG. 13*a* shows rotating disk with a linear grating pattern 191. The rotation of this pattern is shown in FIG. 13*c*. This disk produces a signal on the detector for any location (x, y) on the disk as, $$s(x,y;t) = \sin[(2\pi/\Lambda)(x\cos(2\pi f_{disk}t) + y\sin(2\pi f_{disk}t))]. \quad (12)$$

FIG. 13*b* shows the temporal pattern produced at various x with y=0 corresponding to the snap shots of rotations shown in FIG. 13*c*.

FIG. 13*b* also shows that the modulation frequency increases with the distance from the center of the disk in a linear fashion over a narrow window in time 192. This linear frequency map region is identified in the FIG. 13*d*. One may use the data from these narrow windows in time to reconstruct the image by using the methods identified in the previous section. This is because the frequency maps in these time windows are similar to the frequency map produced by the rotating disk shown in FIG. 3.

The entire data set shown in FIG. 13b may also be used for image reconstruction. This may be accomplished by "locking" the ADC clock to the zero-crossings of a photo-interrupter (as an example of timing generator unit 109 in FIG. 1a) placed at a radius $r_l > 2r_2 \equiv \Gamma r_2$. The signal $$g(t)=\sin[(2\pi/\Lambda)(r_l \cos(2\pi f_{disk} t))] \quad (13)$$

from a small light spot of the photo-interrupter at $r_l$ may be deduced from Equation 12 by setting $x=r_l$ and $y=0$. In a single rotation of the disk, the zero-crossings of g(t) occur at times $t_k$ whenever $$(2\pi/\Lambda)(r_l \cos(2\pi f_{disk} t_k))=k\pi, \text{ with } k=0, 1, \ldots k_{max} \quad (14)$$

where k is an integer. For a single rotation of the disk, one can show that $k_{max} \approx (2r_l)/\Lambda$. Since the ADC clock is locked to the zero-crossings, the samples are taken at times $t_k$. The data produced from Equation 12 with samples taken at times $t_k$ is given by $$s(x, y; k) = \sin\left[(x/r_l)k\pi + (y/r_l)\pi\left(\sqrt{(2r_l/\Lambda)^2 - k^2}\right)\right]. \quad (15)$$

For a image placed from $x=x_1$ to $x=x_2=2x_1$ and at $y=0$, one has a very simple relation $$s(x, 0;k)=\sin[(x/r_l)k\pi]. \quad (16)$$

The above equation illustrates that for the digitized data, the "sampled frequency" is a linear function of x and is given by $f(x)=x/(2r_l)$. In this embodiment, I have shown that a simple, easily available "amplitude grating" of FIG. 13a may be adapted for use as a multirate modulator.

In the above analysis, I have assumed that the extent in the y-direction is narrow compared to the period $\Lambda$. Below, I show an example analysis with a normalized Gaussian profile in the y-direction, $(1/(\sqrt{2\pi}h))\exp(-(y^2/2h^2))$, where h represents the height of the line image. For such a line image placed at location $y_0$, Equation 12 (after integrating with respect to y) gives, $$s(x,y_0;t)=\exp(-(\frac{1}{2})((2\pi/\Lambda)h \sin(\omega_d t))^2)\sin((2\pi/\Lambda)(x \cos(\omega_d t)+y_0 \sin(\omega_d t))), \quad (17)$$

where I have written $\omega_d=2\pi f_{disk}$. The exponential factor in the front shows that if the extent of the line image $h>\Lambda$, then the response is suppressed. This is because the image at any location cannot be completely masked by the pattern when $h>\Lambda$. For $h<\Lambda$, the exponential factor slowly modulates the envelope because the entire image is blocked whenever the lines on the rotating disk are aligned along the x-axis—twice per rotation.

Note that the image may be placed at any location along y. The frequency chirp produced by the y dependent term in Equation 15 may be incorporated in the algorithm for reconstruction. As discussed in Section 17.c, the frequency chirp in the y direction may be used to reconstruct a 2D image with a single disk.

13.c Oscillating disk or sinusoidally oscillating multirate modulator: FIG. 14a shows a sector or a portion 195 of a rotating disk 119. It is mounted on an oscillating cantilever or a membrane. The cantilever may be made to oscillate using many well-known techniques such as voice-coil actuators, electrically driven (resonant) tuning fork, oscillating scanner etc.

If the oscillation is described by $\theta(t)=\theta_0 \sin(2\pi f_o t)$, then the modulation frequency for pattern in sector 195 at a location $r_m$ from the center is, $$f(r_m, t)=(r_m f_o \theta_0/P)\cos(2\pi f_o t). \quad (18)$$

The variation of frequency as a function of time at a few locations $r_m$ is shown in FIG. 14b. This is a case where the map of encodig functions changes with time. The actual transmitted light signal (assuming constant starting phase but may be generalized to any function for starting phases) is given by $$s_m(t)=\sin(2\pi[f_m(r_m, t)]t). \quad (19)$$

Contrast this with the case of a rotating disk 119 shown in FIG. 3, where frequency map remains invariant, making the reconstruction very simple. This map is similar to the rotating grating of Section 13.b. Some of the reasons for choosing this method for multirate modulator may include: (a) it is possible to reach very high modulation frequencies, (b) the multirate modulator may be made compact using micromechanical structures, and (c) low-power consumption by providing resonant oscillations. Below, I mention three possibilities among many that allow us to recover the image using oscillating structures.

In FIG. 14b, there is a a narrow slice of time identified as region 193 in which the frequency map is substantially constant. Collect and analyze data only during this time. Now one may use image reconstruction algorithms developed for rotating disk. The usable time window may be determined by noting that the frequency map may not change by more than a small fraction of the frequency separation.

FIG. 14c shows a more complex mask pattern on sector 197 so that the pattern period P is itself made to vary along the direction of oscillation θ to compensate for the sinusoidal variation in time of the frequency map. The mask pattern of sector 197 is given by, $$P(\theta)=P\sqrt{1-(\theta/\theta_0)^2} \quad (20)$$

This increases the usable fraction of time when the frequency map is substantially constant. Since the period tends to zero at the extremes, the transmission decreases, and the mask pattern of sector 197 also acts as a natural window function. It extends the time window 193 by a factor of 2-5 compared to the mask pattern on sector 195.

As discussed earlier in Section 13.b, one may lock the ADC clock to the zero-crossings of the transmitted amplitude derived from the oscillating sector 195. As a specific example, clock signal is derived from the disk pattern at a distance $r_l > r_2 \equiv \Gamma r_2$. Equation 23 shows that zero-crossings occur whenever (without regard to the sign of slope), $$2\pi[(r_l f_o \theta_0/P)\cos(2\pi f_o t_k)]t_k=k\pi, \quad (21)$$

where k is an integer. If the sample is acquired at only times $t_k$ then the signal $s_m(t_k)$ from any particular location $r_m$ will have values given by, $$s_m(k)=\sin(2\pi[f_m(r_m, t_k)]t_k)=\sin(2\pi[((r_m f_o \theta_0)/p)\cos(2\pi f_o t_k)]t_k)=\sin(2\pi(r_m/2r_l)) \quad (22)$$

The sampled signal is assigned a simple sinusoidal function with the new effective frequency given by $f_m = r_m/2r_{clk}$, with the index k playing the role of time. In this way, the time-dependent frequency map has been converted to the invariant frequency map and algorithms discussed for the rotating disk may be applied.

13.d Oscillating cantilever, fixed mask screen: In the cases discussed previously, the mask is moving with respect to a fixed image or a source. The same principle of the dynamic encoding of the image/source may be used when the source/image are made to move against a fixed mask. The motion of the image/source can be generated relative to that of a mask by oscillating the image relative to a fixed mask. Vibrations may be caused by a mirror mounted on a Galvanometer or an electrically driven tuning fork etc. In many cases, the motion of the source/image is not preferable. A double pass geometry may be used in which the light is passed twice through the mask and again reflected from the same oscillating mirror with slight misalignment so as to separate the incoming and the outgoing modulated light beams. The double pass naturally removes the motion of the vibrating beam (after modulation) so that it may be used to illuminate an object (source modulation) or fixed collection optics (image modulation).

One particular advantage among others of this method is that both d (the distance form the vibrating mirror to the mask) and the cantilever frequency may be made quite large which may allow modulation frequency to be in the multi-MHz range. For example, with $f_0=100$ kHz, $\theta_0=1$ degree, $P=10$ μm and $d=100$ cm, one has a base modulation frequency of 175 MHz. A mask for 1D encoding of the source is shown as 199 in FIG. 15. This chirped pattern provides a frequency map similar to the case discussed for cylindrical multirate modulator. Another possibility for providing different modulation frequencies is to tilt the mask such that distance d is different for each of the locations on the mask with the caution that the beam remains in focus on the tilted mask.

These high resonant frequencies may be achieved with many micro-machined mechanical structures. The large d may be realized in practice by folding the beam path using mirrors or a glass slab with multiple total internal reflections. Note also, that an optical system may also be used to magnify the angular deviation (which is what a telescope does).

13.e Other modulation methods: So far I have considered methods that use a mask pattern and a relative motion of the optical beam with respect to the mask to impose (or map) a multirate modulation simultaneously. This is very economical because only one part has to move and the actual frequency map is determined by the mask. Since masks can be made with great precision, relative precision and accuracy of the frequency map can be quite good. Other electronically programmable examples of multirate modulator are given in the following paragraphs.

Acousto-optic or electro-optic modulators are capable of providing extremely large frequencies of modulations. This is because it is easy to move a "mass-less" optical beam at high-frequencies than moving a physical mask. One may employ these modulators instead of mechanical deflectors to implement the multirate modulation. Also, the some of the modulators listed below provide programmable multirate modulators.

13.e.1 Acousto-optic modulators: Acousto-optic modulators (AOM) have the capability to provide a frequency map analogous to a rotating disk. A frequency chirped travelling acoustic wave will provide different modulation frequencies at different locations. Of course, the frequency map will change as a function of time due to the travelling nature of the acoustic waves. This change may be taken into account in the analysis of the digitized signal. Physically similar situation of travelling chirped amplitude mask (AOM provides a phase-mask but ultimately one converts phase-shifts to intensity for detection) has been analyzed in Section 17.d, in which I show that the moving, chirped pattern that repeats periodically may be analyzed to reconstruct the encoded image data. One of the advantage of AOM is that the frequency map may be programmed by simply updating the function generator responsible for providing the RF waveform.

13.e.2 Micro mechanical systems based multirate modulator: Recent advances in (Microelectromechanical systems or MEMS technology may allow one to directly modulate each location on a 1D or a 2D image by employing an array of MEMS-based cantilevers, each vibrating at a different frequency determined by the underlying electronic driver. This opens up the possibility of varying the frequency map in order to suit the application. These MEMS-type of cantilevers may be used to modulate any electromagnetic radiation. By changing the frequency map, different functionality can be achieved. An example includes simultaneous acquisition of edges and the coarse image (see Section 18.g).

14 Transformation property of the multirate modulator: The comments in this section apply equally well to the case of 2D encoding by multirate modulators. Again the basic properties are made clear with the help of 1D example. The discrete cosine transform (DCT) of the 1D image I(x) sampled at discreet points $x_1$, $x_2$ etc. is defined as $$C_k = \sum_{j=0}^{N-1} I_j \cos\left(\pi j \frac{k}{N}\right), \quad (23)$$

The above equation may be directly compared to the Equation 4. Let us explicitly rewrite Equation 4 with the frequency map $$\omega_m = \omega_l + m\Delta\omega x_m \quad (24)$$

provided by the multirate modulator. The signal from the AC coupled detector is $$s(t) = \sum_{j=0}^{N-1} I_j \cos[(\omega_l + j\Delta\omega)t]. \quad (25)$$

s(t) represents the cosine transform of the image except for a shift in the frequency space by $\omega_l$. The signal received by the detector may be retranslated by $\omega_l$ by a mixer and a low-pass filter or may be shifted digitally by a digital signal processor. The ADC digitizes the signal at times $t=0$, $\Delta t, \ldots, k\Delta t$, with $\Delta t=1/f_s$, where $f_s$ is the sampling frequency. Putting it all together (including translation and filtering), Equation 25 becomes $$s_k = \sum_{j=0}^{N-1} I_j \cos\left[2\pi j \Delta f \frac{k}{f_s}\right] = \sum_{j=0}^{N-1} I_j \cos\left[\pi j \frac{k}{(f_s/(2\Delta f))}\right]. \quad (26)$$

From Equation 23 and 26 it follows that $C_k$ and $s_k$ are identical if one chooses $f_s/(2\Delta f)=N$. This shows that the multirate modulator may directly provide the DCT of the input image. Similarly, one may carry out the sine transform in which the digitizer and the encoder have a relative phase shift of $\pi/2$.

The usual Fourier transform of the image is made from the sine and the cosine transforms but needs to have an extra factor of 2 in the argument of the cosine shown in Equation 23. One may write the discrete Fourier transform (DFT) of image data I(x) as $$F_k = \sum_{j=0}^{N-1} I_j \exp\left(2\pi i j \frac{k}{N}\right) = \sum_{j=0}^{N-1} I_j \cos\left(2\pi j \frac{k}{N}\right) + i \sum_{j=0}^{N-1} I_j \sin\left(2\pi j \frac{k}{N}\right). \quad (27)$$

By repeating the steps shown above for the DCT, and choosing $f_s/(\Delta f)=N$, one may directly get the DFT of the image data. The above analysis illustrates a general property of dynamically encoded signals in that the received detector signal from a multirate modulator represents the transform of the basis functions used for encoding.

Figure 16A:
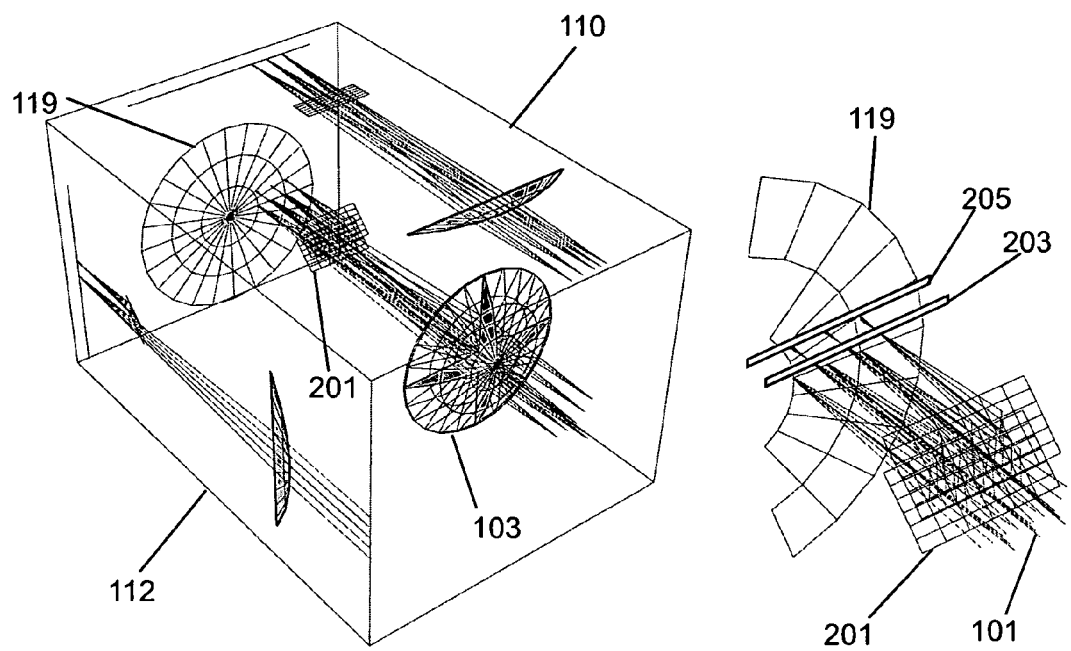
FIGS. 16a and 16b show two methods of acquiring the encoded signal with two channels in quadrature.
Figure 16B:
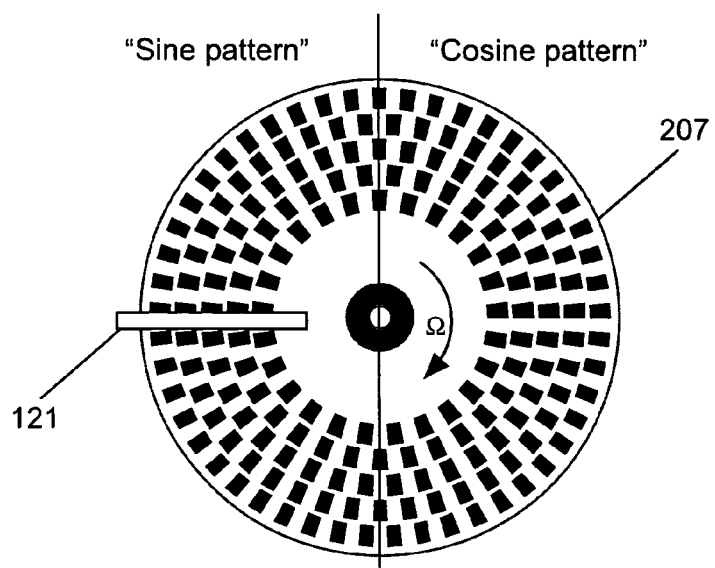

14.a Acquisition of the Real and Imaginary parts of DFT: FIGS. 16a and 16b give some of the possibilities for producing the DFT of the image described above using rotating disk 119, but the principle may be extended to any multirate modulator 105. In FIG. 16a, the image formed by the imaging system 103 is split by the beam splitter 201 to form two lines separated by a distance on the disk such that the phase of the encoding of the two images are separated by 90 degrees. Two independent detectors systems such as 111 are then used to collect signals from each quadrature channel. Another method shown in FIG. 16b may be to multiplex the same detector alternately by making the rotating disk pattern 207 such that the two halves form "sine" and cosine" patterns. This is accomplished by inserting a 90 degree phase slip between the two halves of the pattern. These two "sub-frames" individually represent the sine and the cosine transforms.

14.b Optical correlator: The same multirate modulator may be used to simultaneously carry out the DFT's of two objects and multiply the DFT's which results in the DFT of the convolution of the two objects. Clearly the time domain data received by each of the detector (or pair of detectors for complex data) may be multiplied in real time (which is equivalent to multiplying the DFT's) and the result Fourier transformed to yield the convolution operation. Furthermore, k-space translations may be carried out by the translation in the frequency space performed by the mixer by providing frequency offset from $\omega_l$.

14.c Ease of image compression: Many image compression algorithms such as JPEG use DFT or DCT. The image captured by the multirate modulator based camera is already in the transformed space and the extra step of computation of transforms can be avoided for compression of image. By choice of appropriate basis set for the encoding, much computation may be carried out directly by the multirate modulator.

15 Use of other transforms and patterns: There are many other special functions that may be used instead of cosines and sines as a basis of pattern map. These functions are now parametrized by time and the image data is now reduced to the basis set corresponding to these functions. I will list some examples and its usefulness for an imaging system based on multirate modulator.

15.a Hadamard and related functions: These are "square wave" like functions and its transforms are carried out similar to Fourier transforms but have the advantage of higher computational efficiency.

15.b Golay and other complementary sequences: Golay sequences $a_k$, $b_k$ are well-known examples of a complementary pair of sequences that have been used to recover the time-domain response of a system while increasing the signal-to-noise ratio in measurement. I provide a specific example using Golay sequences. Golay sequences have the property that the sum of the autocorrelation functions of the two sequences is proportional to the delta function. This property is used in recovering the response of the system by measuring the response of the system to the excitations by temporal sequences $a_k$ and $b_k$. There are two ways to use Golay sequences for 1D imaging.

Figure 17:
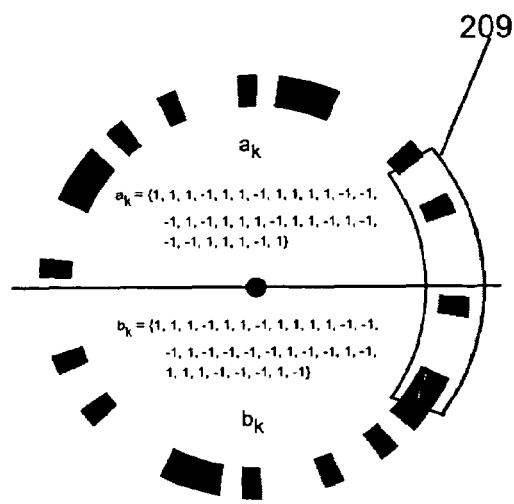
FIG. 17 is an example of one ring from a disk based multirate modulator based on Golay sequences.

In a simplest example, the pattern on the disk along the $\theta$-direction may be divided into two regions corresponding to the complementary pair of Golay sequences of length $2^n$. As the disk rotates, the image along the $\theta$-direction is convolved with the complementary patterns. From the measured time-domain signal, the 1-D image may be recovered using the property of the Golay sequence mentioned above. FIG. 17 shows an example of a rotating disk pattern 209 with Golay sequence along the $\theta$-direction. Only one ring is shown for clarity with the Golay sequence used for making the pattern. Note that there are many ways to arrange the sequence on a rotating disk as well there are many classes of complementary sequences that may be used.

Of course a similar kind of encoding may be performed in the r-direction. For example, each r-ring may contain the same complementary sequence but shifted by a single element in the sequence, which allows one to reconstruct may the 1-D image along the r-direction.

15.c Complementary sequence modulated carrier encoding for 2D imaging: The Golay sequences may also provide us with a convenient method to directly recover a 2D image. First, each ring corresponds to a different modulation frequency (perhaps created by phase encoding as suggested in Section 6) which will serve as a carrier frequency for Golay pattern. This by itself simply recovers a projection of the image along the radial direction. Now one further modulates the pattern along the $\theta$-direction on each of the rings with a complementary Golay sequence. A particularly efficient method is to simply provide $\pm\pi$ phase shifts in a phase-based encoding corresponding to $\pm 1$. Another may be to amplitude modulate the pattern shown in FIG. 17. By appropriate design of the Golay sequence (along $\theta$) and the carrier frequency (along r), both the dimensions of a 2D image may be uniquely labelled. A good 2D image may be recovered by using the property of the Golay sequence at each of the separate carrier frequencies assuming that the side-bands generated around each of the carriers by the Golay sequence based modulation did not overlap significantly with adjacent channels. Interleaved scanning scheme of Section 5 may be put to use here to avoid overlap with adjacent channels.

15.d Off-centered pattern: In this case, the pattern on the rotating disk is not centered on the point of rotation of the disk. This causes the pattern to wobble and during the course of rotation, the frequency of a particular point on the image changes sinusoidally. It can be shown that one may use this information to increase the apparent resolution. As the disk rotates the same image is sampled at different positions due to "wobble" from the off-centered rotation. The different positions are marked by slightly different modulation frequencies as the disk rotates. Multiple lower resolution reconstructed images are sliding samples of the original image from which a higher resolution image may be constructed.

16 Methods for the manufacture of patterns: There are many ways to imprint patterns on the disk as well as causing light modulation. The method of writing and making masks has to be chosen appropriate to the electromagnetic frequency of interest. For example, masks for the X-ray frequency may use alternating patterns of high-Z (Z corresponds to the atomic number) and low-Z materials to provide variability in transmission for the X-ray energy of interest. In another example for simultaneously imaging visible, near infrared, mid infrared and thermal bands, one may use metal on $CaF_2$ which is transparent throughout the entire region of electromagnetic spectrum mentioned. This may be accomplished using the means discussed below.

16.a Projection lithography, image setting, and contact printing: These are common techniques and are readily available. There are many commercial houses that print up to 4000 dots-per-inch patterns on large rigid or flexible substrates and this technology continues to improve. For very high resolution printing, one may use projection systems used in semiconductor industry that use either a stepper or a scanner to expose a mask pattern on a disk or other substrate of choice used for multirate modulation.

16.b Direct write by a laser or an electron beam: Direct write laser and electron beam machines are used in the industry today to write masks for printing using projection lithography. These machines are capable of writing on large substrates, with very high resolution. Of course, writing on a large substrate with a scanned laser or an electron beam is a slow process and is generally reserved for masters from which multiple copies are made using techniques such as projection lithography and contact printing.

Figure 18:
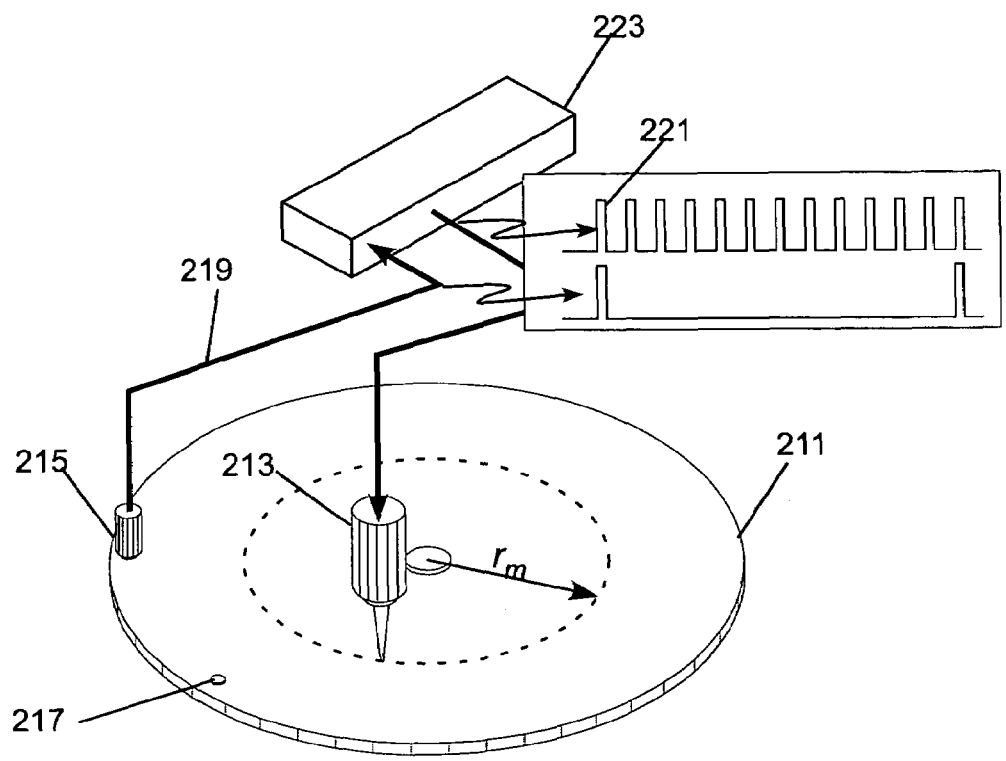
FIG. 18 illustrates a method for manufacturing circular patterns for disk based multirate modulator.

For writing complex pattern on a disk, one may use a simple mass manufacturable technique adapted for a circular pattern in which one uses an electron beam or a laser beam to directly write the patterns. The basic process of writing is illustrated in FIG. 18. This may be accomplished by directly modulating the laser (or an electron beam) 213 with an arbitrary pattern generator in conjunction with the computer system 223. Before writing, the disk 211 is prepared with an appropriate photoresist and a single notch (or any other mark) 217 to denote a reference point on a circle. The disk 211 mounted and rotated at a constant rate. The pulses are generated by a photodetector 215 from the reference mark so as to provide a time for a single rotation. The laser (or an electron beam) 213 is positioned at a point $r_m$ from the center. Now a pulse train of m pulses of of variable duty cycle contained within the time marked by the single revolution writes a pattern such that modulation frequency of $mf_{disk}$ is produced. At each radius r, the computer 223 may be programmed to generate the appropriate pulse sequence 221 to write the desired pattern. Writing of complex patterns may be accomplished by simply programing the appropriate pulse sequence. With this technique, one may write complex amplitude and phase masks for advanced processing of the images using the multirate image modulation technique.

Another advantage of this technique is ability to write on curved surfaces. Since the laser beam may be positioned and focused on the surface (using well-known auto focus methods), one may directly develop masks on lens and other specially curved surfaces as examples of multirate modulators. Laser interference patterns may be used for direct and chirped gratings. Flexible moulds may be used for writing patterns on non-planar substrates for application mentioned in Section 18.m 17 2D image encoding: There are many ways to extend the technique described above to the case of 2D imaging. There are two broad class of choices. The first class may include: (1a) scan in the other dimension to generate a 2D image, (1b) use a linear array of detectors, with each detector in an array capturing an entire row or column of the image, and (1c) use tomographic reconstruction technique by using multiple 1D reconstructed projections of the image. The other class may include: (2a) use two rotating disks or an equivalent multirate modulator, (2b) use a special chirped pattern on a single rotating disc or an equivalent multirate modulator, and (2c) Golay (or other complementary) sequence modulated carrier as discussed in Section 15.b.

The first class of techniques are extensions of the 1D to 2D by reconstructing a row/column in a group. In the second class of choices, the 1D technique is directly extended to produce 2D frequency maps such that 2D image may be directly reconstructed from a 2D dynamically encoded signal.

17.a Linear array gives a 2D image: The 1D system described in the previous section is extended by including a scanning mechanism that scans in a direction orthogonal to the 1D image capture. In this case, the entire 2D image is reconstructed line by line. This technique essentially uses the same system as 1D. For a simultaneous read-out of the image, one may use a 1D detector array shown in FIG. 11*b* where each detector in a detector array 179 is responsible for the entire line image as in the 1D case. This requires either a fast serial readout of the pixels or simultaneous readout of the detectors using parallel set of amplifiers and ADC's. This technique allows one to build a standard 2D focal plane camera by using only a 1D detector arrays. These 1D arrays often are easier to manufacture and may have higher signal to noise ratio. This technique may enable one to build a camera capable of imaging multiple spectral regions with excellent registration of pixels from one band to the other. The simplest example is that of a standard RGB camera. This is explained in Section 18.1.

Figure 19:
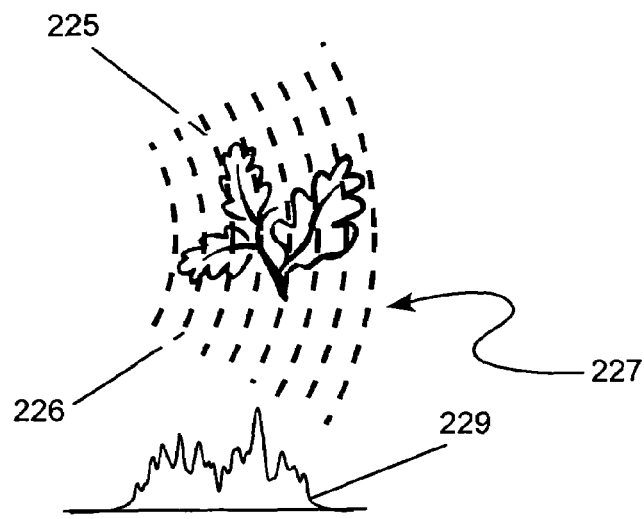
FIG. 19 shows some of the lines of constant modulation frequency on a 2D image due to a rotating disk multirate modulator. The projected reconstructed image is also shown.

17.b Tomographic reconstruction: Tomographic reconstruction allows one to recover a 2D (or a 3D) image from a set of projections of the object at various angles. This principle may be applied to recover a 2D image from a set of 1D projections of the image. Rotating disk multirate modulator allows one to acquire a set of 1D projections. The discussion below may be generalized to many other types of multirate modulators. FIG. 19 shows a 2D image 225 projected by an imaging system on the imaging region of the rotating disk such as 119. For clarity I have shown only a some of the arcs 227 from rings corresponding to to the modulation pattern on the rotating disk such as 119. For each arc such as 226, all the parts of the image that intersect that arc have the same modulation frequency. In this case, the FFT or the reconstruction of the dynamically encoded detector signal corresponds to the projection of the image along the arcs of constant radii. This reconstructed projection 229 is shown at the bottom. If the size of the image is small compared to the size of the disk, then the arcs (corresponding to the θ-direction) are almost tangential to the radial direction and may be considered to be lying along the y-direction if the radial direction is considered the x-direction of the image. The treatment of (r, θ)→(x, y) is carried out for the sake of simplicity but without the loss of generality. The frequency assignments on the image may be written as, $$s(t)=\int dy \Sigma I(x_m, y)\cos(2\pi f(x_m)-(2\pi/\Lambda)y), \quad (28)$$

where $\Lambda$ is the period on the rotating disk. The amplitude of the frequency component at $f_m$ corresponds to the projection $P_m(x_m)$ of the original image given by, $$P_m=\int I(x_m, y)\cos[(2\pi/\Lambda)y]dy \equiv \int I(x_m, y)\cos(Ky)dy. \quad (29)$$

$P_m$ is the cosine modulated projection of the image along the x-direction (or more accurately along the curves of constant frequency) as shown in FIG. 19. A complementary set of projections corresponding to $$P_m'=\int I(x_m, y)\sin(Ky)dy \quad (30)$$

may be extracted from the image by many well known methods of digital signal processing such as use of Hilbert transforms, quadrature lock-in etc. 2D image is reconstructed by using multiple projections of the image. These series of projections are acquired by many different methods. Some of them are described below.

The reconstructions from the pair of Equations 29 and 30 will allow us to recover two "images in quadrature"—$I_c=I(x, y)\cos Ky$ and $I_s=I(x, y)\sin Ky$. From these two images, the image may be computed by taking the square root of the sum of their squares. I disclose three methods to vary the angle of projection in a systematic fashion. Two of them are shown below and the other is disclosed in conjunction with frequency maps associated with the use of two disks.

Figure 20:
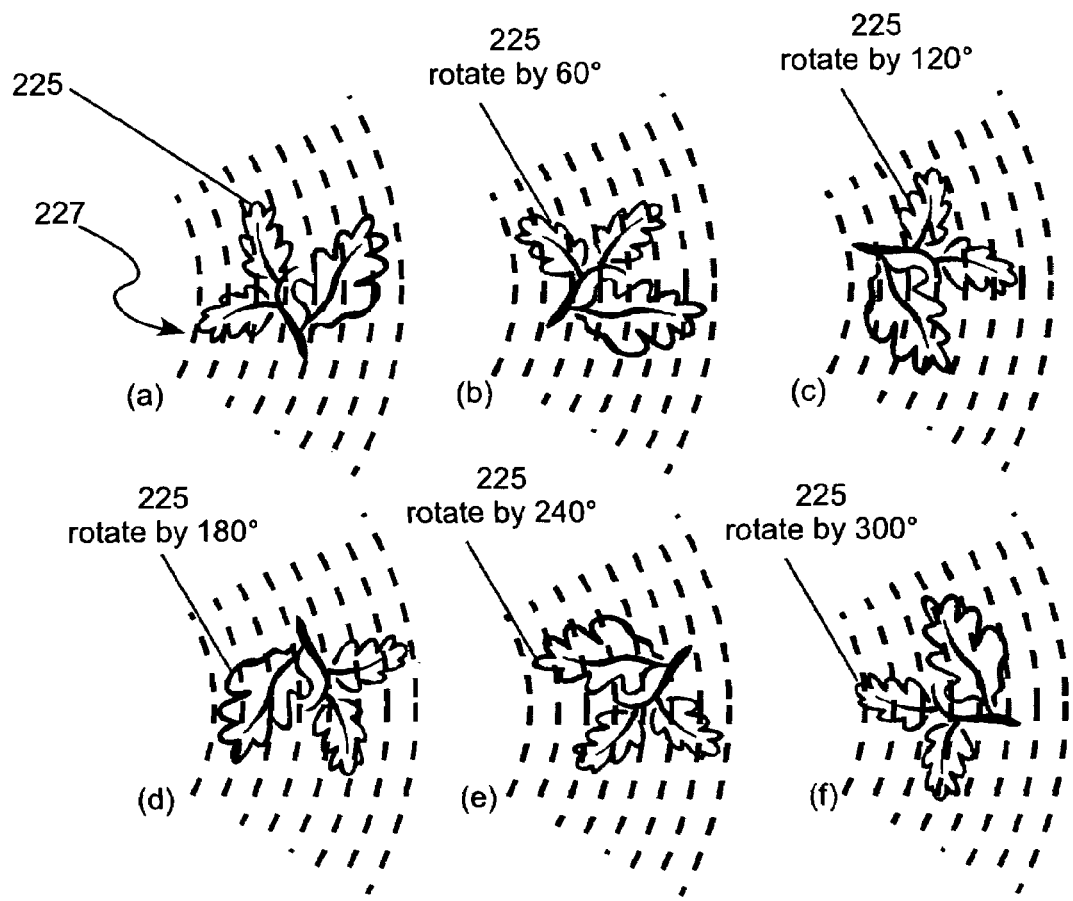
FIG. 20 shows sampling of six roations of a two dimensional image. These rotations allow projections of the image at various angles to be acquired.
Figure 21:
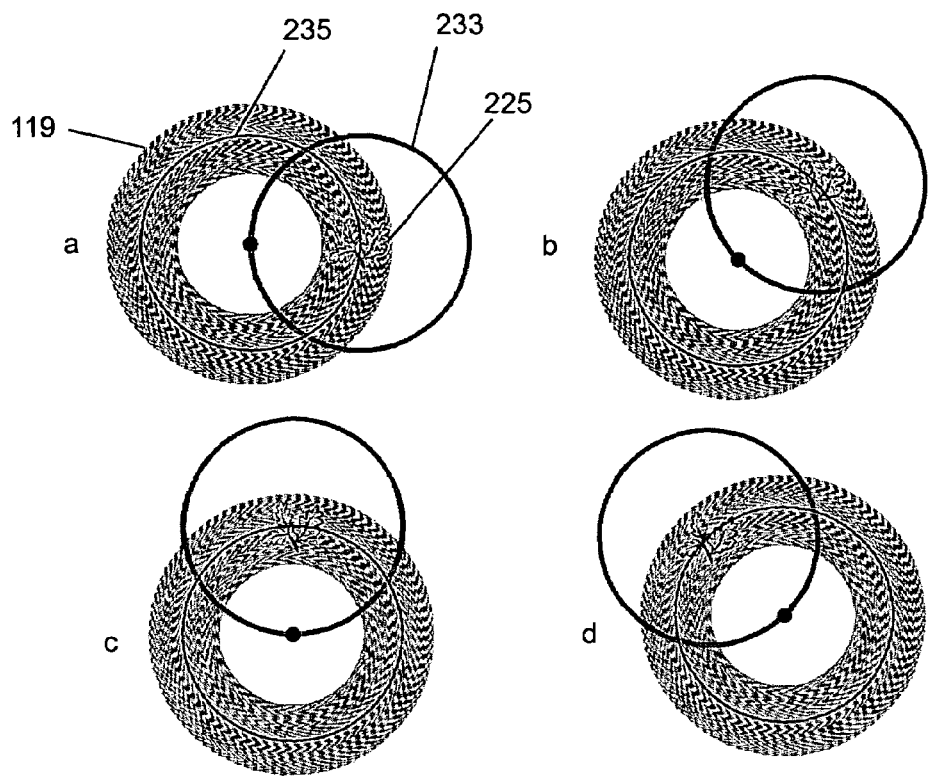
FIG. 21 is another method of measuring various projections of the image by rotating the center of the rotating disk on a circle.

Multiple projections for reconstructing a 2D image using tomographic techniques may be captured by rotating the image on the roatting disk. A sampling of number of rotated images are shown in the FIG. 20. For each position of the rotated image, projection of the image such as 229 is acquired. From this series of projections, one may reconstruct the 2D image using techniques of tomographic reconstruction. The rotation of the image may be carried out by many methods. One may be to rotate a Dove prism placed in the imaging system, which in turn would rotate the image. In FIG. 21, I show another method for capturing projections at different angles. This is accomplished by moving the center of the rotating disk 119 along the trajectory shown as 233. As the center of the disk moves along a circle, the curves of constant frequency such as 235 cross the image 225 at different angles. This projects the image at different angles. Tomographic techniques may be applied to the series reconstructed projections to recover the 2D image. In another method, one may use multiple imaging systems placed in a circular fashion with multiple images formed in a circular fashion around the disk. Each of this images form different projections. Projection of each of the images are collected by collector system and corresponding multiple detector systems 111. Essentially we have replaced rotations of the image or a circular motion of the disk with a finite number of projections collected simultaneously around the disk. In such a case we have also increased the total light collection efficiency. In the next section, I disclose yet another method for gathering various projections of the image. Many tomographic back-projection algorithms use Fourier transforms in their computation, and some of those computations may be eliminated since Fourier transform is built into the projected signals due to the properties of a multirate modulator discussed in Section 14.

17.c Direct 2D frequency maps: In this case a 2D image is directly encoded by assignment of unique frequencies to each pixel. These techniques fall into two categories: (a) Two disks or two cantilevers that together assign a unique modulation frequency to each "pixel" in an image plane and (b) a single disk with a more complex pattern and data reduction technique.

Figure 22:
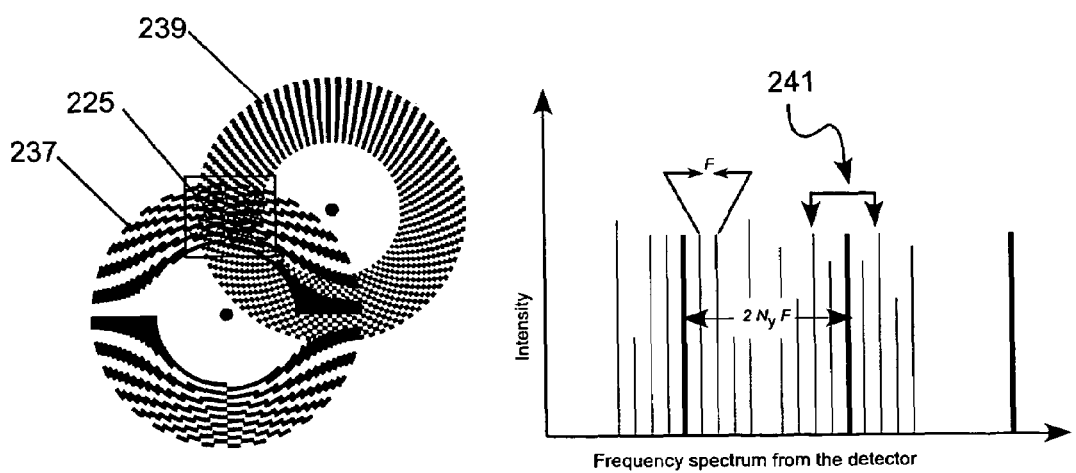
FIG. 22 illustrates two disks with mask patterns such that together they produce a unique map of frequency to location on a 2D image.

17.c.1 Two disks: The method for encoding with two disk is as follows. The two disks are placed as shown in FIG. 22. The first rotating disk 237—with disk frequency $f_{dx}$ and radial direction corresponding to the x-direction of the image 225—assigns frequencies along the x-axis of the image and the second disk 239—with disk frequency $f_{dy}$ and radial direction corresponding to the y-direction of the image 225—assigns unique frequencies along the y-axis of the image 225. The transmitted intensity at each location I(x, y) denoted by ring indices (m, n) corresponding to the modulation frequencies $(f_m, f_n)$ is $I(x_m, y_m)\cos(2\pi f_m t)\cos(2\pi f_n t)$.

Both $f_{mx}$ and $f_{ny}$ depend on the disk rotation frequencies and the patterns on the individual disks. This allows for lots of choice in the frequency map by choosing combination of disk rotation frequencies and patterns for modulation. One interesting case is to identify the frequency map such that each pixel (or location on the image) corresponds to a unique frequency. Using the trigonometric identity, one sees that each location corresponds to two frequencies—$f_m+f_n$ and $f_m-f_n$. If the x- and the y-disk map of frequencies are given by $$f_m=f_{0x}+m\delta f_x, \text{ where } m=1, 2, \ldots, N_x, f_n=f_{0y}+n\delta f_y,$$
$$\text{where } n=1, 2, \ldots, N_y, \quad (31)$$

then assignment of frequencies may be made as shown in the table below. Furthermore, the table assumes an imaging system operating with frame rate of F Hz. This table illustrates two important cases.

|  | Case 1 | Case 2 |
|---|---|---|
| $\delta f_{0y}$ | 0 |  |
| $\delta f_y$ | F | $\alpha F$, $\alpha$ varies from 0 to 1 |
| $\delta f_x$ | $2N_y F$ | $\beta F$, $\beta$ varies from 0 to 1 |
| Sum frequency | $f_{0x} + F(m(2N_y) + n)$ | $f_{0x} + F(\alpha m + \beta n)$ |
| Difference frequency | $f_{0x} + F(m(2N_y) - n)$ | $f_{0x} + F(\alpha m - \beta n)$ |
| Unique? | Yes. See FIG. 22 | No. Intensities of pixels along the lines of constant slope given by $\pm \text{atan}(\beta/\alpha)$ are projected. |

In case 1, unique frequencies are assigned to individual pixels with the frequency map shown in FIG. 22. Note that I have used two disks 237 and 239 with very different patterns (as shown in FIG. 22) with the disks positioned to modulate the picture at varying rate along both the axes of the 2D picture. Each pixel corresponds to two frequency components shown as a pair 241 in the FFT of the signal. The image may now be reconstructed.

For Case 2 in the table, one obtains projections 245 of the image 225 along lines 243 as shown in FIG. 23. The projection angle of a line 244 (as part of a group 243) depends on the ratio of rates of rotaion of the two rotating disks. This is because the lines of constant frequency modulation 243 depend on the ratio of the disk rotation rates. As the frequency ratio is swept, all possible projections may be measured and the image computed. This is now similar to the case discussed in Section 17.b with the added advantage one does not have to physically rotate the image or move the center of the disk.

17.d Chirped patterns: This is a more complex case of encoding the 2D image with a multirate modulator 105 in which frequencies are chirped along one of the direction (say along columns or in the θ-direction). This frequency chirp leads to the support of width Δf around the center frequency $f_m$. By separating the center frequencies along the orthogonal directions (say along rows or in the r-direction) by amount greater than Δf, one may assign modulation frequency to each location on the image such that the entire image may be recovered. The pattern requirement and algorithm for one simple case is presented first and then its generalizations are considered.

For the sake of simplicity (but without losing any generality) let us again consider the two orthogonal directions to be along x- and y-axis. In the previous section I used two disks to uniquely assign frequencies to each location (x, y) which also correspond to the pair of integers (m, n). The trigonometric algebra produced both the sum and difference components which in effect "wasted" half the available bandwidth by redundantly encoding the same pixel information at frequency locations $f_m \pm f_n$. By using a chirped frequency pattern along the y-direction, one avoids the bandwidth waste and use only one disk.

Consider a 2D image 225 shown in FIG. 24a with a mask pattern 247 such that the spatial frequency of the pattern is changed in y-direction 251. First let us focus on a particular column (or a particular radius) denoted by its center frequency $f_m$. At any given point in time, the motion of the mask along the y-direction 251 gives a local modulation frequency $$f_m(y) = f_m + \alpha(y) \quad (32)$$

where α is the chirp parameter. If the total frequency spread is Δf and occurs by translating the mask distance $A_y$, then it follows that $\alpha = (\Delta f)/A_y$. One may pick $A_y$ such that more than one repetitions of the frequency sweep occur for one rotation (or oscillation) of this specific mask pattern 247.

Since the image 225 is fixed and the mask is translated at a uniform velocity v, it is easy to see that the light from a particular location y on the image is modulated such that there is a linear frequency sweep. For clarity, a section 252 of the image 225 and a section 249 of mask pattern 247 are shown adjacent to illustrate the effect of motion along y-direction 251. This sweep is given by $$f_m(y, t) = f_m + \alpha(y - vt) \text{ where } 0 < t < T_y. \quad (33)$$

Modulation frequencies (or in general encoding functions) repeat periodically and will change in a saw-tooth like fashion. If $A_y$ is the spatial extent over which the chirped pattern repeats, then the frequency sweep repeats with a period $T_y = A_y/v$. Note that the above equation immediately gives us the requirement on the on the spatial period P=P(y) of the pattern since it is the motion of the pattern that causes modulation. This is simply $f_m(y) = v/P(y) \Rightarrow (2\pi)/P(y) = k(y) = \omega_m(y)/v$. An example of chirped pattern with only 4 periods along a circle is shown in FIG. 24b on rotating disk 255. Compare that to a simple pattern on a rotating disk 119. For discussion below, I have ignored the DC term and the higher harmonics generated by the pattern (see Equation 4 and its discussion) and write the received signal intensity as $$s(t) = \int I(y) \cos[f_m(y, t)t] dy. \quad (34)$$

Since one knows the periodic function $f_m(y, t)$ over the interval $T_y$, original data I(y) from the received signal s(t) may be reconstructed by using $$I(y') = \int s(t) \cos[f_m(y', t)t] dt = \int dy I(y) [\int dt \cos[f_m(y, t)t] \cos[f_m(y', t)t]]. \quad (35)$$

The dt integral in the parenthesis is a Sinc function which allows one to increase frequency resolution and corresponding spatial resolution with increasing integration time T. The spatial resolution is $\delta y = (\delta f)/\alpha \sim 1/(\alpha T)$. The simulation of the above formulation was performed in LabView and Mathematica. In general for a well designed pattern, the product $N_x N_y F \sim f_0$, where the modulation frequencies are in the range from $f_0$ to $2f_0$ as discussed earlier.

Some advantages of the preferred embodiments of the multirate modulator are summarized below.

(a) Detector system 111 may be a single detector that collects signal from all the "pixels". There is no need to calibrate individual pixels. Rotating disk made from a high quality substrate can ensure uniform transmission quality across the entire 1D image.

(b) One rotating disk simultaneously generates dynamic coding for all the pixels. All the frequencies are locked to $f_{disk}$. Any variation in the rotation frequency of the disk will equally affect the modulation frequency of all the pixels. This may be eliminated by deriving the "sampling clock" for the ADC from the rotating disk itself. As shown in FIG. 7, a separate light source such as LED and detector may be used to generate the clock from the pattern on the disk. A separate ring may be provided that generates a clock as the disk rotates. The period P for the "clock-ring" need not be same as the period elsewhere. Now either the fundamental or the harmonic of this clock may be used as a sample clock $f_s$ for ADC. Note that from the sampling theorem one needs, $f_s > 2f_2$ where $f_2$ is the highest encoded frequency in Equation 4. The clock may also be directly recovered from the signal itself.

(c) Light from each pixel is "integrated" for the entire frame time T. This allows the multirate modulator to approach the S/N ratio of a physical N-pixel array integrating for the same frame time T. In case of interleaved scanning, the S/N ratio is degraded by $\sqrt{s}$, where s is the number of sub-arrays scanned in a single rotation of the disk due to reduction in integration time by $s^{-1}$.

(d) Detector system may be AC coupled to eliminate or reduce low-frequency noise sources such as 1/f noise.

(e) One may simultaneously use both the reflected light (say from a disk patterned by metallization) and transmitted light and two detector systems such as 111 to improve the overall light collection efficiency of the system. Note that multirate modulators may be patterned with no gaps between the "pixels" which is difficult to achieve for physical detector arrays. This "fill factor" is responsible for reduction in the collection efficiency for the physical detector arrays.

(f) Reconstruction of the dynamically encoded image may either eliminate or greatly reduce the pixel-to-pixel crosstalk that happens in conventional detector arrays.

The crosstalk now originates when one takes the Fourier transform (or other appropriate transform) since the tails from the peaks (in the FFT) at each pixels "leak" into adjacent pixels. This may be mitigated by choice of windowing function and by increasing the frame time to increase the resolution in the frequency space.

18 Some specific application examples: In this section, I disclose various embodiments that use the principle of dynamically encoded light for specific uses. I illustrate these examples with a generic multirate modulator. In each case one may use some of the methods for implementing disclosed multirate modulator techniques.

Figure 25A:
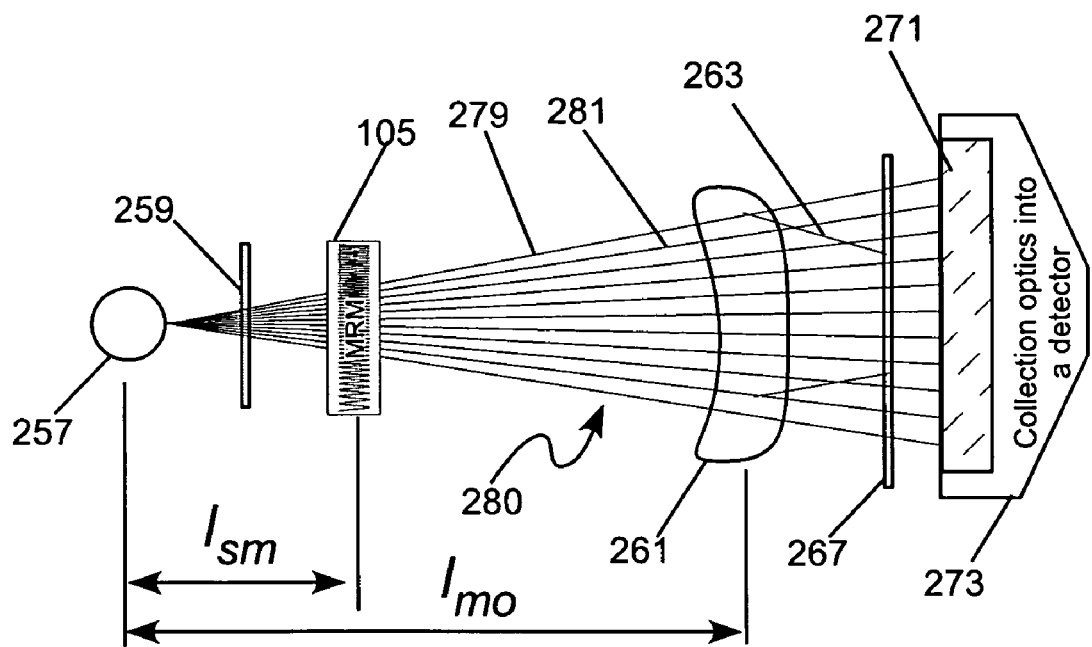

18.a X-rays and other ionizing radiation: For X-ray imaging, the method disclosed here may allow significant improvement in resolution. It may have the potential to lower dose and/or provide high resolution even with higher energy X-ray radiation. The idea described here for X-rays may be extended to many other spectral regins of EM radiation such as γ-rays, EUV, etc. The basic principle is illustrated in FIG. 25a. A rotating disk or an equivalent multirate modulator 105 is placed in the path of X-rays produced from source 257. The radiation from the source may be filtered by an spectral filter 259, dynamically encoded by the multirate modulator 105, transmitted through the object 261, and finally received on a detector 271. The scattered X-rays 263 from the object are optionally filtered by scatter prvention screen 267 to prevent signal generation from scattered X-rays. The multirate modulator 105 modulates the X-ray source 257 according to the principles described in the previous sections. All of the transmitted X-rays may be collected on a single detector 271 after passing through the object 261. In case of X-rays, one may use a sheet of scintillator as a large area detector 271 that efficiently converts X-rays into a number of visible photons via a process commonly called scintillation. The scintillator material may be made thick enough to absorb all the X-rays and with appropriate time constant. The light output from the scintillator is collected without regard to the location where the X-rays were absorbed in the scintillator since that information is already coded by the modulation function. The modulation of the X-ray generated light in the scintillator material follows the X-ray modulation if the time constant of the scintillator is fast enough compared to the modulation frequency. The resolution of the image depends on the multirate modulator and not on either the thickness or the pixellation of the scintillator unlike traditional X-ray digital imaging. Using techniques described in the previous sections, one can recover the X-ray transmission image.

Figure 25B:
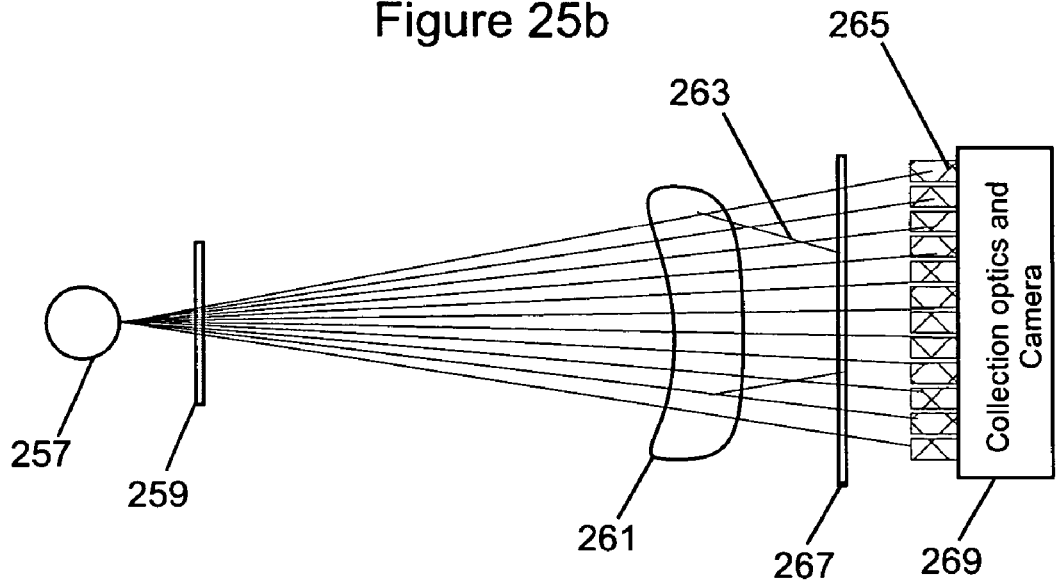
FIG. 25b is a schematic of an X-ray imager based on prior art for comparison.

The modulation of the X-ray source may be performed using any of the techniques described in the previous discussion. For example high Z materials have a higher stopping power than the low Z materials. A rotating disk with patterns of high Z materials may act as a rotating disk multirate modulator 105 for X-rays or other ionizing radiation. Some of the unique features and advantages of the imaging by optical encoding and reconstruction for "ionizing" region of electromagnetic radiation are described below. Resolution is independent of the detector pixelation. High quality, very uniform scintillators may be used to generate optical photons from the absorbed X-rays. FIG. 25b is a schematic of a typical Prior Art for digital X-ray imaging system. High sensitivity requires tall, optically isolated columns 265 of scintillator material registered to the pixel spacing of the underlying optical detector to increase luminescent yield. At the same time, each pixel needs to be isolated to reduce the cross-talk. Taller the pixel column, lower the resolution for a given acceptance angle for X-rays and harder it is to isolated one column from the other. For example, metal coated or air isolated scintillator columns have been used to reduce X-ray and optical crosstalk but are difficult to manufacture. But taller columns have higher stopping power and improves photon yield which in turn lowers the dose requirements. In order to satisfy the need for high-resolution, high-efficiency imaging, thinner scintillator materials with high stopping power such as CsI are used which are often expensive compared to NaI or many organic scintillators. With the disclosed technique one may use a thick, uniform, inexpensive scintillator capable of providing adequate stopping power. Since the pixel information is encoded in the modulation frequency by the multirate modulator, location of the absorbed X-ray on the scintillation screen is unimportant. This feature may allow one to avoid high-cost, high Z scintillators with difficult to manufacture isolation columns for pixels. High resolution and high stopping power are both possible with the disclosed technique. This may allow one to lower the dose for biological imaging while providing high resolution.

Majority of X-rays used in diagnostic imaging of biological tissue are absorbed due to photoelectric effect which is the dominant absorption mechanism at low X-ray energies. Use of higher energy, monochromatic X-rays have a potential to lower the patient dose. Traditional imaging detectors have difficulty maintaining the trade-offs mentioned above as higher energy X-rays need thicker scintillators. Again, the disclosed X-ray imager may use thick scintillators without suffering a loss of resolution. Many medical X-ray techniques such as fluoroscopy may benefit from the advantage of lowering the total X-ray dose to both the doctor and the patient and yet providing adequate resolution.

Layers of multiple scintillation materials (or more complex scintillation materials with different luminescence wavelengths) may be used so as to improve sensitivity to different X-ray energies and/or to provide efficient conversion of most of the X-ray photons. This may allow simultaneous measurement of stopping power or transmittance of various X-ray energies through the object. Such a technique may enhance determination of material composition since different materials have different functional dependence of stopping power vs. X-ray energy.

Very high resolution X-ray imaging is possible. Consider geometry in FIG. 25a. The two adjacent rays 279 and 281 from a set of rays 280 are encoded by two adjecent regions on the rotating disk or a multirate modulator separated by Δr. This is projected on to the object 261 with the resulting resolution Δx.

$$\Delta x = \Delta r (l_{source-mod}/l_{source-obj}) = \Delta r (l_{sm}/l_{so}) \quad (36)$$

The above equation is valid for a point X-ray source. For a finite sized source, a convolution with respect to the source size will have to be carried out to determine the effective resolution.

There may be other benefits to lowered dose requirements. Reduction of the required dose may enable reduction in the spot size of the electron beam used in generation of X-rays (due to reduction in the space-charge effects and reduction in thermal load on anode due to smaller beam current), which may increase available X-ray imaging resolution. Performance of X-ray based Computer Aided Tomography (CAT) scanners may be improved. In some cases, helical scan may be replaced by direct imaging by the multirate modulator. In some other cases, multiple 2D images may be acquired for simple stereoscopic reconstruction.

For a rotating anode X-ray sources, the anode itself may be patterned (to produce both intensity as well as energy-spectrum modulation) or the e-beam scanned. High speed e-beam scan and modulation may further enhance the performance of the imager. E-beam scan on the anode may be used to generate a scanned image while the temporal modulation at high-speed may be used to determine the range of the scattered X-rays (and hence the position of the scatterer inside the object) using the technique discussed in Sections 11 and 18.i.

So far in this section, I have discussed how a scintillator may be used with the multirate modulator for X-rays. Fluorescence, phosphorescence, etc. are phenomena very similar to scintillation, in that, the incident electromagnetic radiation interacts with the material to cause internal excitations, which in turn results in emission of photons of (generally) lower frequency. The flux of emitted photons in this (generally lower) different electromagnetic frequency regime is proportional to the incident excitation radiation and often serves as a proxy measure of the power of the higher energy excitation. The scintillation in the discussion above may be replaced with fluorescence etc. with appropriate change of materials and collection optics. One of the fluorescence application popularly used in biology is described in Section 18.f Also, the principle described for X-ray imaging, may be generalized to any short wavelength radiation where one often uses scintillation (or fluorescence etc.) to produce the image. In many cases, electron-pumping is used to produce source light. In such a case, direct source modulation may provide some of the functionality of the multirate modulator. From the above discussion, the disclosed technique may be extended to all ionizing radiation—from UV to gamma rays as well as high energy particle detection.

18.b Far infrared, mm waves and other waves with long wavelengths: In the sections to follow, I will describe specific applications in commercially important regions of visible, near-infrared (0.8-2 microns), mid-infrared (2.0-7 microns), thermal infrared (7-14 microns). Near infrared is used in the telecommunication industry and some parts of it are eye-safe and used in medical applications. Mid-infrared as well as thermal infrared may be used in night-vision systems or for spectroscopic imaging because of large number of vibrational transitions in organic molecules in this region. Far infrared and mm-wave regions are just being commercially exploited because of their unique properties. For example, around 70-90 GHz region (approx. 3 mm), most materials such as water, dust, and ice have very similar refractive indices. These and other properties make the mm-wave region useful for detecting camouflaged vehicles/weapons or for collision avoiding radar. Most of the above regions of electromagnetic spectrum use expensive detector technologies and the imaging arrays may be particularly expensive. It is quite common to find prices in the $20,000-$100,000 range for video-resolution cameras for these wavelength regions.

The multirate modulator based camera in these regions may directly be able to reduce the cost of the imaging system. By utilizing a single, high-quality detector for reconstructing the encoded image, the cost of the electronics, focal-plane array and cooling may be significantly reduced. In the mm-wave region, the multirate modulator may be made by making slots in the metallic disk to let the radiation through (these holes may be made resonant by making the size of the slot equal to the quarter of the wavelength thus acting as an antenna). Now a single mm-wave detector may be used to reconstruct the image. Imaging longer wavelength EM radiation requires one to take into account wave-like nature and diffraction in the design of the apparatus (including multirate modulator).

I have also described an extension of the disclosed technique in Section 19 in which a pair multirate modulators are used to directly form the image without the need for lenses and mirrors. This may further reduce the cost of the imaging systems where lens materials are expensive and/or difficult to fabricate.

18.c Spectroscopy: This is an extension of the multirate modulator technique to spectroscopy. In this case, a spectrum of the incident electromagnetic radiation is encoded using any of the multirate modulators described in this disclosure. This is illustrated in FIG. 26. The input light beam 101 containing many wavelengths is dispersed by a spectrometer or a dispersing system 283. The dispersed beam 285 may now be modulated using any of the multirate modulator concepts discussed previously using multirate modulator 105. This modulated spectrum may be collected for analysis and reconstruction by one of these methods among others: a collection system 107 based on lenses and mirrors as shown in FIG. 26a or another based on dispersing system 283 with the role of input and output switched as shown in FIG. 26b. In the latter case, the spectrally encoded light beam 285 is produced. The spectrum of the input electromagnetic radiation 101 from a source may be reconstructed in a manner similar to 1D image reconstruction. This is because multirate modulator provides a one-to-one map of modulation frequency $f_m$ to optical wavelength $\lambda_m$. After modulation, the modulated spectrum may be collected on a single detector. Some of the other embodiments of the spectroscopy system that produce spectrally encoded light beam 285 are shown in FIG. 27c. Three options are shown in which the same dispersive system is used in a "double pass" arrangement to produce spectrally encoded beam. The spectrally encoded light 285 propagating backwards may be separated from the incoming light by (1) using a beam splitter 287 as shown FIG. 26c, or (2) tilting the back-reflected rays to slightly separate the outgoing light from the incoming beam as shown in FIG. 26d, or (3) by using a polarizing beam-splitter 289 and a quarter wave plate 291 as shown FIG. 26(e).

Some of the features of this encoded spectrum spectroscope or the spectrally encoded light 285 are discussed below. The entire spectrum may be read by a single detector without scanning slits or scanning dispersive elements such as grating. One need only calibrate spectral response of only a single detector. Resolution is limited only by the pattern on the disk (or some other multirate modulator) and the properties of the dispersive system. The multirate modulator may be optimized to provide slightly different pattern along the radius of the disk to match the spatial dispersion characteristics of the dispersive element such as prisms, gratings, Echelles, etc. A rotating disk multirate modulator with $r_1=1$ cm and P=1 micron gives us spectrogram with 10,000 wavelengths. This corresponds to average frequency resolution of 40 GHz in the region from 400-800 nm.

Spectroscopy of the sample may be performed with the spectrally encoded light 285. The spectral reflectivity of the sample is measured by inserting a sample in the path of the spectrally encoded light 285. First a broadband source is encoded to produce the spectrally encoded light 285 using one of the embodiments mentioned above. This beam is reflected off (transmitted through) the sample and collected by the detector to measure the sample's spectrum. The change in the spectrum may be measured by comparing the spectrum of the spectrally encoded light 285 before the object (from a reference channel) to the spectrum after the object. The spectrally encoded light 285 before and after reflection from the sample may be carried on a fiber since the reflectivity data is encoded in the modulation spectrum. Optional reference spectrum detector may be used to directly subtract the incident spectrum of the encoded light for computing the spectrum of the sample's transmission or reflection.

An extremely broadband imaging spectrometer may be built using the disclosed technique. For example, a single pyroelectric detector may be used to determine the spectra from 0.2-20 microns. In another method, one may efficiently utilize multiple detectors optimized for different wavelength regions. This may be accomplished by placing a coarse dispersive element to detect radiation in each of the wavelength bands with the corresponding detectors after multirate modulator. Overlapping spectral regions on adjacent detectors may be used to cross-calibrate the spectral responsivity among different detector systems.

18.d Ellipsometry—single color as well as spectroscopic: This is based on combining the embodiments discussed for constructing a spectrometer (Section 18.c) and the embodiments for constructing a range measuring imager (Section 11). As discussed in the section on range detection, by using a reference detector, phase shift induced by the object (or by propagating to the object) at each of the modulated frequencies can be detected by a phase sensitive detection system. For the general spectroscopic ellipsometry application, one first modulates the incident spectrum of a suitably chosen polarized light as in the spectroscope application noted in the previous section. Now each of the wavelengths are modulated at a unique frequency. For simplicity and as a typical example, imagine that the incident light is linearly polarized at 45 degrees. After reflecting from the sample at a particular incidence angle, it is split into the two orthogonal polarization components and collected on two detectors. One may now measure both the absolute as well as relative amplitude and phase change introduced by the sample at the two polarizations. The effect of the sample alone may be isolated by subtracting the measurement of the amplitude and phase of the polarizations at the reference detector. From these measurements, the standard ellipsometric information from the sample at a given angle of incidence may be extracted.

Other modes of ellipsometry may also be used in conjunction with multirate modulator. For example, rotating waveplate technique may be used. The rotation of the waveplate gives rise to sidebands around each of the frequencies in the spectroscopically encoded modulation spectrum. The information carried by these sidebands can be decoded and the ellipsometric information reconstructed. Some of the advantages of this method are:

(a) Simple set-up and high sensitivity. The modulated light may be carried on an optical fiber to the sample. Using modulated light allows the measurement of the signal with very high sensitivity and avoids low frequency noise from the lasers and lamp-based sources.
(b) The technique may be configured for multiple incident angles and multiple wavelengths simultaneously. Alternatively, a light-weight optical head near the sample may be precisely positioned quickly at any angle, with ellipsometry performed across the entire spectra.
(c) The incident light beam may be split and reflected from a "reference sample" as well as sample under test. By using the light reflected from the reference sample as a "reference channel" for ellipsometric measurements, calibration errors due to absolute angle measurements may be reduced. The spectroscopic ellipsometry of a reference sample may be used to determine the angle of incidence.
(d) Enhanced UV operation. Ellipsometry in the UV region may become difficult due to the poor responsivity of Silicon detectors in the UV and higher transmission losses of UV light resulting in small signals. Use of modulated light and phase-sensitive detection may allow one to extend the measurements more easily into the UV region. This is particularly important due to advances in the lithography to sub-100 nm dimensions. These nm-scale line features and critical dimensions (CD's) may be determined more accurately by performing ellipsometry at short optical wavelengths.
(e) This technique may be readily extended to the EUV region for characterization of materials and optical components used for next-generation lithography.

Figure 28:
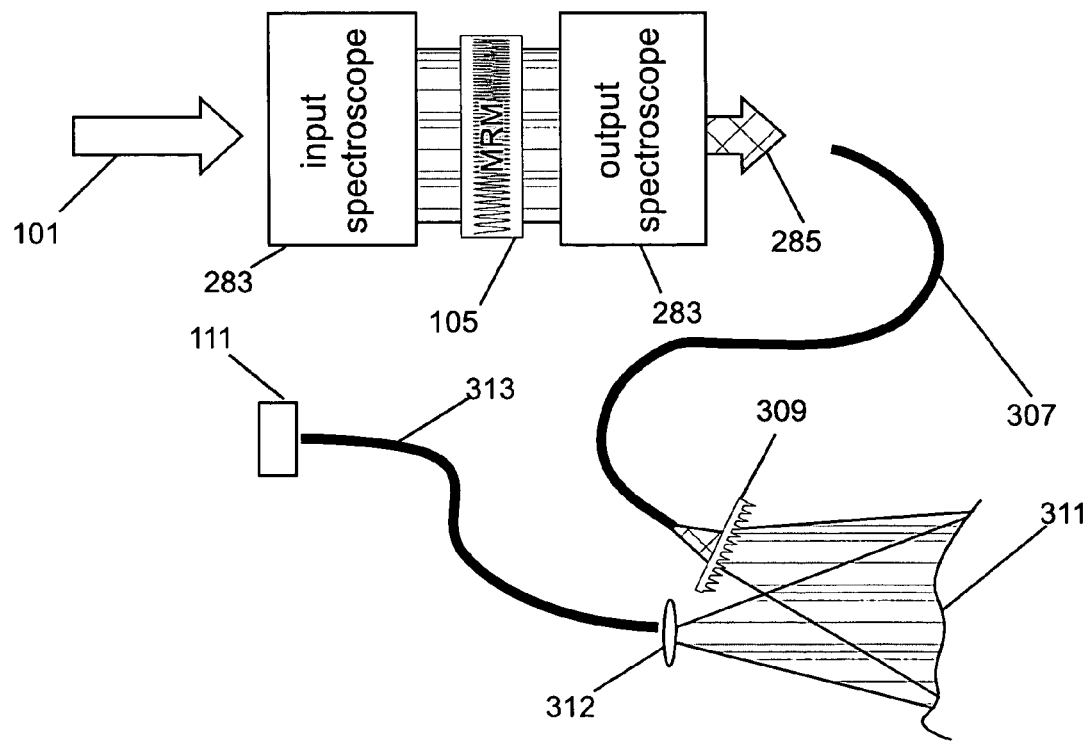
FIG. 28 is a fiber-optic based imager based on encoded spectrum.

18.e Fiber optic camera, endoscopy, and imaging with wavelength maps: In this case, one uses the encoded spectrum to make a high resolution fiber optic camera. The idea is outlined in FIG. 28. Various wavelengths of light are encoded as a spectrally encoded light beam 285 (see Section 18.c) and sent down a fiber 307. At the other end of the fiber, a grating or a spatially dispersive element 309 separates the light beam containing different colors and illuminates the object with different colors travelling in different directions falling on the object at different locations. In this way, there is a mapping between the modulated frequency (or encoding functions), wavelength, direction of spectral component, and location on the object. The scattered light from the object 311 is collected by a lens 312 at the end of the fiber 313 (could be the same as input fiber). The collected light is detected by a detector system 111. The reconstruction of the received signal is directly proportional to (or more precisely when divided by the input reconstructed from the reference detector) the scattered light intensity, which in turn corresponds to different locations on the object 311. A 1D image of the surrounding (albeit with wavelength dependent scattering) medium may be acquired with a single strand of fiber. In principle, this fiber may be a single mode fiber. Some of the features of the fiber optic imager based on this disclosed technique are described below.

The resolution of the image may depend only on the resolution of the spectroscope and the spatially dispersive element at the end of the fiber. The end of the fiber does not need an active electronic instrument such as a camera. This may allow use of fiber guides with very small in diameter. This is particularly important for endoscopes used in medicine where small diameter endoscope may significantly reduce or eliminate patient discomfort.

Figure 29:
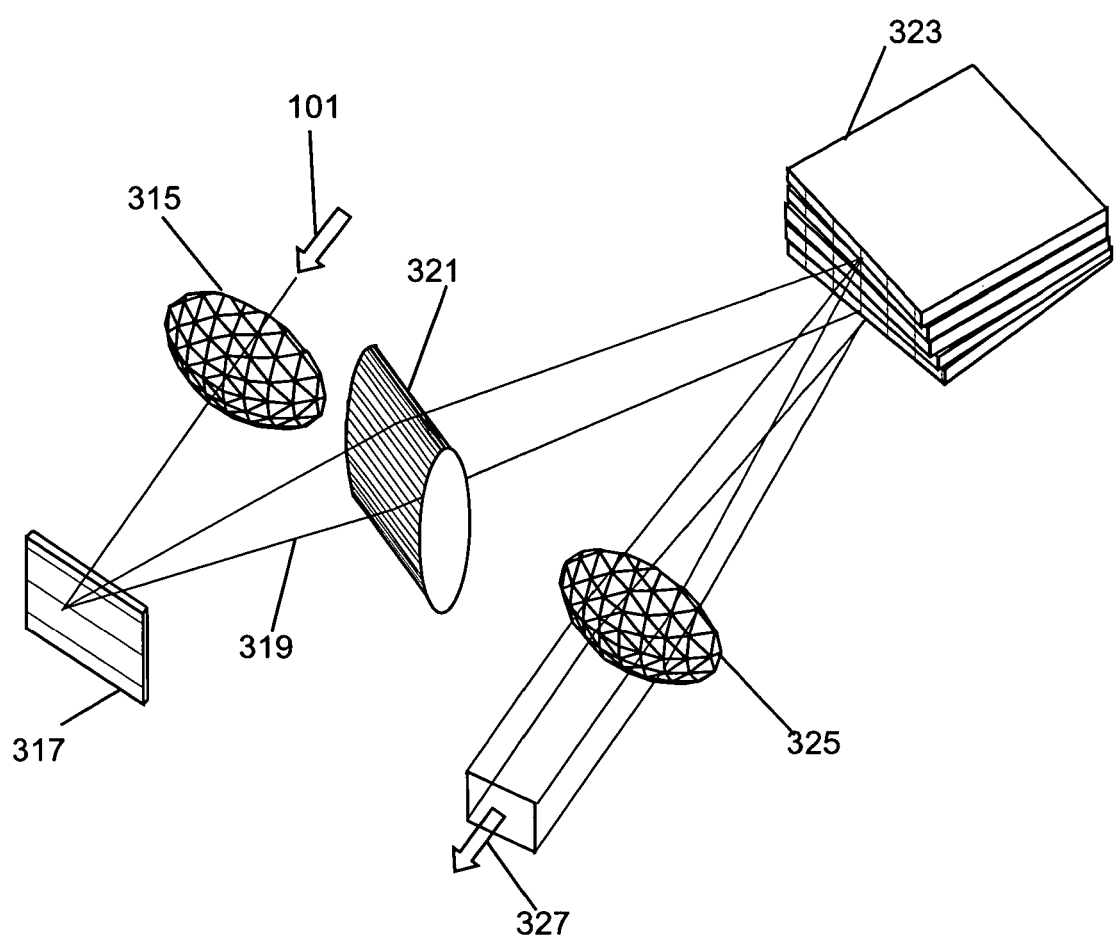
FIG. 29 illustrates a method for producing two dimensional map of spectrum so that 2D imaging maybe performed using fiber-optics.

An optical scanner attached to the inside end of the fiber may be used to scan the other dimension in order to create a 2D image. Other possibilities include a dispersive element that disperses the spectrum on a 2D space as opposed to a dispersion along a line generated by the usual dispersive elements such as grating, prisms, etc. In such a case, encoded 2D map is created to directly read a 2D image from the scattered light. An optical instrument that maps spectrum of incoming broadband electromagnetic radiation 101 to a 2D spectral map is shown in FIG. 29. The lens 315 collimates rays dispersed by grating 317. The first grating 317 separates colors along the vertical direction at a low resolution shown by rays 319. A cylindrical or astigmatic imaging system 321 is then used to disperse further in the horizontal (or orthogonal to the first) direction by a set of gratings 323. In this case, the set of gratings 323 is shown as a series of vertically stacked gratings such that the final map forms a continuous raster scan of wavelengths in 2D space as shown by a box 327. This may now be encoded by a 2D multirate modulator 105. The principle of imaging outlined in embodiment of FIG. 28 in 1D may now be extended to 2D.

Changing the group of wavelengths that are sent on the fiber will change the direction of the beam coming out of the fiber because of the spatially dispersive element such as 309 at the end of the fiber. In this instrument, wavelength scan is made equivalent to the spatial scan and wavelength resolution gives corresponding spatial resolution. This technique may provide both spatial scanning and zoom functions by manipulating the modulation of the spectrum. These properties of the embodiment enables remote scan and zoom functions. One may combine spectral imaging with range finding to create a full 3D image.

As another example, one may use this technique in combination with FLIM (as discussed in next Section) to perform complex fluorescence analysis for diagnostic purposes in medicine and nondestructive testing. This technique may be adapted for spying by passing the fiber bundle carrying fibers such as 307 and 309 through narrow spaces.

18.f Frequency domain Lifetime Imaging and Microscopy: This is another application of the basic principles described in the section on Spectroscopic Ellipsometry. Here one uses well-known principles of frequency domain fluorescence lifetime measurements and adapts them for use with the disclosed imaging system to provide enhanced capability. In general, one modulates the excitation source or the optical pump (typically towards the blue-end of the spectrum) using the multirate modulator. The fluorescence signal will follow the amplitude modulation of the pump and allows the reconstruction of the fluorescent image. The phase delay in the received fluorescence signal is related to the decay time by, $\phi=\omega\tau$, where $\omega$ is the local modulation frequency and $\tau$ is the local fluorescence decay time. Note that various techniques mentioned in Section 18.i may be used to increase the modulation frequency o) in order to improve the resolution of the phase measurement. Multiple exponential decays may also be resolved by scanning the modulation frequency.

18.g Edge detection and other Pattern recognition maps: By changing the pattern on the rotating disk or by changing the mappings on a multirate modulator, one can provide additional functionality. The simplest case is the one in which a pattern is printed on a rotating disk such that it encodes identical frequencies at two adjacent locations that are 180 degree out of phase. In this case, the same image intensity at the two locations will result in no net modulation at the detector. The signal at the detector is then proportional to the difference in intensity between the adjacent locations the result is that the image processing function similar to edge detection $I(x)-I(x-\Delta x)$ is performed with the choice of the pattern. In general, the adjacent locations in the above example may be replaced by any regions of the image. This principle may be extended to any multirate modulator 105. As another example, consider direct measurement of a function such as $I(x+\Delta x)-2I(x)+I(x-\Delta x)$ which is proportional to the second derivative of the image. The weights may be provided by controlling the duty cycle of the pattern.

In another example, a single multirate modulator may contain a pattern that multiplexes in such a way that the reconstructed images switch between edge detection (or only high spatial frequency components) and low resolution image to directly synthesize a high resolution image. Appropriate digital or analog post-processing of the dynamically encoded electronic signal s(t) allows creating efficient edge detectors in "software".

18.h Laser-based or coherent sources and illumination: So far in this disclosure, I have assumed the the use of "incoherent" sources where the interference from different parts of the image is not present. This assumption allowed direct addition of the modulated intensities as in Equation 4. In this section, I will extend the multirate modulator technique to include imaging, range finding etc. with coherent light source such as a laser. It is noted that coherent light sources such as laser may be made "incoherent" for the purposes of imaging by use of phase plates, rapid phase modulation etc. The case discussed below is for a coherent light beam 101. For a coherent light source, the interference of the electric fields lead to many pairwise cross terms for the intensity measured on the detector. For the sake of simplicity, but without losing any generality, I will use rotating disk multirate modulator. Each location is modulated by with a unique frequency $\omega_m$. The electric fields may be written as $$E_m(t) \propto \sqrt{I_m(t)} \equiv \sqrt{I_m(1+\cos(\omega_m t))} \quad (37)$$
$$= \sqrt{2I_m}\cos((\omega_m/2)t)$$
$$= E_m\cos((\omega_m/2)t).$$

The total electric field at the detector after the collection optics is:

$$E(t) = \sum_m E_m\cos((\omega_m/2)t)\exp(i\phi_m), \quad (38)$$

where I have included the phase-shifts from each of the locations. The phases $\phi_m$ contain the speckle and other information corresponding to small variations in the path length to the detector. This includes both the static phase shifts from optics as well as any dynamic phase shifts arising from scattering of the object, its velocity, vibrations, etc. The coherent signal intensity at the detector is, $$s_c(t) = \left|\sum_m E_m\cos((\omega_m/2)t)\exp(i\phi_m)\right|^2. \quad (39)$$

Examination of the sum in the above equation reveals the following sets of terms after some algebra:

Direct terms:
$$\sum |E_m|^2\cos((\omega_m/2)t)^2 = \sum I_m(1+\cos(\omega_m t)) \equiv s(t), \text{ and} \quad (40)$$

Cross terms:

$$u(t) = \sum_{m,n>m} E_m E_n \cos(\phi_m - \phi_n) \quad (41)$$

$$\{\cos[((\omega_m + \omega_n)/2)t] + \cos[((\omega_m - \omega_n)/2)t]\}.$$

Figure 30:
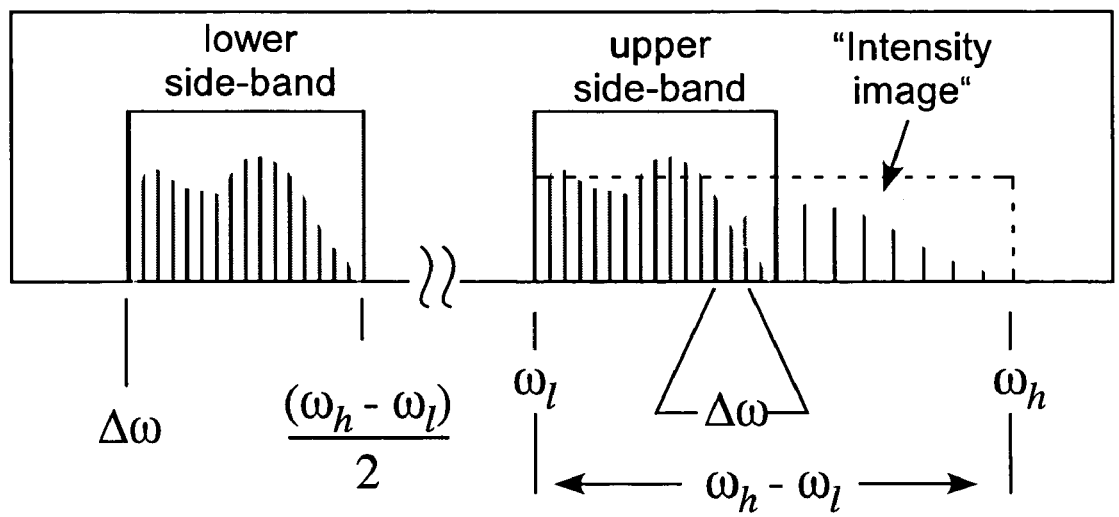
FIG. 30 shows the modulation frequency spectrum for a coherent light source.

The direct terms represent the "incoherent" terms of Equation 4 and has spectral support in the frequency region $\omega_l < \omega < \omega_h$, where $\omega_l$, $\omega_h$ are the lowest and the highest frequencies of modulation in the image. The cross terms u(t) are located in two bands—the "lower sideband" comprising of difference frequency pairs and the "upper sideband" comprising of sum frequency pairs. The lower sideband clearly does not overlap with the spectrum of s(t) but the upper sideband partly overlaps the spectrum of s(t). The spectra of each of the regions of $s_c(t)$ are shown schematically in FIG. 30.

Because of the overlap in the spectra of s(t) and the upper sideband, one can not simply reconstruct the "incoherent image" or the "intensity image" as discussed earlier, unless a method is found to distinguish the cross terms and the direct term in the overlapped region. This is the topic of discussion for the next section.

The strength of spectrum of the cross-terms in $s_c(t)$ is affected by many factors such as the size of the detector and collection optics but these may be taken into account by modifying the analysis below. For example, the light rays coming from the two ends of the image are incident on the detector at substantial angle to each other depending on the f/# of the collection optics. Multiple spatial fringes (due to tilted beams) within the size of the image on the detector will tend to wash out the interference term. Aberrations may create non-overlapping spatial profiles on the detector from the two locations on the image and thus may also reduce the interference term. If the path length difference between the two points is comparable to the coherence length or the beat length for the laser modes, the interference term is again modified. In general, the actual magnitudes of the cross-terms are changed by the aberrations, f/#, size and the position of the detector, the coherence length of the light source, and the spot size of the image on the detector. In the discussion below, I identify methods to deduce each of the terms in Equations 40 and 41 and measure their amplitudes and phases. In practical situations, absence of certain terms and knowledge of the laser source may simplify the matematical analysis required for reconstruction.

18.h.1 Extraction of the image: Clearly, one half of the intensity image may be reconstructed because there are no overlapping bands. In order to extract the entire image including the phase terms one needs to encode the modulation frequencies in such a way so as to facilitate extraction of cross-terms.

18.h.2 Cross-term or the interference-term analysis: Let us first consider the example where the modulation frequencies form a linear map with respect to the image location.

$$\omega_m = \omega_1 + m\Delta\omega \quad (42)$$

This case has been dealt in great detail in this disclosure and the above equation is equivalent to Equation 3.

One sees the pattern for the cross-terms from the examination of Equation 41. Since the amplitudes $u_1, u_2, \ldots, u_m$ corresponding to the frequencies at $\Delta\omega, 2\Delta\omega, \ldots, m\Delta\omega$ are sum of the terms with the same frequency, the set of equations are difficult to solve and involve solving transcendental simultaneous equation for the unknown phases $\phi_m$ relative to an arbitrarily chosen $\phi_N=0$ for the remaining N−1 unknown phases. Also, the overlap of the upper sideband with the direct terms further complicates the matter.

A direct solution to Equation 41 may be found if the spacing between the adjacent modulation frequency is not constant. Consider a mapping $\omega_m = \omega_1 + m\Delta\omega + m^2(\Delta\omega)\alpha$. Now each cross term in Equation 41 has a unique frequency given by (for the lower frequencies): $\omega_m - \omega_n = (m-n)\Delta\omega + (m^2 - n^2)(\Delta\omega)\alpha$.

Another possible frequency map is $\omega_m = \omega_1 + \Delta\omega(2m + \text{mod}(m, \Delta\omega))$. Many non-linear frequency maps allow reconstruction of the amplitudes of all the cross-terms and direct-terms since each term is modulated at a unique frequency.

One may also determine the amplitudes in Equation 41 even in the case of a linear frequency map. This particular solution path involves making multiple measurements by introducing a known phase change of $\pi/2$ and $\pi$ in the path of a particular location—for example that corresponding to $\omega_1$. Without loss of generality, one may set $\phi_1=0$ as a reference. One can see from the structure of Equation 40 that only the terms of the type $\phi_m - \phi_1$ change to $\cos(\phi_m)$, $\sin(\phi_m)$, $-\cos(\phi_m)$ as the phase $\phi_1$ is stepped by $0, \pi/2, \pi$. From this multiple data sets, the amplitudes and phases, $E_m$, $\phi_m$ can be found by solving for each of the frequencies in the spectrum of the lower side-band. Since some $E_m$ are known from the direct measurements except those $E_m$ whose frequencies overlap with the frequencies of the upper sideband. The unknown amplitudes are $E_2, E_4, E_{2m}, \ldots, E_{N/2}$. From the solution of the lower side-band equation $\phi_m$ and the products $E_1 E_m$ can be determined. Armed with this knowledge, one may determine all the phases and amplitudes. Reader will recognize many generalization of this technique may be made by stepping the phase in a known way. This may be considered an extension of the interferometric phase measurement technique applied to the entire image to simultaneously reconstruct speckle-free intensity image as well as relative phases.

By processing the entire coherent image, I have shown that one may measure all the relevant phase and amplitude terms. Clearly the technique may be extended (by combining with range or depth measuring ability of the multirate modulator) to measure complex image profiles and used as a coordinate measuring machine. It may also be extended to measure phase shifts from physical parameters such as temperature or electric field gradients on the object while simultaneously imaging it.

18.i Improvement in Range resolution: The laser or LED source may be modulated at very high frequency using many well-known methods. From the discussion in Section 11, one knows that the range resolution $\delta z = \delta\phi(c/(\gamma\pm\omega)) \sim \delta\phi(c/\gamma)$ where $\gamma$ is the modulation frequency of the source and $\omega_l < \omega < \omega_h$ are modulation frequencies from the multirate modulator. Typical direct modulation frequencies available with LED's are of the order of 100's of MHz while lasers can be modulated at up to tens of GHz. The modulation frequency may be varied (or chirped) using variety of well known techniques. Other laser modulation techniques include use of external modulation, current injection in semiconductor lasers, and mode beats in two-mode laser. The ADC may continue to operate at frequencies much lower than the high modulation frequency $\gamma$ since the frequencies may be translated back to the "base-band" by using heterodyne techniques. In case of very high modulation frequency (such as one created by beating the two modes of a laser), the detector itself does not have to operate at the high speed. One may also translate the frequency spectrum (or heterodyne) by beating with another laser at frequency γ' directly on the detector (and using the detector as a nonlinear mixing element) so that γ-γ' is a low frequency that can be digitized for image reconstruction and range measurement.

18.j Phase-encoding: Laser source makes it easier to use a pure phase-encoding mask as opposed to amplitude masks illustrated throughout this document. The phase-modulation may be converted to the intensity modulation for detection by using another fixed or dynamic phase-mask so that the interference of the two-masks creates an intensity modulation.

18.k Night vision and amplified imaging with Photomultiplier or APD: Since the embodiments disclosed here use a single (or a few) detectors for imaging, very high quality image signal amplification may be utilized to increase the dynamic range. For example, one may use photo-multiplier tubes or Avalanche photo-diode (PMT/APD) to collect the signal. This makes it possible to reconstruct image from very low-level signals. In this mode, this is a night vision camera. In a conventional night vision camera an image intensifier is used to amplify the low-level signals. In the multirate modulator based imager, I have use a PMT/APD which has the potential to provide a higher signal to noise ratio and/or higher amplification factor compared to traditional image intensifiers. Since the incoming data is modulated, the multirate modulator technique automatically filters the low-frequency noise produced in the amplified detectors. Another advantage of PMT/APD is a high-speed response over a large area which may substantially simplify the requirements of the collection optics after the encoding. This technique is also allows use of a pair of detectors operating in different ambient brightness to smoothly transition from "night vision" to "day vision" while maintaining a high dynamic range in the image.

The gain of PMT/APD may be tailored to the environment (AGC) and one may employ nonlinear encoding techniques (such as those discussed toward the end in Section 9) to improve the dynamic range of night vision camera. Other advantages include improved field-of-view and multi-wavelength monitoring using the same camera head.

Figure 27:
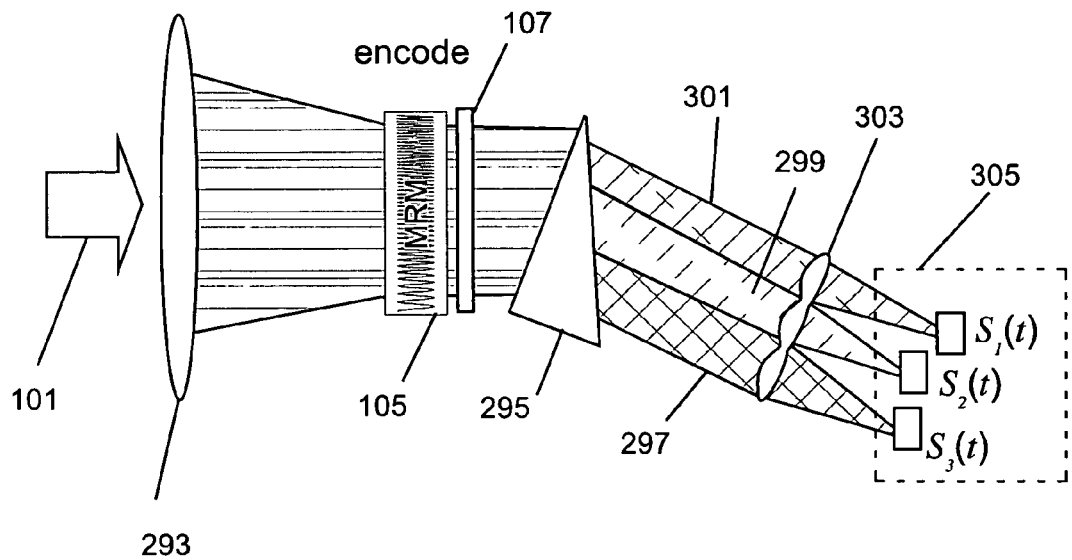
FIG. 27 is a three-wavelength band camera operating with a single multirate modulator.

18.l Multi-wavelength or Hyperspectral Imaging including RGB camera: The techniques described in this disclosure are particularly suitable for simultaneous imaging in multiple regions of electromagnetic spectrum. FIG. 27 shows an example of simultaneous imaging of a scene or an object in three electromagnetic bands. They may be visible, mid infrared (3-5 micron) and thermal (8-14 micron) region of the electromagnetic spectrum analogous to the three visible spectral bands of the RGB camera. The electromagnetic radiation 101 from the scene and/or an object is imaged using an achromatic lens system 293 (and/or a combination of lenses and mirrors) capable of imaging the entire electromagnetic spectrum of interest. The spectral bands corresponding to the three electromagnetic regions 297, 299, and 301 are separated by a dispersive (or any other spectral filter) system 295 after dynamically encoding by multirate modulator. After inserting appropriate light gathering optics 303 (for each wavelength region), the electromagnetic regions are received by a detector system 305. In this case, the detector system 305 may use three detector systems 111 (one for each electromagnetic region) which further contains detector elements 112 appropriate for corresponding EM region. These detector systems produce dynamically encoded electronic signal (such as 114) for each of the EM regions shown as $s_1(t)$, $s_2(t)$, $s_3(t)$ etc. The principle illustrated here may be extended to any number of spectral bands for higher-resolution spectroscopic analysis of the incident image.

The reconstructed images of different wavelength regions from each of the detectors are registered to each other since they were encoded by the multirate modulator placed in the image plane which simultaneously modulated all of the radiation. Due to a separate detector system for each of the wavelengths and the reconstruction algorithms that allow frame rate and the resolution to be controlled in software, each of the wavelength regions may be updated at different rates and have user defined sensitivities. Efficient separation of the different wavelength regions may be accomplished by the use of multiple thin film filters, coarse grating, dispersive prisms, etc.

This technique may also be useful in the visible region of the spectrum for color imaging. Most 2D CCD/CMOS imagers use either a color wheel or a filter pattern of RGB pixels. This reduces the actual resolution of the CCD and causes well known issues of color Moire patterns as well loss of color fidelity. As discussed above, the multirate modulator based imager described here may record the three (or more) color channels without the loss of resolution with excellent registration of pixels among the color channels.

18.m Masks on curved surface to reduce optical distortion: A patterned mask may be printed on a curved surface as opposed to a planar disk. This may correct for the distortion in the focal plane introduced by the imaging lenses. Generally, making the image field flat in order to produce a sharp image on a planar imaging surface increases the complexity of the imaging system and adds to the cost of optics. By printing on a curved surface, the multirate modulator may be designed to have the same curvature as the image field produced by the optical imaging system or a curved object. After dynamical encoding, a planar detector can be used to collect light. This may be used to reduce or eliminate distortions while simplifying optical components. The curved cylindrical masks of the type shown in FIG. 12b may simultaneously correct for the curvature of the image in both the directions. In another example, consider using a fish-eye lens which normally produces a distorted image of the scene die to mapping on a planar planar imaging surface. By using the encoding functions on a curved surface, one may simplify design of the fish-eye lens and reduce the distortion.

In ophthalmology, imaging the surface of the retina has become quite important for diagnostics of the eye. It is quite difficult to acquire high-resolution images of the retina using a standard planar imaging system since the human lens in the eye is designed to image on a curved surface—the surface of the retina. Imaging based on multirate modulator disclosed may provide a practical solution to imaging curved objects. This is because non-planar image may be reconstructed by conforming the multirate modulator to the curvature of the imaging surface.

18.n Segmented masks for large dynamic range, wavelength filtering wheels etc. The multirate modulator based on patterned masks may itself include multiple functions. Examples masks with different regions that have:
(a) different transmission so that very high dynamic range image may be constructed
(b) different sections of the mask modulate different wavelength regions of the image so that "color" image may be reconstructed. This may be accomplished by building a thin film optical color filters directly on the patterned mask.

(c) different segments to provide interleaved scanning.

(d) different segments with different phase/amplitude modulation to improve phase decoding for range resolution or phase-delay measurements 18.o Binocular and other large field of view imaging: Many of the examples of multirate modulator provided in this disclosure allow simultaneous encoding of multiple images by using a detector per imaging channel. For example, the two sides of the disk may be used to simultaneously provide a stereo view of the scene.

Figure 31:
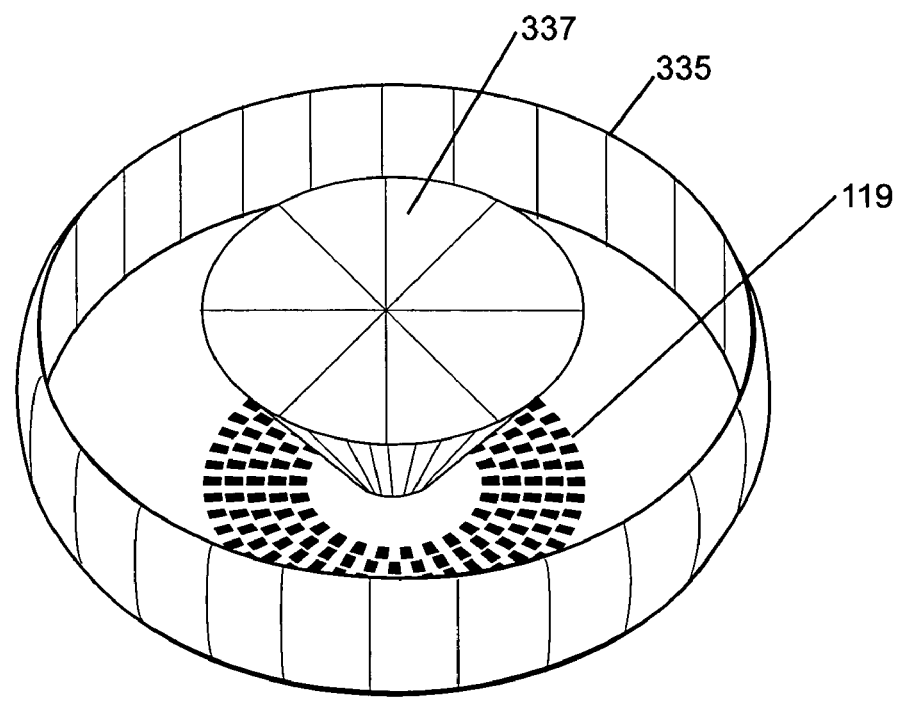
FIG. 31 shows an imaging camera with a 360 degree field of view.

FIG. 31 illustrates a multirate modulator based imaging system that provides a 360-degree horizontal field of view (FOV). This can be adapted for any large fields of view which are difficult to achieve using traditional systems in which large FOV is performed by scanning and stitching or using a fish-eye lens which distorts the scene. A combination of the imaging system 335 and the conical reflector 337 creates the image on the plane of the rotating disk 119. The vertical direction is mapped to r, and the horizontal direction is mapped to θ. One may use multiple detectors for collection of encoded light from each of the sectors may be used for reconstruction of 2D data. Of course, the technique of 2D reconstruction discussed in Section 17 may be used to reduce the number of detectors. For example, in the FIG. 31, one may use a chirped disk for encoding the entire 2D (r, θ) data. A fiber bundle may also be utilized to collect the encoded light on a single detector.

In further embodiments, the field of view may not span a full 360-degrees. For example, it might span any of 90-degrees or more, 180-degrees or more, or 270-degrees or more.

18.p Polarization imaging: This is an extension of ellipsometry technique applied to the entire image. Recently, there have been many suggestions that certain kind of fish use polarization-difference imaging to find objects in scattering media. This sort of imaging uses the fact that the polarization of the scattered light depends on the relative orientation of the observer to the light source and its polarization properties. In general, a camera that allows one to construct an image of Stokes vectors could be very useful to find the correct and optimal algorithm for distinguishing objects hidden in scattering media.

A simple 1D example is given here that allows one to construct the polarization vector for each location on the image. Consider encoding based on a rotating disk made on a quarter wave plate (many other values of retardance will do). The signal s(t) is collected after the image is transmitted through a polarizer. This is a direct extension of the ellipsometry application discussed earlier and many other ellipsometric geometries may be used to generate essentially the same information. The intensity at each pixel location is further modulated by a rotation of the wave-plate, which in turn generates side-bands around each modulation frequency. For a quarter waveplate, the polarization induced modulation frequency will be 4 times $f_{disk}$. One can determine the polarization state of the light by analyzing the modulation spectrum in conjuction with the theory of ellipsometers and polarization of light. This may entail extracting amplitudes of the sidebands as well as the total intensity of each pixel.

19 Lensless Imaging: For many of the imaging applications, I have assumed that an appropriate lens or a lens system is used to form an image on the surface of the multirate modulator. In many imaging applications, lenses are either expensive or nonexistent. The EM regions where lenses are relatively expensive include infrared and mm wave regions. The EM regions where lenses/mirrors are nonexistent or extremely difficult to form include X-ray and gamma-ray regions. In such cases, one may use the multirate modulator to form an image without the lens.

In order to form the image without the lens, one combines the principle of a pin-hole camera and dynamic encoding. Consider the geometry shown in FIG. 32. I use at least two multirate modulators 105a and 105b separated by a distance l in order to directly form the image on a detector system 111. For a detector element 343 at point $x_0$, the modulation of ray 339, travelling from a point on object 341 intersects the two encoders at two different locations $x_1$ and $x_2$. This in turn gives rise to the signal on the detector element 343 as (ignoring the overall transmission factor)

$$s_r(t)=I(X)\cos[\omega(x_1)t]\cos[\omega(x_2)t]. \quad (43)$$

Further, assume a linear map for the modulation frequency as a function of x on each of the disks given by $$\omega_m=(2\pi x_m/\Lambda)\Delta\omega. \quad (44)$$

Figure 32:
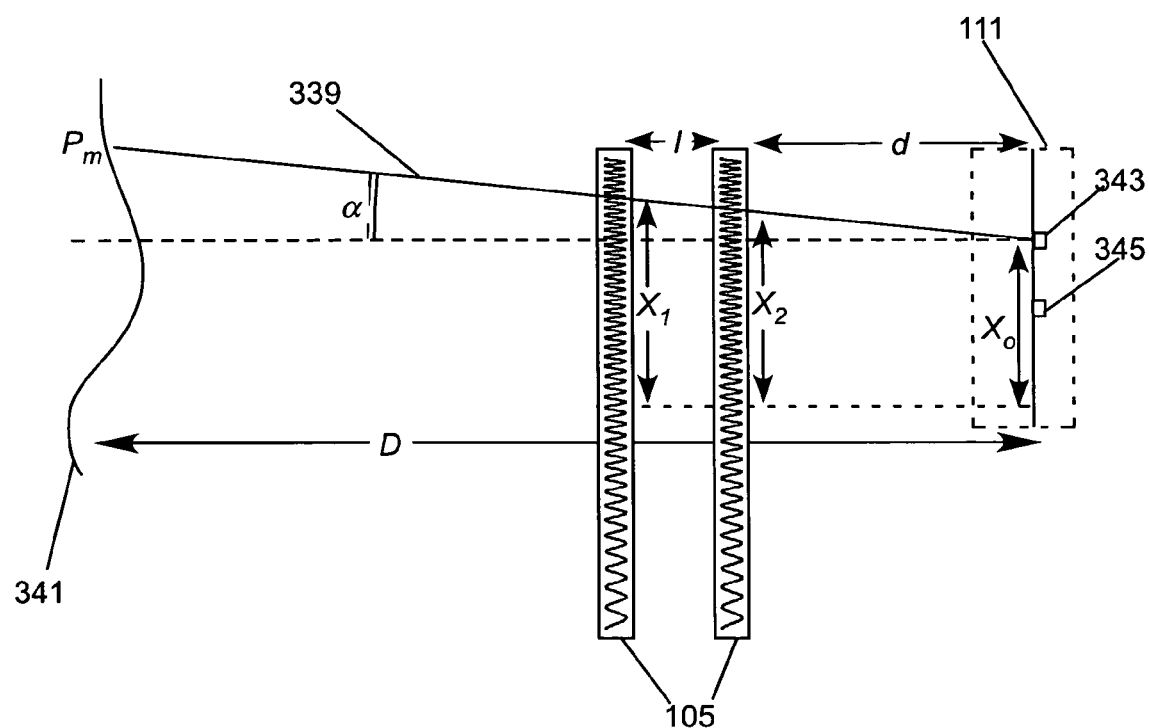
FIG. 32 illustrates the principle of operation for lensless camera.

Let α be the angle of this ray 339 as shown in the FIG. 32. Then, $$x_1=d\alpha+x_0 \text{ and } x_2=(d+l)\alpha+x_0. \quad (45)$$

The aperture of the system determines the limits on the allowed values of α. Using an example of a linear frequency map, one can simplify the above equation by splitting it into sum- and difference-frequency components. After some algebra, the modulation is given by $$s_r(t)=I(X)\{\cos[(2\pi/\Lambda)\Delta\omega l\alpha t]+\cos[(2\pi/\Lambda)\Delta\omega(2d+l+2x_0)\alpha t]\}. \quad (46)$$

The lower difference frequency term and the higher sum-frequency term may be separated by filtering. Both of these terms have encoded image information that allows reconstruction of the image of object 341. In the simplest case, one may only use the difference frequency components or the lower side band. This is achieved by placing a large detector such that the signal is integrated over the entire detector surface either by a large physical detector and/or by simply summing the output of multiple detectors to form an equivalent large detector. The total lower band signal received by the detector system 111 in this case is $$s(t)=\int\int d\alpha I[D\alpha+x_0]\cos[(2\pi/\Lambda)\Delta\omega l\alpha t]dx_0. \quad (47)$$

After integrating with respect to $x_0$ the angle resolved image can be reconstructed from the encoded signal. In this case, the size of the detector limits the resolution of the reconstructed image.

The resolution may be improved (while collecting light from the aperture) by using a detector array comprising of detector elements 343, 345, etc. Each small element of the array produces a high resolution image. In this case, we may treat each of the elements 343, 345, etc. as a detector system 111 with each producing a dyamically encoded signal. The reconstructed images from each of the detectors may be combined with appropriate offsets to produce a high resolution image. The use of arrayed detector systems also allows one to use the upper frequency region (where the argument of the cosine depends on the position of the detector). One can maintain a good light collection efficiency Since the reconstructed images from each of the small detectors in the array are combined.

Note that this dual multirate modulator based lensless camera operates in a manner similar to a pin-hole camera with an added advantage of having a light collection efficiency determined by the aperture of the system. This principle for lensless imaging outlined above for the case of 1D may be extended to the 2D domain by using 2D multirate modulators.

The lensless imaging system disclosed here may be used directly in place of imaging system 103 shown in FIG. 1a. It may be used in any of the application discussed in this disclosure.

Additional embodiments, features, and advantages are within the scope of the following claims

What is claimed is:

1. A method, comprising:
    modulating multiple components corresponding to different spatial regions of electromagnetic (EM) radiation emerging from an object with different time-varying functions, wherein the modulating comprises directly modulating EM radiation incident on the object or EM radiation emerging from the object by moving a first permanently patterned mask relative to the object;
    measuring at least one time-varying signal derived from the modulated EM radiation emerging from the object; and
    reconstructing information about the object based on the measured signal and the time-varying functions,
    wherein the measuring comprises converting an analog measurement signal to a digital measurement signal using at least one analog-to-digital converter (ADC), and wherein operation of the at least one ADC is synchronized to a clocking signal derived from a portion of the first permanently patterned mask.

2. The method of claim 1, further comprising outputting at least a portion of the reconstructed information.

3. The method of claim 1, wherein the clocking signal is a periodic signal.

4. The method of claim 1, wherein the clocking signal is generated by directing radiation to be incident on the portion of the first permanently patterned mask, detecting a portion of the radiation that is transmitted through the mask, and producing an electrical signal that corresponds to the detected radiation.

5. The method of claim 1, wherein some of the multiple components correspond to different wavelengths of the EM radiation.

6. The method of claim 1, wherein the EM radiation emerging from the object is derived from EM radiation incident on the object, and the multiple components of the EM radiation emerging from the object are modulated by directly modulating the EM radiation incident on the object.

7. The method of claim 1, wherein the multiple components of the EM radiation emerging from the object are modulated by directly modulating the EM radiation emerging from the object.

8. The method of claim 1, wherein the modulating comprises modulating at least one of an amplitude, a phase, and a state of polarization (SOP) of at least some of the components of the EM radiation emerging from the object.

9. The method of claim 1, wherein the modulating further comprises moving a second permanently patterned mask relative to the object and the first permanently patterned mask.

10. The method of claim 1, wherein the modulating further comprises dispersing source radiation to produce spatially separated wavelengths, directly modulating the spatially separated wavelengths, and directing the modulated wavelengths to contact the object to produce the EM radiation emerging from the object.

11. The method of claim 1, wherein the modulating further comprises dispersing source radiation to produce spatially separated wavelengths, directly modulating the spatially separated wavelengths, spatially recombining the modulated wavelengths, and directing the modulated wavelengths to contact the object to produce the EM radiation emerging from the object.

12. The method of claim 1, wherein the at least one time-varying signal comprises M signals, where M is greater than or equal to 1, and wherein the reconstructed information comprises N independent data points, where N>M.

13. The method of claim 1, wherein the measuring of the time-varying signal derived from the temporally modulated EM radiation comprises directing at least some of the different spatial regions of the EM radiation to a common detector and measuring a time-varying intensity of aggregate EM radiation incident on the common detector.

14. The method of claim 1, wherein the at least one time-varying signal comprises multiple time-varying signals, and wherein the measuring of the time-varying signals derived from the temporally modulated EM radiation comprises directing each of different sets of a plural number of the multiple spatial regions of the EM radiation to a corresponding detector and measuring a time-varying intensity of aggregate EM radiation incident on each detector.

15. The method of claim 1, wherein the measuring of the time-varying signal derived from the temporally modulated EM radiation comprises directing at least some of the multiple spatial regions of the EM radiation to interfere with reference EM radiation on a common detector and measuring a time-varying interference signal of aggregate EM radiation incident on the common detector, wherein the EM radiation emerging from the object and the reference EM radiation are derived from a common source.

16. The method of claim 15, wherein the reconstructed information comprises information about one or more of amplitudes, phases, state of polarization (SOP) information, and wavelengths of the EM radiation emerging from the object relative to the reference EM radiation.

17. The method of claim 1, wherein the EM radiation emerging from the object comprises wavelengths that span multiple wavelength regions that are separated from one another.

18. The method of claim 17, wherein the at least one time-varying signal comprises multiple time-varying signals, and wherein the measuring of the time-varying signals derived from the temporally modulated EM radiation comprises directing at least some of the multiple spatial regions of the EM radiation at wavelengths in each of the multiple wavelength regions to a corresponding detector and measuring a time-varying intensity of aggregate EM radiation incident on each detector.

19. The method of claim 17, further comprising illuminating the object at wavelengths that span each of the multiple wavelength regions to produce the EM radiation emerging from the object.

20. The method of claim 1, wherein the reconstructed information comprises an image of the object formed from multiple wavelengths of the EM radiation.

21. The method of claim 1, further comprising illuminating the object with incident EM radiation to produce the EM radiation emerging from the object.

22. The method of claim 1, wherein the EM radiation emerging from the object comprises EM radiation in the X-ray region.

23. The method of claim 1, wherein the EM radiation emerging from the object comprises EM radiation in at least one of the infrared region and the millimeter-wave region.

24. The method of claim 1, further comprising imaging the radiation from the object onto the first permanently patterned mask to modulate the multiple components.

25. The method of claim of 1, further comprising positioning at least two permanently patterned masks in a path of the EM radiation, wherein the radiation from the object reaches the two masks without passing through an imaging optic having an optical power, and wherein the reconstructing of the information about the object uses information about a distance between the two masks.

26. An apparatus, comprising:
a modulator configured to modulate multiple components corresponding to different spatial regions of electromagnetic (EM) radiation emerging from an object with different time-varying functions, wherein the modulating comprises directly modulating EM radiation incident on the object or EM radiation emerging from the object by moving a permanently patterned mask relative to the object;
a detector configured to measure at least one time-varying signal derived from the modulated EM radiation emerging from the object; and
an electronic processor electrically coupled to the detector and the modulator, and configured to reconstruct information about the object based on the measured signal and the time-varying functions,
wherein the measuring comprises converting an analog measurement signal to a digital measurement signal using at least one analog-to-digital converter (ADC), and wherein operation of the at least one ADC is synchronized to a clocking signal derived from a portion of the permanently patterned mask.

27. The apparatus of claim 26, wherein the processor is configured to output at least a portion of the reconstructed information.

28. The apparatus of claim 26, wherein the clocking signal is a periodic signal.

29. The apparatus of claim 26, further comprising a source configured to direct EM radiation to be incident on the portion of the first permanently patterned mask, and wherein the detector is configured to detect a portion of the radiation that is transmitted through the mask and to produce an electrical signal that corresponds to the detected portion of the radiation.

30. The apparatus of claim 26, wherein some of the multiple components correspond to different wavelengths of the EM radiation.

31. The apparatus of claim 26, wherein the EM radiation emerging from the object is derived from EM radiation incident on the object, and the modulator is configured to directly modulate the EM radiation incident on the object.

32. The apparatus of claim 26, wherein the modulator is positioned to directly modulate the EM radiation emerging from the object.

33. The apparatus of claim 26, wherein the modulator is positioned to modulate at least one of an amplitude, a phase, and a state of polarization (SOP) of at least some of the components of the EM radiation emerging from the object.

34. The apparatus of claim 26, wherein the modulator comprises a second permanently patterned mask that is movable relative to the object and the first permanently patterned mask.

35. The apparatus of claim 26, wherein the modulator is configured to disperse source radiation to produce spatially separated wavelengths, to directly modulate the spatially separated wavelengths, and to direct the modulated wavelengths to contact the object to produce the EM radiation emerging from the object.

36. The apparatus of claim 26, wherein the modulator is configured to disperse source radiation to produce spatially separated wavelengths, to directly modulate the spatially separated wavelengths, to spatially recombine the modulated wavelengths, and to direct the modulated wavelengths to contact the object to produce the EM radiation emerging from the object.

37. The apparatus of claim 26, wherein the at least one time-varying signal comprises M signals, wherein M is greater than or equal to 1, and wherein the reconstructed information comprises N independent data points, wherein N>M.

38. The apparatus of claim 26, wherein the detector is configured to detect EM radiation from at least some of the different spatial regions of the EM radiation, and to measure a time-varying intensity of aggregate EM radiation incident on the detector.

39. The apparatus of claim 26, wherein the at least one time-varying signal comprises multiple time-varying signals, and wherein the apparatus is configured to measure the time-varying signals by directing each of different sets of a plural number of the multiple spatial regions of the EM radiation to the detector, the detector being configured to measure a time-varying intensity of aggregate EM radiation incident thereon.

40. The apparatus of claim 26, wherein the apparatus is configured to direct at least some of the multiple spatial regions of the EM radiation to interfere with reference EM radiation on the detector, the detector being configured to measure a time-varying interference signal of aggregate EM radiation incident thereon, and wherein the EM radiation emerging from the object and the reference EM radiation are derived from a common source.

41. The apparatus of claim 40, wherein the reconstructed information comprises information about one or more of amplitudes, phases, state of polarization (SOP) information, and wavelengths of the EM radiation emerging from the object relative to the reference EM radiation.

42. The apparatus of claim 26, wherein the EM radiation emerging from the object comprises wavelengths that span multiple wavelength regions that are separated from one another.

43. The apparatus of claim 42, wherein the at least one time-varying signal comprises multiple time-varying signals, and wherein the apparatus is configured to direct at least some of the multiple spatial regions of the EM radiation at wavelengths in each of the multiple wavelength regions to the detector, the detector being configured to measure a time-varying intensity of aggregate EM radiation incident thereon.

44. The apparatus of claim 42, further comprising a source configured to illuminate the object at wavelengths that span each of the multiple wavelength regions to produce the EM radiation emerging from the object.

45. The apparatus of claim 26, wherein the reconstructed information comprises an image of the object formed from multiple wavelengths of the EM radiation.

46. The apparatus of claim 26, further comprising a source configured to illuminate the object with incident EM radiation to produce the EM radiation emerging from the object.

47. The apparatus of claim 26, wherein the detector is configured to measure EM radiation emerging from the object in the X-ray region.

48. The apparatus of claim 26, wherein the detector is configured to measure EM radiation emerging from the object in at least one of the infrared region and the millimeter-wave region.

49. The apparatus of claim 26, wherein the apparatus is configured to image the radiation from the object onto the first permanently patterned mask to modulate the multiple components.

50. The apparatus of claim of 26, wherein the modulator comprises at least two permanently pattern masks positioned in a path of the EM radiation, wherein the radiation from the object reaches the two masks without passing through an imaging optic having an optical power, and wherein the processor is configured to reconstruct the information about the object based on information about a distance between the two masks.

* * * * *